United States Patent
Rothenberg et al.

(10) Patent No.: US 9,624,545 B2
(45) Date of Patent: *Apr. 18, 2017

(54) ESOPHAGEAL MICRORNA EXPRESSION PROFILES IN EOSINOPHILIC ESOPHAGITIS

(71) Applicant: CHILDREN'S HOSPITAL MEDICAL CENTER, Cincinnati, OH (US)

(72) Inventors: Marc E. Rothenberg, Cincinnati, OH (US); Thomas Xuefeng Lu, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/989,243

(22) Filed: Jan. 6, 2016

(65) Prior Publication Data
US 2016/0177394 A1    Jun. 23, 2016

Related U.S. Application Data

(63) Continuation of application No. 14/380,672, filed as application No. PCT/US2013/027503 on Feb. 22, 2013, now Pat. No. 9,260,756.

(60) Provisional application No. 61/602,897, filed on Feb. 24, 2012.

(51) Int. Cl.
C07H 21/02    (2006.01)
C07H 21/04    (2006.01)
C12Q 1/68    (2006.01)
C12N 15/11    (2006.01)

(52) U.S. Cl.
CPC .......... *C12Q 1/6883* (2013.01); *C12N 15/111* (2013.01); *C12N 2310/141* (2013.01); *C12N 2320/10* (2013.01); *C12Q 2600/158* (2013.01); *C12Q 2600/178* (2013.01)

(58) Field of Classification Search
CPC A61K 48/00; C12N 15/113; C12N 2310/141; C12N 15/111
See application file for complete search history.

(56) References Cited

U.S. PATENT DOCUMENTS

| | | | |
|---|---|---|---|
| 4,522,811 | A | 6/1985 | Eppstein et al. |
| 8,030,003 | B2 | 10/2011 | Rothenberg |
| 9,260,756 | B2 | 2/2016 | Rothenberg et al. |
| 2009/0269774 | A1 | 10/2009 | Rothenberg et al. |
| 2011/0195500 | A1 | 8/2011 | Rothenberg |
| 2011/0301046 | A1 | 12/2011 | Rothenberg et al. |
| 2012/0004205 | A1 | 1/2012 | Rothenberg |
| 2012/0283117 | A1 | 11/2012 | Rothenberg |
| 2013/0065972 | A1 | 3/2013 | Dent et al. |
| 2013/0324435 | A1 | 12/2013 | Rothenberg et al. |
| 2014/0228315 | A1 | 8/2014 | Rothenberg et al. |
| 2014/0286896 | A1 | 9/2014 | Rothenberg et al. |

FOREIGN PATENT DOCUMENTS

| | | |
|---|---|---|
| WO | WO-2006/119343 | 11/2006 |
| WO | WO-2012/094643 | 7/2012 |
| WO | WO-2012/174549 | 12/2012 |
| WO | WO-2012/177945 | 12/2012 |
| WO | WO-2012/178188 | 12/2012 |
| WO | WO-2013/126834 | 8/2013 |

OTHER PUBLICATIONS

Abonia et al., "Involvement of mast cells in eosinophilic esophagitis," J. Allergy Clin. Immunol., Jul. 2010, pp. 140-149, vol. 126(1).
Aceves et al., "Mast cells infiltrate the esophageal smooth muscle in patients with eosinophilic esophagitis, express TGF-131, and increase esophageal smooth muscle contraction," Dec. 2010, pp. 1198-1204, vol. 126(6).
Ackerman et al., "Charcot-Leyden crystal protein (galectin-10) is not a dual function galectin with lysophospholipase activity but binds a lysophospholipase inhibitor in a novel structural fashion," J. Biol. Chem., Apr. 26, 2002, pp. 14859-14868, vol. 277(17).
Adachi et al., "Transduction of phosphatase and tensin homolog deleted on chromosome 10 into eosinophils attenuates survival, chemotaxis, and airway inflammation," J. Immunol., Dec. 15, 2007, pp. 8105-8111, vol. 179(12).
Anonymous: "TagMan(R) Human MicroRNA Arrays", Jun. 2008, pp. 1-2, XP055200589, Carlsbad, CA, USA; URL:https://tools.lifetechnologies.com/content/sfs/manuals/cms_054742.pdf [retrieved on Jul. 7, 2015].
Anthony et al., "Protective immune mechanisms in helminth infection," Dec. 2007, Nat. Rev. Immunol., pp. 975-987, vol. 7(12).

(Continued)

*Primary Examiner* — Amy Bowman
(74) *Attorney, Agent, or Firm* — Mintz Levin Cohn Ferris Glovsky and Popeo, P.C.; Muriel Liberto, Esq.

(57) ABSTRACT

Methods and compositions disclosed herein generally relate to methods of treating eosinophilic esophagitis (EE) and eosinophilic disorders by providing or enhancing a diagnosis of EE and eosinophilic disorders. In particular, the invention relates to obtaining a sample from a patient, then quantifying from the sample an amount of one or more microRNAs (miRNAs) associated with EE, wherein an altered level of the miRNA correlates with a positive diagnosis of EE. An EE diagnosis can then be provided or enhanced, based upon the quantifying step, and an appropriate treatment can be administered to the patient. The invention further relates to diagnostic kits, tests, and/or arrays that can be used to quantify the one or more miRNAs associated with EE, as well as treatments developed to up-regulate or down-regulate one or more miRNAs and/or their downstream pathways relevant to EE or asthma. The invention further relates to the use of IGF1 and IGF1R inhibitors for the treatment of EE and eosinophilic disorders.

13 Claims, 44 Drawing Sheets

(56) References Cited

OTHER PUBLICATIONS

Arefi et al., "Response to imatinib mesylate in patients with hypereosinophilic syndrome," International Journal of Hematology, Sep. 2012, pp. 320-326, vol. 96(3) [abstract only].

Arroyo et al., "Argonaute2 complexes carry a population of circulating microRNAs independent of vesicles in human plasma," P.N.A.S., Mar. 22, 2011, pp. 5003-5008, vol. 108(12).

Assa'ad et al., "An antibody against IL-5 reduces numbers of esophageal intraepithelial eosinophils in children with eosinophilic esophagitis," Gastroenterology, Nov. 2011, pp. 1593-1604, vol. 141(5).

Assa'ad et al., "Pediatric patients with eosinophilic esophagitis: An 8-year follow-up," J. Allergy Clin. Immunol., Mar. 2007, pp. 731-738, vol. 119.

Bhattacharya et al., "Increased expression of eotaxin-3 distinguishes between eosinophilic esophagitis and gastroesophageal reflux disease," Hum. Pathol., May 8, 2007, pp. 1744-1753, vol. 38.

Biton et al., "Epithelial microRNAs regulate gut mucosal immunity via epithelium-T cell crosstalk," Nat. Immunol., Mar. 2011, pp. 239-246, vol. 12(3) [abstract only].

Blanchard et al., "A striking local esophageal cytokine expression profile in eosinophilic esophagitis," J. Allergy Clin. Immunol., Jan. 2011, pp. 208-217, vol. 127(1).

Blanchard et al., "Basics Pathogenesis of Eosinophilic Esophagitis," Gastrointest. Endosc. Clin. N. Am., Jan. 2008, pp. 133-143, vol. 18(1).

Blanchard et al., "Coordinate interaction between IL-13 and epithelial differentiation cluster genes in eosinophilic esophagitis," J. Immunol., Apr. 1, 2010, pp. 4033-4041, vol. 184(7).

Blanchard et al., "Eosinophilic esophagitis: pathogenesis, genetics, and therapy," J. Allergy Clin. Immunol., Nov. 2006, pp. 1054-1059, vol. 118(5).

Blanchard et al., "Eotaxin-3 and a uniquely conserved gene-expression profile in eosinophilic esophagitis," J. Clin. Invest., Feb. 2006, pp. 536-547, vol. 116(2).

Blanchard et al., "Eotaxin-3/CCL26 gene expression in intestinal epithelial cells is up-regulated by interleukin-4 and interleukin-13 viat the signal transducer and activator of transcription 6," Int. J. Biochem. Cell. Biol., Jun. 15, 2005, pp. 2559-2573, vol. 37.

Blanchard et al., "IL-13 involvement in eosinophilic esophagitis: transcriptome analysis and reversibility with glucocorticoids," J. Allergy Clin. Immunol., Dec. 2007, pp. 1292-1300, vol. 120(6).

Blanchard et al., "Periostin facilitates eosinophil tissue infiltration in allergic lung and esophagael responses," Mucosal. Immunol., Jul. 2008, pp. 289-296, vol. 1(4).

Broide et al., "Advances in mechanisms of asthma, allergy, and immunology in 2010," J. Allergy Clin. Immunol., Mar. 2011, pp. 689-695, vol. 127(3).

Buitenhuis et al., "Differential regulation of granulopoiesis by the basic helix-loop-helix transcriptional inhibitors Idl and Id2," Blood, Jun. 1, 2005, pp. 4272-4281, vol. 105(11).

Burnett et al., "RNA-based Therapeutics: Current Progress and Future Prospects," Chemistry and Biology Review, Jan. 27, 2012, pp. 60-71, vol. 19.

Buscaglia et al., "Apoptosis and the target genes of microRNA-21," Chin. J. Cancer, Jun. 2011, pp. 371-380, vol. 30(6).

Cai et al., "The imprinted H19 noncoding RNA is a primary microRNA precursor," RNA, Mar. 2007, pp. 313-316, vol. 13(3).

Caldwell et al., "Glucocorticoid-regulated genes in eosinophilic esophagitis: A role for FKBP51," J. Allergy Clin. Immunol., Apr. 2010, pp. 879-888.e8, vol. 125(4).

Carthew, "Origins and Mechanisms of miRNAs and siRNAs," Cell, Feb. 20, 2009, pp. 642-55, vol. 136(4).

Chen et al., "ToppGene Suite for gene list enrichment analysis and candidate gene prioritization," Nucleic Acids Res., Jul. 2009, pp. W305-W311, vol. 37.

Cheverud, "A simple correction for multiple comparisons in interval mapping genome scans," Heredity, Jul. 2001, pp. 52-58, vol. 87(Pt. 1) [abstract only].

Collison et al., "Inhibition of house dust mite-induced allergic airways disease by antagonism of microRNA-145 is comparable to glucocorticoid treatment," J. Allergy Clin. Immunol., Jul. 2011, pp. 160-167.e4, vol. 128(1).

Corren et al., "Lebrikizumab treatment in adults with asthma," N. Engl. J. Med., Sep. 22, 2011, pp. 1088-1098, vol. 365(12).

de Souza Rocha Simonini et al., "Epigenetically deregulated microRNA-375 is involved in a positive feedback loop with estrogen receptor alpha in breast cancer cells," Nov. 15, 2010, Cancer Res., pp. 9175-9184, vol. 70(22).

Dellon et al., "Tryptase staining of mast cells may differentiate eosinophilic esophagitis from gastroesophageal reflux disease," Am. J. Gastroenterol., Feb. 2011, pp. 264-271, vol. 106(2) [abstract only].

Dewson et al., "Interleukin-5 inhibits translocation of Bax to the mitochondria, cytochrome c release, and activation of caspases in human eosinophils," Blood, Oct. 1, 2001, pp. 2239-2247, vol. 98(7).

Donato et al., "Human HTm4 is a hematopoietic cell cycle regulator," J. Clin. Invest., Jan. 2002, pp. 51-58, vol. 109(1).

Dyer et al., "Functionally competent eosinophils differentiated ex vivo in high purity from normal mouse bone marrow," J. Immunol., Sep. 15, 2008, pp. 4004-4009, vol. 181(6).

Fahy, "Epithelial desquamation in asthma," Am. J Respir. Crit. Care Med., Nov. 15, 2001, pp. S46-S51, vol. 164(10 Pt 1).

Flower, "Modelling G-protein-coupled receptors for drug design," Biochim. Biophys. Acta., Nov. 16, 1999, pp. 207-234, vol. 1422(3).

Fukao et al., "An evolutionarily conserved mechanism for microRNA-223 expression revealed by microRNA gene profiling," Cell, 2007, pp. 617-631, vol. 129(3).

Fulkerson et al., "A central regulatory role for eosinophils and the eotaxin/CCR3 axis in chronic experimental allergic airway inflammation," Proc. Natl. Acad. Sci. U.S.A., Oct. 31, 2006, pp. 16418-16423, vol. 103(44).

Fulkerson et al., "Targeting eosinophils in allergy, inflammation and beyond," Nat. Rev. Drug Discov., Online: Jan. 21, 2013, 13 pgs.

Furuta et al., "Eosinophilic esophagitis in children and adults: a systematic review and consensus recommendations for diagnosis and treatment," Gastroenterology, Oct. 2007, pp. 1342-1363, vol. 133(4).

Garbacki et al., "MicroRNAs profiling in murine models of acute and chronic asthma: a relationship with mRNAs targets," PLoS One, Jan. 28, 2011, p. e16509, vol. 6(1).

Garcia-Echeverria et al., "In vivo antitumor activity of NVP-AEW541—A novel, potent, and selective inhibitor of the IGF-IR kinase," Cancer Cell, Mar. 2004, pp. 231-239, vol. 5.

Georgantas et al., "CD34+ hematopoietic stem-progenitor cell microRNA expression and function: a circuit diagram of differentiation control," Proc. Nat. Acad. Sci. USA, Feb. 20, 2007, pp. 2750-2755, vol. 104(8).

Griffiths-Jones et al., "miRBase: microRNA sequences, targets and gene nomenclature," Nucleic Acids Res., Jan. 1, 2006, pp. D140-D144, vol. 34(Database issue).

Griffiths-Jones et al., "miRBase: tools for microRNA genomics," Nucleic Acids Res., Jan. 2008, pp. D154-D158, vol. 36(Database issue).

Hatley et al., "Modulation of K-Ras-dependent lung tumorigenesis by MicroRNA-21," Cancer Cell., Sep. 14, 2010, pp. 282-293, vol. 18(3).

Hogan et al., "Eosinophils: biological properties and role in health and disease," Clin. Exp. Allergy, May 2008, pp. 709-750, vol. 38(5).

Iwasaki et al., "Identification of eosinophil lineage-committed progenitors in the murine bone marrow," J. Exp. Med., Jun. 20, 2005, pp. 1891-1897, vol. 201(12).

Jakiela et al., "Intrinsic pathway of apoptosis in peripheral blood eosinophils of Churg-Strauss syndrome," Rheumatology (Oxford), Oct. 2009, pp. 1202-1207, vol. 48(10).

Jia et al., "Mistl regulates pancreatic acinar cell proliferation through p21 CIP1/WAF1," Gastroenterology, Nov. 2008, pp. 1687-1697, vol. 135(5).

Jiang, "The emerging role of microRNAs in asthma," Mol. Cell. Biochem., Jul. 2011, pp. 35-40, vol. 353(1-2) [abstract only].

(56) References Cited

OTHER PUBLICATIONS

Johnnidis et al., "Regulation of progenitor cell proliferation and granulocyte function by microRNA-223," Nature, Feb. 28, 2008, pp. 1125-1129, vol. 451(7182) [abstract only].
Junttila et al., "Tuning sensitivity to IL-4 and IL-13: differential expression of IL-4Ralpha, IL-13Ralphal, and gammac regulates relative cytokine sensitivity," J. Exp. Med., Oct. 27, 2008, pp. 2595-2608, vol. 205(11).
Kaiko et al., "New insights into the generation of Th2 immunity and potential therapeutic targets for the treatment of asthma," Curr. Opin. Allergy Clin. Immunol., Feb. 2011, pp. 39-45, vol. 11(1) [abstract only].
Kaimal et al., "ToppCluster: a multiple gene list feature analyzer for comparative enrichment clustering and network-based dissection of biological systems," Nucleic Acids Res., Jul. 2010, pp. W96-W102, vol. 38(Web Server Issue).
Kariyawasam et al., "Activin and transforming growth factor-B signaling pathways are activated after allergen challenge in mild asthma," J. Allergy Clin. Immunol., Sep. 2009; pp. 454-462, vol. 124(3).
Kong et al., "Micm12NA-375 inhibits tumour growth and metastasis in oesophageal squamous cellcatcinoma trough repressing insulin-like growth factor I receptor," (iut., Jan. 2012, pp. 33-42, vol. 61(1) [abstract only].
Konikoff et al., "A randomized, double-blind, placebo-controlled trial of fluticasone propionate for pediatric eosinophilic esophagitis," Gastroenterology, Nov. 2006, pp. 1381-1391, vol. 131(5).
Kouro et al., "IL-5- and eosinophil-mediated inflammation: from discovery to therapy," Int. Immunol., Dec. 2009, pp. 1303-1309, vol. 21(12).
Krichevsky et al., "miR-21: a small multi-faceted RNA," J. Cell. Mol. Med., Jan. 2009, pp. 39-53, vol. 13(1).
Kriitzfeldt et al., "Silencing of microRNAs in vivo with 'antagomirs'," Nature, Dec. 1, 2005, pp. 685-689, vol. 438(7068) [abstract only].
Kumar et al., "Let-7 microRNA-mediated regulation of IL-13 and allergic airway inflammation," J. Allergy Clin. Immunol., Nov. 2011, pp. 1077-1085.e10, vol. 128(5).
Kuperman et al., "Direct effects of interleukin-13 on epithelial cells cause airway hyperreactivity and mucus overproduction in asthma," Nat. Med., Aug. 2002, pp. 885-889, vol. 8(8).
Laprise et al., "Functional classes of bronchial mucosa genes that are differentially expressed in asthma," BMC Genomics, Mar. 23, 2004, p. 21 (10 pgs.), vol. 5(1).
Lavigne et al., "Human bronchial epithelial cells express and secrete MMP-12," Biochem. Biophys. Res. Commun., Nov. 12, 2004, pp. 534-546, vol. 324(2) [abstract only].
Lee et al., "ERK1/2 mitogen-activated protein kinase selectively mediates IL-13-induced lung inflammation and remodeling in vivo," J. Clin. Invest., Jan. 2006, pp. 163-173, vol. 116(1).
Lee et al., "Interleukin-13 induces dramatically different transcriptional programs in three human airway cell types," Am. J. Respir. Cell. Mol. Biol., Oct. 2001, pp. 474-485, vol. 25(4).
Leigh et al., "Type 2 cytokines in the pathogenesis of sustained airway dysfunction and airway remodeling in mice," Am. J. Respir. Crit. Care Med., Apr. 1, 2004, pp. 860-867, vol. 169(7).
Li et al., "Epigenetic silencing of microRNA-375 regulates PDK1 expression in esophageal cancer," Dig. Dis. Sci., Oct. 2011, pp. 2849-2856, vol. 56(10) [abstract only].
Li et al., "miR-223 regulates migration and invasion by targeting Artemin in human esophageal carcinoma," J. Biomed. Sci., Mar. 31, 2011, pp. 24, vol. 18.
Liacouras et al., "Eosinophilic esophagitis: Updted and consensus recommendations for children and adults," J. Allergy Clin. Immunol., Jul. 2011, pp. 3-20, vol. 128.
Liacouras et al., "Summary of the First International Gastrointestinal Eosinophil Research Symposium," J. Pediatr. Gastroenterol. Nutr., 2007, pp. 370-391, vol. 45.

Lim et al., "Epigenetic regulation of the IL-13-induced human eotaxin-3 gene by CREB-binding protein-mediated histone 3 acetylation," J. Biol. Chem., Apr. 15, 2011, pp. 13193-13204, vol. 286(15).
Lin et al., "MiR-142-3p as a potential prognostic biomarker for esophageal squamous cell carcinoma," J. Surg. Oncol., Feb. 2012, pp. 175-182, vol. 105(2) [abstract only].
Liu et al., "Role of microRNA let-7 and effect to HMGA2 in esophageal squamous cell carcinoma," Mol. Biol. Rep., Feb. 2012, pp. 1239-1246, vol. 39(2) [abstract only].
Livak et al., "Analysis of relative gene expression data using real-time quantitative PCR and the 2(-Delta Delta C(T)) Method," Method, Dec. 2001, pp. 402-408, vol. 25(4) [abstract only].
Lo et al., "Identification of a novel mouse p53 target gene DDA3," Oncogene, Dec. 16, 1999, pp. 7765-7774, vol. 18(54).
Long et al., "Disruption of the NAD(P)H:Quinone oxidoreductase 1 (NQO1) gene in mice causes myelogenous hyperplasia," Cancer Res., Jun. 1, 2002, pp. 3030-3036, vol. 62(11).
Lu et al., "Function of miR-146a in controlling Treg cell-mediated regulation of Th1 responses," Cell., Sep. 17, 2010, pp. 914-929, vol. 142(6).
Lu et al., "MicroRNA profiling in mucosal biopsies of eosinophilic esophagitis patients pre and post treatment with steroids and relationship with mRNA targets," PLoS One, Jul. 16, 2012, p. e40676 (11 pgs.), vol. 7(7).
Lu et al., "MicroRNA-21 is Up-Regulated in Allergic Airway Inflammation and Regulates IL-12p35 Expression," J. Immunol., Apr. 15, 2009, pp. 4994-5002, vol. 182(8).
Lu et al., "MicroRNA-21 limits in vivo immune response-mediated activation of the IL-12/IFN-gamma pathway, Th1 polarization, and the severity of delayed-type hypersensitivity," J. Immunol., Sep. 15, 2011, pp. 3362-3373, vol. 187(16).
Lu et al., "MicroRNA signature in patients with eosinophilic esophagitis, reversibility with glucocorticoids, and assessment as disease biomarkers," J. Allergy Clin. Immunol., Apr. 2012, pp. 1064-1075.e9, vol. 129(4).
Lu et al., "miR-223 Deficiency Increases Eosinophil Progenitor Proliferation," J. Immunol., Feb. 15, 2013, pp. 1576-1582, vol. 190(4).
Lu et al., "Targeted ablation of miR-21 decreases murine eosinophil progenitor cell growth," PLoS One, Mar. 22, 2013, p. e59397, vol. 8(3).
Lu et al: "MiR-375 is downregulated in epithelial cells after IL-13 stimulation and regulates an IL-13-induced epithelial transcriptome", Mucosal Immunology, 5(4):388-396 (2012).
Lu et al: "Diagnostic, functional, and therapeutic roles of microRNA in allergic diseases", Journal of Allergy and Clinical Immunology, 132(1):3-13 (2013).
Lucendo et al., "Treatment with topical steroids down regulates IL-5, eotaxin-1/CCL11, and eotaxin-3/CCL26 gene expression in eosinophilic esophagitis," Am. J. Gastroenterol., Sep. 2008, pp. 2184-2193, vol. 103(9).
Martinez-Nunez et al., "The interleukin 13 (IL-13) pathway in human macrophages is modulated by microRNA-155 via direct targeting of interleukin 13 receptor alpha1 (IL13Ralpha1)," J. Biol. Chem., Jan. 21, 2011, pp. 1786-1794, vol. 286(3).
Matsushima et al., "MicroRNAs and esophageal squamous cell carcinoma," Digestion, 2010, pp. 138-144, vol. 82(3).
Mattes et al., "Antagonism of microRNA-126 suppresses the effector function of TH2 cells and the development of allergic airways disease," Proc. Natl. Acad. Sci. USA, Nov. 3, 2009, pp. 18704-18709, vol. 106(44).
Mayoral et al., "MicroRNA-221-222 Regulate the Cell Cycle in Mast Cells," J. Immunol., Jan. 1, 2009, pp. 433-445, vol. 182(1).
Medina et al., "OncomiR addiction in an in vivo model of microRNA-21-induced pre-B-cell lymphoma," Nature, Sep. 2, 2010, pp. 86-90, vol. 467(7311) [abstract only].
Menard-Katcher et al: "MicroRNAs are altered in Eosinophilic Esophagitis", Gastroenterology, 142(5) S440 (2012).
Mishra et al., "An etiological role for aeroallergens and eosinophils in experimental esophagitis," J. Clin. Invest., Jan. 2001, pp. 83-90, vol. 107(1).

(56) References Cited

OTHER PUBLICATIONS

Mishra et al., "Esophageal remodeling develops as a consequence of tissue specific IL-5-induced eosinophilia," Jan. 2008, pp. 204-214, vol. 134(1).
Mitchell et al., "Circulating microRNAs as stable blood-based markers for cancer detection," Proc. Natl. Acad. Sci. USA, Jul. 29, 2008, pp. 10513-10518, vol. 105(30).
Mori et al., "Identification of the human eosinophil lineage-committed progenitor: revision of phenotypic definition of the human common myeloid progenitor.," J. Exp. Med., Jan. 19, 2006, pp. 183-193, vol. 206(1).
Mukhopadhyay et al., "Matrix metalloproteinase-12 is a therapeutic target for asthma in children and young adults," J. Allergy Clin. Immunol., Jul. 2010, pp. 70-76, vol. 126(1).
Mulder et al., "Understanding eosinophilic esophagitis: the cellular and molecular mechanisms of an emerging disease," Mucosal. Immunol., Mar. 2011, pp. 139-147, vol. 4(2).
Mus musculus TaqMan probe Mm00446968_ml for hypoxanthine guanine phosphoribosyl transferase (Hprt).
Mus musculus TaqMan probe Mm01216172_ml for chemokine (C-C motif) receptor 3 (Ccr3).
Navarro et al., "Small RNAs guide hematopoietic cell differentiation and function," J. Immunol., Jun. 1, 2010, pp. 59395947, vol. 184(11).
Papagiannakopoulos et al., "MicroRNA-21 targets a network of key tumor-suppressive pathways in glioblastoma cells," Cancer Res., Oct. 1, 2008, pp. 8164-8172, vol. 68(19).
Petriv et al., "Comprehensive microRNA expression profiling of the hematopoietic hierarchy," Pro. Natl. Acad. Sci. USA, Aug. 31, 2010, pp. 15443-15448, vol. 107(35).
Polikepahad et al., "Proinflammatory Role for let-7 MicroRNAS in Experimental Asthma," J. Biol. Chem., Sep. 24, 2010, pp. 30139-30149, vol. 285(39).
Pouladi et al., "Interleukin-13-dependent expression of matrix metalloproteinase-12 is required for the development of airway eosinophilia in mice," Am. J. Respir. Cell. Mol. Biol., Jan. 2004, pp. 84-90, vol. 30(1).
Rabinowits et al., "Exosomal microRNA: a diagnostic marker for lung cancer," Clin. Lung Cancer., Jan. 2009, pp. 42-46, vol. 10(1) [abstract only].
Ramirez et al., "Immortalization of human bronchial epithelial cells in the absence of viral oncoproteins," Cancer Res., Dec. 15, 2004, pp. 9027-9034, vol. 64(24).
Rosas et al., "IL-5-mediated eosinophil survival requires inhibition of GSK-3 and correlates with B-catenin relocalization.," J. Leukoc. Biol., Jul. 2006, pp. 186-195, vol. 80(1).
Rothenberg et al., "Common variants at 5q22 associate with pediatric eosinophilic esophagitis," Nat. Genet., Apr. 2010, pp. 289-291, vol. 42(4).
Rothenberg et al., "The eosinophil," Annu. Rev. Immunol., 2006, pp. 147-174, vol. 24.
Rothenberg, "Biology and treatment of eosinophilic esophagitis," Gastroenterology, Oct. 2009, pp. 1238-1249, vol. 137(4).
Saini et al., "Annotation of mammalian primary microRNAs," BMC Geonomics, Nov. 27, 2008, p. 564, vol. 9.
Sato et al., "MicroRNAs and epigenetics," Febs. J., May 2011, pp. 1598-1609, vol. 278(10).
Sayed et al., "MicroRNAs in development and disease," Physiol. Rev., Jul. 2011, pp. 827-887, vol. 91(3).
Schoneberg et. al., "Structural basis of G protein-coupled receptor function," Mol. Cell. Endocrinol., May 1999, pp. 181-193, vol. 151(1-2).
Sexton, "Recent advances in our understanding of peptide hormone receptors and RAMPS," Curr. Opin. Drug Discov. Devel., Sep. 1999, pp. 440-448, vol. 2(5).
Shen et al., "Plasma microRNAs as potential biomarkers for non-small-cell lung cancer," Lab. Invest., Apr. 2011, pp. 579-587, vol. 91(4).
Sheng et al., "The MUC13 cell-surface mucin protects against intestinal inflammation by inhibiting epithelial cell apoptosis," Gut, Dec. 2011, pp. 1661-1670, vol. 60(12) [abstract only].
Sherrill et al., "Genetic dissection of eosinophilic esophagitis provides insight into disease pathogenesis and treatment strategies," J. Allergy Clin. Immunol., Jul. 2011, pp. 23-32, vol. 128(1).
Sherrill et al., "Variants of thymic stromal lymphopoietin and its receptor associate with eosinophilic esophagitis," J. Allergy Clin. Immunol., Jul. 2010, pp. 160-165.e3, vol. 126(1).
Shinkai et al., "A novel human Cc chemokine, eotaxin-3, which is expressed in IL-4-stimulated vascular endothelial cells, exhibits potent activity toward eosinophils," J. Immunol., Aug. 1, 1999, pp. 1602-1610, vol. 163(3).
Smith et al., "MicroRNAs, development of Barrett's esophagus, and progression to esophageal adenocarcinoma," World J. Gastroenterol, Feb. 7, 2010, pp. 531-537, vol. 16(5).
Smith' "Insulin-like growth factor-I regulation of immune function: a potential therapeutic target in autoimmune diseases?," Pharmacal. Rev., Jun. 2010, pp. 199-236, vol. 62(2).
Sonkoly et al., "MicroRNAs: novel regulators involved in the pathogenesis of psoriasis?," PLoS One, Jul. 1, 2007, p. e610, vol. 2(7).
Sonkoly et al., "MiR-155 is overexpressed in patients with atopic dermatitis and modulates T-cell proliferative responses by targeting cytotoxic T lymphocyte-associated antigen 4," J. Allergy Clin. Immunol., Sep. 2010, pp. 581-589, vol. 126(3).
Stansfield et al., "Periostin is a novel factor in cardiac remodeling after experimental and clinical unloading of the failing heart," Ann. Thorac. Surg., Dec. 2009, pp. 1916-1921, vol. 88(6).
Straumann et al., "Eosinophilic esophagitis: Escalating epidemiology?," J. Allergy Clin. Immunol., 2005, pp. 418-419, vol. 115.
Straumann et al., "Idiopathic eosinophilic esophagitis is associated with a T(H)2-type allergic inflammatory response," J. Allergy Clin. Immunol., Dec. 2001, pp. 954-961, vol. 108(6).
Suire et al., "p84, a New GRy-Activated Regulatory Subunit of the Type IB Phosphoinositide 3-Kinase p110y," Curr. Biol., Mar. 29, 2005, pp. 566-570, vol. 15(6).
Tan et al., "HYAL1 overexpression is correlated with the malignant behavior of human breast cancer," Int. J. Cancer, Mar. 15, 2011, pp. 1303-1315, vol. 128(6).
Tian et al., "Visualizing of the cellular uptake and intracellular trafficking of exosomes by live-cell microscopy," J. Cell. Biochem., Oct. 1, 2010, pp. 488-496, vol. 111(2) [abstract only].
Trapnell et al., "TopHat: discovering splice junctions with RNA-Seq," Bioinformatics, May 1, 2009, pp. 1105-1111, vol. 5 2(9).
Trapnell et al., "Transcript assembly and quantification by RNA-Seq reveals unannotated transcripts and isoform switching during cell differentiation," Nat. Biotechnol., May 2010, pp. 511-1, vol. 28(5).
Tsang et al., "Oncofetal H19-derived miR-675 regulates tumor suppressor RB in human colorectal cancer," Carcmogenesis, Mar. 2010, pp. 350-358, vol. 31(3).
Tsuchiya et al., "MicroRNA-210 regulates cancer cell proliferation through targeting fibroblast growth factor receptor-like 1 (FGFRL1)," J. Biol. Chem., Jan 7, 2011, pp. 420-428, vol. 286(1).
Tsukamoto et al., "MicroRNA-375 is downregulated in gastric carcinomas and regulates cell survival by targeting PDK1 and 14-3-g," Cancer Res., Mar. 15, 2010, pp. 2339-2349, vol. 70(6).
Valadi et al., "Exosome-mediated transfer of mRNAs and microRNAs is a novel mechanism of genetic exchange between cells," Nat. Cell Biol., Jun. 2007, pp. 654-659, vol. 9(6) [abstract only].
van Rooij et al., "Developing MicroRNA Therapeutics," Circ. Res., Feb. 3, 2012, pp. 496-507, vol. 110.
Velu et al., "Gfi1 regulates miR-21 and miR-196b to control myelopoiesis," Blood, May 7, 2009, pp. 4720-4728, vol. 113(19).
Venge, "The eosinophil and airway remodelling in asthma," Clin. Respir. J., May 2010, pp. 15-19, vol. 4 (Suppl. 1) [abstract only].
Wan et al., "Foxa2 regulates alveolarization and goblet cell hyperplasia," Development, Feb. 2004, pp. 953-964, vol. 131(4).
Wang et al., "Differential functions of growth factor receptor-bound protein 7 (GRB7) and its variant GRB7v in ovarian carcmogenesis," Clin. Cancer Res., May 1, 2010, pp. 2529-2539, vol. 16(9).

(56) References Cited

OTHER PUBLICATIONS

Wills-Karp, "Interleukin-13 in asthma pathogenesis," Immunol. Rev., Dec. 2004, pp. 175-190, vol. 202 [abstract only].

Winter et al., "Many roads to maturity: microRNA biogenesis pathways and their regulation," Nat. Cell. Biol., Mar. 2009, pp. 228-234, vol. 11(3) [abstract only].

Wong et al., "MicroRNA-21* regulates the prosurvival effect of GM-CSF on human eosinophils," Immunobiology, Feb. 2013, pp. 255-262, vol. 218(2) [abstract only].

Woodruff et al., "Genome-wide profiling identifies epithelial cell genes associated with asthma and with treatment response to corticosteroids," Proc. Natl. Acad. Sci. USA., Oct. 2, 2007, pp. 15858-15863, vol. 104(40).

Wu et al., "MicroRNAs are differentially expressed in ulcerative colitis and alter expression of macrophage inflammatory peptide-2 alpha," Gastroenterology, Nov. 2008, pp. 1624-1635.e24, vol. 135(5).

Xiang et al., "Wound repair and proliferation of bronchial epithelial cells regulated by CTNNAL1," J. Cell, Biochem., Feb. 15, 2008, pp. 920-930, vol. 103.

Xing et al., "Protease phenotype of constitutive connective tissue and of induced mucosal mast cells in mice is regulated by the tissue," Proc. Natl. Acad. Sci. USA, Aug. 23, 2011, pp. 14210-14215, vol. 108(34).

Yang et al., "Inhibition of arginase I activity by RNA interference attenuates IL-13-induced airways hyperresponsiveness," J. Immunol, Oct. 15, 2006, pp. 5595-5603, vol. 177(8).

Yee' "Insulin-like growth factor receptor inhibitors: baby or the bathwater?," J. Natl. Cancer Inst., Jul. 3, 2012, pp. 975- 981,vol. 104(13).

Yi et al., "A skin microRNA promotes differentiation by repressing 'sternness'," Nature, Mar. 13, 2008, pp. 225-229, vol. 452(7184) [abstract only].

Yin et al., "Targeting the insulin-like growth factor-1 receptor by picropodophyllin as a treatment option for glioblastoma," Neuro Oncol., Jan. 2010, pp. 19-27, vol. 12(1).

Yuan et al., "MicroRNA-203 inhibits cell proliferation by repressing ANp63 expression in human esophageal squamous cell carcinoma," BMC Cancer, Feb. 7, 2011, p. 57, vol. 11.

Zahm et al., "Circulating microRNA is a biomarker of pediatric Crohn disease," J. Pediatr. Gastroenterol. Nutr., Jul. 2011, pp. 26-33, vol. 53(1).

Zhen et al., "IL-13 and epidermal growth factor receptor have critical but distinct roles in epithelial cell mucin production," Am. J. Respir. Cell. Mol. Biol., Feb. 2007, pp. 244-254, vol. 36(2).

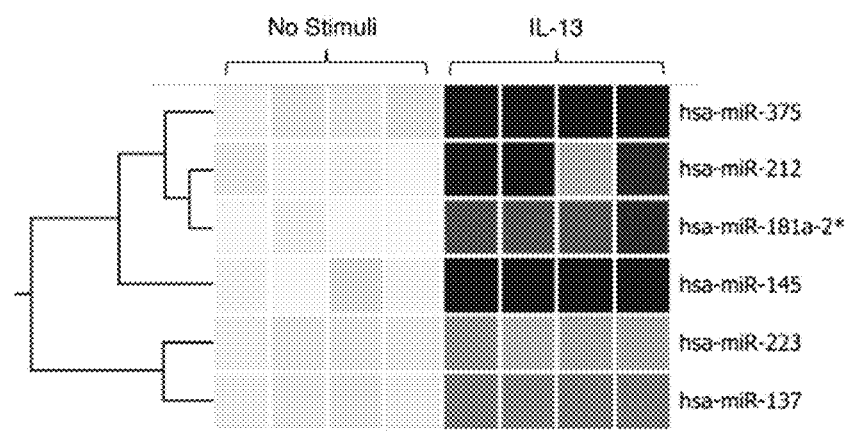
FIG. 25A
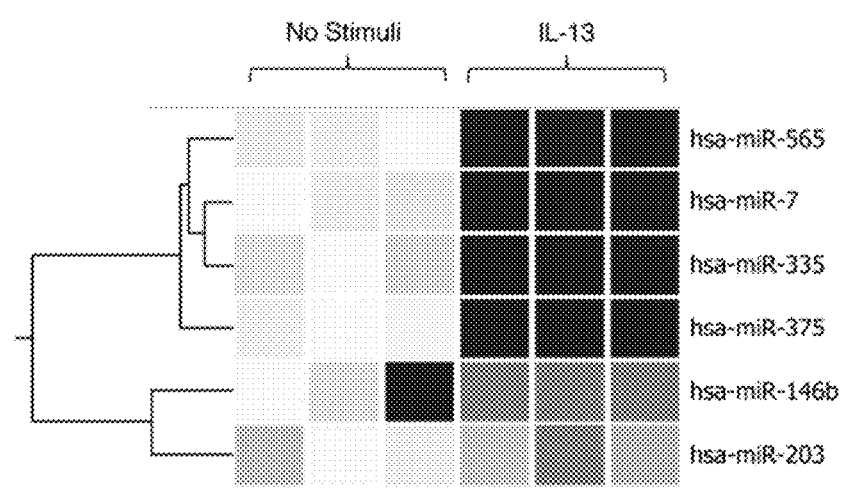
FIG. 25B

ESOPHAGEAL MICRORNA EXPRESSION PROFILES IN EOSINOPHILIC ESOPHAGITIS

CROSS REFERENCE TO RELATED APPLICATION

The present application is a Continuation Application of U.S. patent application Ser. No. 14/380,672, filed Aug. 22, 2014, which is the National Stage of International Application Ser. No. PCT/US2013/027503 filed Feb. 22, 2013, which claims the benefit of priority under 35 U.S.C. §119(e) priority to U.S. Provisional Application No.: 61/602,897 filed Feb. 24, 2012, and which is incorporated by reference in its entirety.

STATEMENT REGARDING FEDERALLY-SPONSORED RESEARCH

This invention was made with U.S. Government support under HL104892, DK076893, AI083450, GM063483, HD046387, AI070235, and DK078392 awarded by the National Institutes of Health. The U.S. Government has certain rights in the invention.

FIELD OF THE INVENTION

The invention disclosed herein generally relates to diagnosis, treatment, and/or management of eosinophilic esophagitis, asthma, and/or allergic diseases, disorders, and/or conditions arising therefrom and/or related thereto.

BACKGROUND

All publications mentioned herein are incorporated by reference to the same extent as if each individual publication or patent application was specifically and individually indicated to be incorporated by reference. The following description includes information that can be useful in understanding the present subject matter. It is not an admission that any of the information provided herein is prior art or relevant to the presently claimed subject matter, or that any publication specifically or implicitly referenced is prior art.

Eosinophilic esophagitis (EE, also abbreviated EoE in some publications) is an emerging worldwide disease characterized by marked eosinophil infiltration of the esophageal mucosal epithelium (>15 eosinophils/high power field (hpf)) that is refractory to acid suppressive therapy and is associated with chronic symptoms from childhood into adulthood (see, e.g., Furuta, G. et al. *Gastroenterology* 133:1342-63 (2007); Assa'ad, A. et al. *J Allergy Clin. Immunol.* 119:731-8 (2007); Straumann, A. and Simon, H. *J Allergy Clin. Immunol.* 115:418-9 (2005); Liacouras, C. et al. *J. Allergy Clin. Immunol.* 128:3-20 (2011)). First described in the late 1970s, the incidence and prevalence of EE has been increasing, and EE is now a global disease reported in every continent except Africa (see, e.g., Liacouras, C. et al. *J. Allergy Clin. Immunol.* 128:3-20 (2011)).

EE symptoms mimic gastroesophageal reflux disease (GERD) and can vary with age. Patients with EE can have gastrointestinal complains that typically include, but are not limited to, failure to thrive, vomiting, abdominal pain, dysphagia, and food impactions (see, e.g., Furuta, G. et al. *Gastroenterology* 133:1342-63 (2007); Liacouras, C. et al. *J Pediatr. Gastroenterol. Nutr.* 45:370-91 (2007)).

EE diagnosis involves endoscopy, which is an invasive and inconvenient procedure. The endoscopy procedure is then commonly followed by biopsy analysis. EE provides an opportunity to closely study human inflammatory diseases, as obtaining tissue specimens via endoscopy is routine standard-of-care, and the biopsy material is amenable to molecular analysis (see, e.g., Liacouras, C. et al. *J. Allergy Immunol.* 128:3-20 (2011); Abonia, J. et al. *J. Allergy Clin. Immunol.* 126:140-9 (2010)).

SUMMARY

Embodiments of the invention encompass methods of treating a patient with eosinophilic esophagitis (EE), including obtaining a sample from a patient, analyzing the sample to determine a level of one or more miRNAs associated with EE, determining whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE, and treating the patient with an appropriate therapeutic strategy based upon the diagnosis.

In some embodiments of the methods, the one or more miRNAs associated with EE can include, for example, miR-886-5p, miR-886-3p, miR-222*, miR-7, miR-29b, miR-642, miR-339-5p, miR-21, miR-21*, miR-142-5p, miR-146a, miR-146b, miR-142-3p, miR-132, miR-212, miR-592, miR-92a-1*, miR-223*, miR-223, miR-801, miR-106b*, miR-375, miR-211, miR-210, miR-365, miR-203, miR-193a-5p, miR-193b, miR-193a-3p, let-7c, miR-144*, or miR-30a-3p. In some embodiments, the one or more miRNAs associated with EE can include, for example, miR-21, miR-223, miR-375, miR-142-3p, miR-146a, or miR-146b. In some embodiments, the one or more miRNAs associated with EE can include, for example, miR-21, miR-223, or miR-375.

In some embodiments, the determination of whether the level(s) of the one or more miRNAs associated with EE are elevated or reduced relative to a level of the one or more miRNAs measured in a normal individual can be combined with a determination of a level(s) of one or more additional biomarkers associated with EE. In some embodiments, the one or more additional biomarkers associated with EE can include, for example, an mRNA biomarker. In some embodiments, the one or more additional biomarkers associated with EE can include, for example, eotaxin-3.

In some embodiments, the sample can be, for example, an esophageal tissue sample. In some embodiments, the sample can be, for example, a plasma or scrum sample. In some embodiments, the sample can be, for example, a buccal sample, an oral swish, or saliva.

In some embodiments, the appropriate therapeutic strategy for a patient diagnosed with EE can include, for example, allergen removal, steroid treatment, dietary management, proton pump inhibitor (PPI) therapy, administration of one or more topical glucocorticoids, humanized antibodies against one or more relevant cytokines and/or mediators, one or more small molecule inhibitors of an eosinophil and/or allergic disease activation pathway, one or more small molecule inhibitors capable of modulating miRNA levels and/or as severing as stem-loop processing inhibitors, and/or any combination thereof. In some embodiments, the topical glucocorticoid can include, for example, fluticasone, budesonide, and/or ciclesonide. In some embodiments, the humanized antibody against a relevant cytokine or mediator can include, for example, an antibody against eotaxin-1, eotaxin-3, IL-13, IL-5, IL-5Rα, CD49D, SIGLEC-8, IgE, CD300A, TSLP, and/or IL-33. In some embodiments, the small molecule inhibitor can include, for example, a notch-signaling inhibitor or an inhibitor or antagonist of CCR3, CCL11, VLA4, CRTH2, prostaglandin D2, histamine H4 receptor, IL-13, IL-4, and/or the common β chain.

In some embodiments, the appropriate therapeutic strategy includes using any of the one or more miRNA(s) associated with EE found to be elevated relative to the level(s) of the one or more miRNAs measured in a normal individual or using one or more corresponding modified miRNA(s) as a therapeutic target or agent. In some embodiments, the appropriate therapeutic strategy includes administering to the patient one or more agents such as, for example, an anti-miRNA oligonucleotide (antagomir), an antisense oligonucleotide, a locked nucleic acid, an RNA competitive inhibitor or decoy, and/or a viral vector expressing one or more miRNA genes, and the like. In some embodiments, the antagomir can be directed against a miRNA found to be elevated relative to the level(s) of the one or more miRNAs measured in a normal individual. In some embodiments, the antagomir against the up-regulated miRNA can be, for example, a miR-21, miR-223, miR-146a, and/or miR-146b antagomir, and the like. In some embodiments, the competitive inhibitor against the elevated miRNA can be, for example, an IGF1 or IGF1R inhibitor, and the like. In some embodiments, the IGF1R inhibitor can be, for example, NVP-AEW541 and/or pricopodophyllin, and the like. In some embodiments, the viral vector expressing one or more miRNA genes can be, for example, a lentiviral vector, an adenoviral vector, and/or an adeno-associated virus, and the like.

Some embodiments of the methods further include a determination of eosinophilic esophagitis or chronic esophagitis, wherein the presence of a non-elevated or non-reduced level of one or more miRNAs associated with eosinophilic esophagitis results in the patient being diagnosed with chronic esophagitis. In some embodiments, the appropriate therapeutic strategy can include, for example, antacid administration, H2 agonist administration, and/or PPI therapy.

Some embodiments of the methods further include a determination of active eosinophilic esophagitis or eosinophilic esophagitis in remission, wherein the one or more miRNAs can include, for example, miR-886-5p, miR-886-3p, miR-222*, miR-7, miR-29b, miR-642, miR-339-5p, miR-21, miR-21*, miR-142-5p, miR-146a, miR-146b, miR-142-3p, miR-132, miR-212, miR-592, miR-92a-1*, miR-223*, miR-223, miR-801, miR-106b*, miR-375, miR-211, miR-210, miR-365, miR-203, miR-193a-5p, miR-193b, miR-193a-3p, let-7c, miR-144*, and miR-30a-3p.

Some embodiments of the methods further include a determination of EE disease severity, wherein a highly up-regulated or highly down-regulated level of the one or more miRNAs relative to the level(s) of the one or more miRNAs measured in a normal individual is indicative of a severe case of EE.

In some embodiments, a patient diagnosed with EE can be determined to be compliant with and/or exposed to steroid treatment, wherein an elevated level of miR-675 following treatment indicates that the patient is compliant with and/or exposed to steroid treatment.

In some embodiments, a patient diagnosed with EE and treated with a steroid can be determined to be responsive or non-responsive to steroid treatment, wherein an elevated level of miR-675 following treatment indicates that the patient is responsive to steroid treatment.

In some embodiments, a patient diagnosed with EE can be determined to be likely to be responsive or non-responsive to anti-IL-13 treatment, wherein an elevated level of one or more miRNAs associated with periostin levels indicates that the patient is likely to be responsive to anti-IL-13 treatment. In some embodiments, the one or more miRNAs associated with periostin levels can include, for example, miR-223 and/or miR-375.

Embodiments of the invention are also directed to methods of diagnosing a patient with eosinophilic esophagitis (EE), the methods including obtaining a sample from a patient, analyzing the sample to determine a level of one or more miRNAs associated with EE in adult patients, and determining whether the level of the one or more miRNAs are up-regulated or down-regulated relative to a level of the one or more miRNAs measured in a normal individual, wherein the presence of an elevated or reduced level of one or more miRNAs associated with EE results in the patient being diagnosed with EE.

Embodiments of the invention are also directed to methods of treating a patient with an eosinophilic disorder, the methods including, obtaining a sample from a patient, analyzing the sample to determine a level of one or more miRNAs associated with an eosinophilic disorder, determining whether the level of the one or more miRNAs is up-regulated or down-regulated relative to a level of the one or more miRNAs measured in a normal individual, wherein the presence of an elevated or reduced level of one or more miRNAs associated with an eosinophilic disorder results in the patient being diagnosed with an eosinophilic disorder, and treating the patient with an appropriate therapeutic strategy based upon the diagnosis.

In some embodiments, the eosinophilic disorder can be, for example, an eosinophilic gastrointestinal disorder (EGID). In some embodiments, the eosinophilic disorder can be, for example, asthma. In some embodiments, the one or more miRNAs associated with asthma can be, for example, miR-375. In some embodiments, the sample can include, for example, lung and/or lung epithelial cells.

Embodiments of the invention are also directed to a diagnostic kit, test, or array, including materials for quantification of at least two analytes, wherein the at least two analytes are miRNAs associated with eosinophilic esophagitis (EE).

In some embodiments, the at least two analytes can include, for example, miR-21, miR-223, and miR-375. In some embodiments, the at least two analytes can include, for example, miR-886-5p, miR-886-3p, miR-222*, miR-7, miR-29b, miR-642, miR-339-5p, miR-21, miR-21*, miR-142-5p, miR-146a, miR-146b, miR-142-3p, miR-132, miR-212, miR-592, miR-92a-1*, miR-223*, miR-223, miR-801, miR-106b*, miR-375, miR-211, miR-210, miR-365, miR-203, miR-193a-5p, miR-193b, miR-193a-3p, let-7c, miR-144*, and miR-30a-3p. In some embodiments, the at least two analytes can include, for example, miR-21, miR-223, miR-375, miR-142-3p, miR-146a, and miR-146b. In some embodiments, the at least two analytes can include, for example, miR-21, miR-223, miR-375, miR-142-3p, miR-146a, and miR-146b.

In some embodiments, the at least two analytes can include all of miR-21, miR-223, and miR-375. In some embodiments, the at least two analytes can include all of miR-21, miR-223, miR-375, miR-142-3p, miR-146a, and miR-146b. In some embodiments, the at least two analytes can include all of miR-886-5p, miR-886-3p, miR-222*, miR-7, miR-29b, miR-642, miR-339-5p, miR-21, miR-21*, miR-142-5p, miR-146a, miR-146b, miR-142-3p, miR-132, miR-212, miR-592, miR-92a-1*, miR-223*, miR-223, miR-801, miR-106b*, miR-375, miR-211, miR-210, miR-365, miR-203, miR-193a-5p, miR-193b, miR-193a-3p, let-7c, miR-144*, and miR-30a-3p.

In some embodiments, the diagnostic kit, test, or array can include a gene chip. In some embodiments, the gene chip includes a low density array.

In some embodiments, the diagnostic kit, test, or array can include a surface with a DNA array.

BRIEF DESCRIPTION OF THE DRAWINGS

Those of skill in the art will understand that the drawings, described below, are for illustrative purposes only. The drawings are not intended to limit the scope of the present teachings in any way.

FIG. 2F illustrates the Pearson correlation of miRNA expression levels between microarray data and qRT-PCR validation. N=7-17 patients per group; data are represented as mean±the standard error of the mean (SEM).

FIG. 3A presents a heatmap showing the expression levels of 32 differentially expressed miRNAs in EE patients compared to chronic esophagitis patients and EE patients in remission after glucocorticoid therapy. FIG. 3B illustrates the correlation of EE signature genes with miR-21. FIG. 3C illustrates the correlation of EE signature genes with miR-223. The significance of the correlation was plotted as the negative log of p value for each gene. The dashed line represents significance level after false discovery rate correction.

FIG. 4A presents a heatmap showing the expression level of miR-675, which is the only miRNA differentially regulated in EE patients that responded to glucocorticoid therapy compared to normal controls, chronic esophagitis patients, and EE patients. FIG. 4B illustrates the relative expression level of miR-675 in normal controls, EE patients, fluticasone propionate responder patients, and fluticasone propionate non-responder patients. Relative expression levels were determined by qRT-PCR normalized to U6. N=7-11 patients per group; data are represented as mean±SEM.

FIG. 5A illustrates the identification of the pri-miR-21 region in the RNA-Seq analysis. The normalized coverage tracks for the mRNA-seq are displayed, along with the spliced reads that are present in exons of VMP1. The lack of spliced reads present between the regions outside of the exons of VMP1 indicates that it is a portion of pri-miR-21. The regions annotated as "exon" or "intron" are not necessarily true exons and introns of a gene but regions that showed significant expression patterns similar to that of a gene's exons and introns. They were annotated as such to facilitate the identification of the region to use for the correlation analysis. FIG. 5B illustrates the identification of the pri-miR-223 region in the RNA-Seq analysis. The normalized coverage tracks for the mRNA-seq are displayed, but there are no reads spanning junctions because there are no splicing events present in this region. The regions annotated as "exon" are not necessarily true exons of a gene but regions that showed significant expression patterns similar to that of a gene's exons. They were annotated as such to facilitate the identification of the region to use for the correlation analysis.

FIG. 6A illustrates the abstracted interactions between miR-21 and miR-223 co-regulated target genes. FIG. 6B illustrates the miR-21 targets that are significantly correlated with miR-21 expression or in the EE transcriptome; targets are shown as hexagons. For example, miR-21 co-regulated targets are significantly enriched in genes that regulate interleukin production. FIG. 6C illustrates the Pearson correlation of miR-21 and IL-12p35 expression levels in esophageal biopsies from EE patients.

FIG. 11A illustrates the purity of cultured eosinophils at day 14; eosinophils are identified as $CCR3^+$ $Siglec-F^+$ cells. FIG. 11B illustrates miR-21 expression levels during the eosinophil differentiation culture, as determined by quantitative polymerase chain reaction (qPCR) normalized to U6. N=3 per group; data are represented as mean±SEM.

FIG. 12A illustrates the total cell number of eosinophil cultures; FIG. 12B illustrates the total number of neutrophil cultures derived from miR-21$^{+/+}$ and miR-21$^{-/-}$ mice. N=6 per group; data are represented as mean±SEM. FIG. 12C displays the morphology of miR-21$^{+/+}$ and miR-21$^{-/-}$ cultured eosinophils at day 12, as determined by Diff-Quik (Fisher Scientific, Pittsburgh, Pa.) staining.

FIG. 14A illustrates blood eosinophil percentage from miR-21$^{+/+}$ and miR-21$^{-/-}$ mice, as determined by FACS staining for CCR3$^+$ Siglec-F$^+$ cells; n=9-10 mice per group. FIG. 14B illustrates bone marrow eosinophil colony forming unit (CFU-Eos), and FIG. 14C illustrates neutrophil colony forming unit (CFU-G) capacity from miR-21$^{+/+}$ and miR-21$^{-/-}$ mice. N=4 per group; data are represented as mean±SEM.

FIG. 15A presents a heatmap of differentially regulated genes at day 8 of the eosinophil differentiation culture. FIG. 15B presents a heatmap of differentially regulated genes at day 12 of the eosinophil differentiation culture. FIG. 15C depicts the quantitative RT-PCR verification of a selected set of differentially expressed genes between miR-21$^{+/+}$ and miR-21$^{-/-}$ eosinophil progenitor cultures. FIG. 15D illustrates a functional enrichment analysis of differentially regulated genes in the eosinophil progenitor cultures at day 12. The networks are shown as Cytoscape (open source software) graph networks generated from ToppCluster (Cincinnati Children's Hospital Medical Center) network analysis.

FIG. 17A presents a schematic of the ex vivo bone marrow-derived eosinophil culture. FIG. 17B illustrates the purity of cultured eosinophils after 14 days; eosinophils are identified as CCR3$^+$ Siglec-F$^+$ cells. FIG. 17C illustrates miR-223 expression levels during the eosinophil differentiation culture. N=3 per group; data are represented as mean±SEM.

FIG. 18A illustrates the total cell number of eosinophils in cultures derived from miR-223$^{+/+}$ and miR-223$^{-/-}$ mice, as determined by cell counting using a hemacytometer. N=6 per group; data are represented as mean±SEM. FIG. 18B illustrates the morphology of miR-223$^{+/+}$ and miR-223$^{-/-}$ eosinophil progenitor culture at day 8, 10, and 12, as determined by modified Giemsa (Diff-Quik) staining. FIG. 18C illustrates the morphology of miR-223$^{+/+}$ and miR-223$^{-/-}$ cultured eosinophils at day 14, as determined by Diff-Quik (Fisher Scientific) staining.

FIG. 20A displays data for bone marrow-derived eosinophils from miR-223$^{+/+}$ and miR-223$^{-/-}$ mice; eosinophils were treated with 2 µm picropodophyllin (PPP, an IGF1R inhibitor) or an equivalent volume of dimethyl sulfoxide (DMSO). Growth was measured by cell counting using a hemacytometer. FIG. 20B presents a western blot showing levels of IGF1R expression in miR-223$^{+/+}$ and miR-223$^{-/-}$ cells after 2-day treatment with PPP. GAPDH was used as a loading control. FIG. 20C presents a dose response study of different concentrations of PPP on the proliferative response of eosinophil cultures derived from miR-223$^{+/+}$ and miR-223$^{-/-}$ mice. N=3 per group; data are represented as mean±SEM.

FIG. 21A displays CCR3 expression at day 8, day 10, and day 12 of the eosinophil progenitor culture in miR-223$^{-/-}$ cultures compared to miR-223$^{+/+}$ cultures, as measured by qPCR normalized to HPRT1. N=3 per group; data are represented as mean±SEM. FIG. 21B displays levels of CCR3 expression during eosinophil differentiation culture, as determined by FACS staining of surface CCR3 and Siglec F levels; mature eosinophils are identified as CCR3$^+$ Siglec-F$^+$ cells.

FIG. 24A depicts the level of mature eosinophils in the blood of miR-223$^{+/+}$ and miR-223$^{-/-}$ mice. Blood eosinophil levels were determined by CCR3 and SiglecF staining. The double positive cells are eosinophils. N=7-8 mice per group. FIG. 24B depicts the eosinophil progenitor levels in the bone marrow of miR-223$^{+/+}$ and miR-223$^{-/-}$ mice. Eosinophil progenitor levels were determined by CD34 and IL5Rα staining. The double positive cells are eosinophil progenitors. N=3-4 mice per group. Data are represented as mean±S.E.M.

FIG. 22A presents a heatmap of differentially regulated genes at day 8 of the eosinophil differentiation culture. FIG. 22B illustrates a functional enrichment analysis of differentially regulated genes in the eosinophil progenitor cultures at day 8. The networks are shown as Cytoscape (open source software) graph networks generated from ToppCluster (Cincinnati Children's Hospital Medical Center) network analysis. FIG. 22C presents a heatmap of differentially regulated genes at day 12 of the eosinophil differentiation culture. FIG. 22D illustrates an analysis of the most significant biological functions represented by the differentially regulated genes between miR-223$^{+/+}$ and miR-223$^{-/-}$ eosinophil progenitor cultures at day 12.

FIGS. 25A-B depict the miRNA expression profile in human esophageal epithelial cells and human bronchial epithelial cells after 24 hours of IL-13 stimulation. FIG. 25A presents a heatmap of 4 down-regulated and 2 up-regulated miRNAs in IL-13-stimulated human esophageal epithelial cells compared to controls. FIG. 25B presents a heatmap of 4 down-regulated and 2 up-regulated miRNAs in IL-13-stimulated human bronchial epithelial cells compared to controls.

FIG. 26C displays a kinetic analysis of miR-375 expression in IL-13-stimulated esophageal epithelial cells. FIG. 26D displays a kinetic analysis of miR-375 expression in IL-13-stimulated normal human bronchial epithelial cells. The relative expression levels were normalized to U6. N=4 per group; data are represented as mean±SEM; NS: not significant.

FIG. 28A displays the miR-375 expression levels in normal controls, EE patients, chronic esophagitis patients, EE patients responsive to glucocorticoid therapy (fluticasone proprionate), EE patients unresponsive to glucocorticoid therapy, and EE patients responsive to diet modification. Expression levels were determined by qPCR normalized to U6. N=8-15 patients per group; data are represented as mean±SEM. FIG. 28B displays the correlation between miR-375 expression and esophageal eosinophil counts. FIG. 28C displays the correlation between miR-375 expression and EE signature genes. The significance of the correlation was plotted as the negative log of p value for each gene. The dashed line represents significance level after false discovery rate correction.

FIG. 30A presents a heatmap showing genes differentially expressed in esophageal epithelial cell line transduced with either a control vector or a pre-miR-375 expression vector, before and after IL-13 stimulation. FIG. 30B displays a functional enrichment analysis of pathways affected by miR-375 under IL-13-stimulated conditions. The networks are shown as Cytoscape (open source software) graph networks generated from ToppCluster (Cincinnati Children's Hospital Medical Center) network analysis.

DETAILED DESCRIPTION OF THE INVENTION

Figure 1:
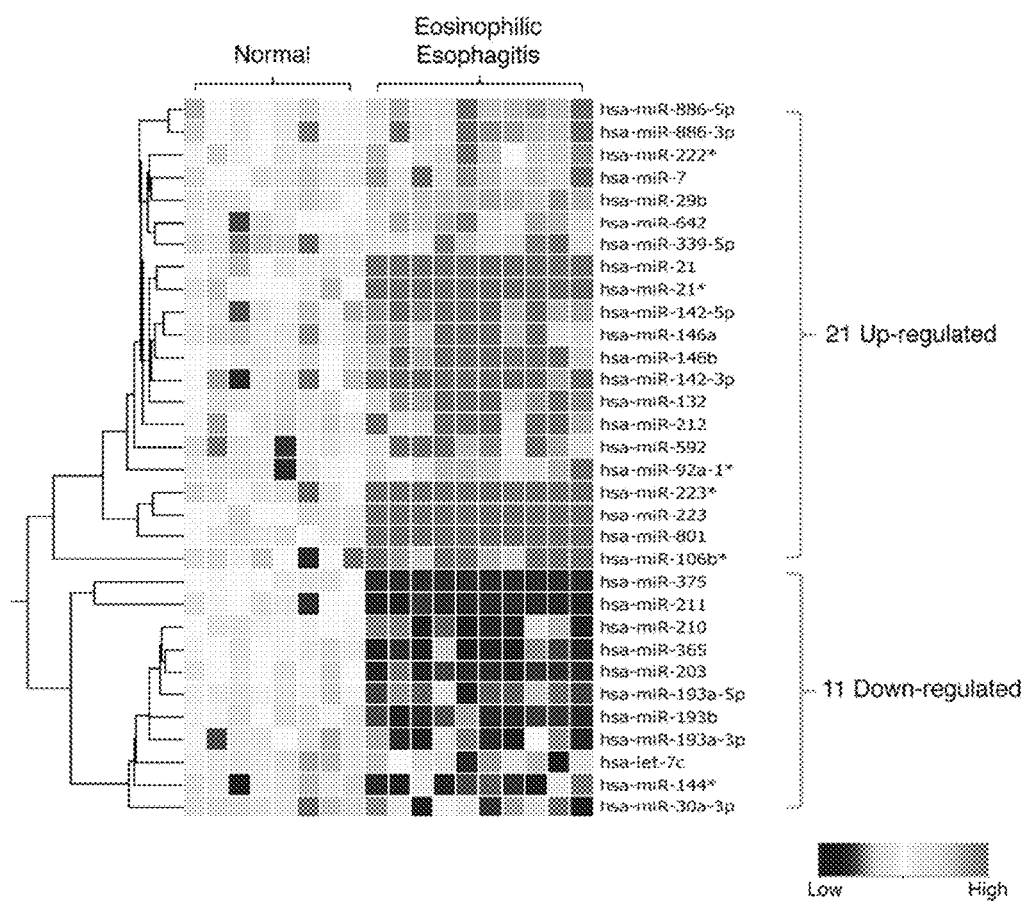
FIG. 1 depicts microRNA (miRNA) expression profiles in normal patients and EE patients. The figure presents a heatmap of 21 up-regulated and 11 down-regulated miRNAs in EE patients compared to normal controls.

All references cited herein are incorporated by reference in their entirety. Also incorporated herein by reference in their entirety include: U.S. Patent Application No. 60/633,909, EOTAXIN-3 IN EOSINOPHILIC ESOPHAGITIS, filed on Dec. 27, 2004; U.S. Pat. No. 8,030,003, DIAGNOSIS OF EOSINOPHILIC ESOPHAGITIS BASED ON PRESENCE OF AN ELEVATED LEVEL OF EOTAXIN-3, issued Oct. 4, 2011 and filed as U.S. patent application Ser. No. 11/721,127 on Jun. 7, 2007; U.S. patent application Ser. No. 12/492,456, EVALUATION OF EOSINOPHILIC ESOPHAGITIS, filed on Jun. 26, 2009; U.S. patent application Ser. No. 12/628,992, IL-13 INDUCED GENE SIGNATURE FOR EOSINOPHILIC ESOPHAGITIS, filed on Dec. 1, 2009; U.S. Provisional Application No. 61/430,453, A STRIKING LOCAL ESOPHAGEAL CYTOKINE EXPRESSION PROFILE IN EOSINOPHILIC ESOPHAGITIS, filed on Jan. 6, 2011; U.S. patent application Ser. No. 13/051,873, METHODS AND COMPOSITIONS FOR MITIGATING EOSINOPHILIC ESOPHAGITIS BY MODULATING LEVELS AND ACTIVITY OF EOTAXIN-3, filed on Mar. 18, 2011; U.S. patent application Ser. No. 13/132,884, DETERMINATION OF EOSINOPHILIC ESOPHAGITIS, filed on Jun. 3, 2011; U.S. Provisional Application No. 61/497,796, NEGATIVE REGULATION OF EOSINOPHIL PRODUCTION BY TOLL-LIKE RECEPTORS, filed on Jun. 16, 2011; U.S. Patent Application No. 61/571,115, DIAGNOSTIC METHODS OF EOSINOPHILIC ESOPHAGITIS, filed on Jun. 21, 2011; U.S. Provisional Application No. 61/500,508, MOLECULAR DIAGNOSTIC PANEL OF EOSINOPHILIC GASTROINTESTINAL DISORDERS, filed on Jun. 23, 2011; U.S. patent application Ser. No. 13/132,295, METHODS OF DETERMINING EFFICACY OF GLUCOCORTICOID TREATMENT OF EOSINOPHILIC ESOPHAGITIS, filed on Aug. 22, 2011; PCT Patent Application No. US2012/020556, ESOPHAGEAL CYTOKINE EXPRESSION PROFILES IN EOSINOPHILIC ESOPHAGITIS, filed on Jan. 6, 2012; U.S. Provisional Application No. 61/602,897, ESOPHAGEAL MICRORNA EXPRESSION PROFILES IN EOSINOPHILIC ESOPHAGITIS, filed on Feb. 24, 2012; PCT Patent Application No. US2012/42985, BLOCKADE OF EOSINOPHIL PRODUCTION BY TOLL-LIKE RECEPTORS, filed on Jun. 18, 2012; PCT Patent Application No. US2012/043640, DIAGNOSTIC METHODS FOR EOSINOPHILIC ESOPHAGITIS, filed on Jun. 21, 2012; and PCT Patent Application No. US2012/044061, MOLECULAR DIAGNOSTIC PANEL OF EOSINOPHILIC GASTROINTESTINAL DISORDERS, filed on Jun. 25, 2012.

Unless otherwise noted, terms are to be understood according to conventional usage by those of ordinary skill in the relevant art.

As used herein, the term "subject" refers to any member of the animal kingdom. In some embodiments, a subject is a human patient.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing or monitoring" with reference to a disease state or condition refers to a method or process of determining if a subject has or does not have a particular disease state or condition or determining the severity or degree of the particular disease state or condition.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present invention to mitigate a disease or a disorder in a host, preferably in a mammalian subject, more preferably in humans. Thus, the term "treatment" can include includes: preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted (see Webster's Ninth Collegiate Dictionary). Rather, as used herein, the term preventing refers to the ability of the skilled artisan to identify a population that is susceptible to disorders, such that administration of the compounds of the present invention can occur prior to onset of a disease. The term does not mean that the disease state must be completely avoided.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

Eosinophilic esophagitis (EE, also referred to as EoE in some publications) is a condition characterized by elevated esophageal levels of eosinophils. EE is considered to be a $T_H2$-associated disease (see, e.g., Blanchard, C. et al. *J. Allergy Clin. Immunol.* 120:1292-300 (2007); Blanchard, C. et al. *J. Allergy Clin. Immunol.* 127:208-17 (2011); Straumann, A. et al. *J. Allergy Clin. Immunol.* 108:954-61 (2001)).

EE diagnosis requires endoscopy with biopsy analysis. Reliable, non-invasive techniques for the diagnosis of EE, such as biomarker detection methods, would be preferable to endoscopic techniques. While blood levels of potential EE biomarkers, such as eosinophils, eotaxin-3, eosinophil-derived neurotoxin, and IL-5 proteins, are known to be elevated in EE, such non-invasive techniques have heretofore not been widely used because their sensitivity and specificity are generally too low to be clinically helpful (see, e.g., Konikoff M. et al. *Gastroenterology* 131:1381-91 (2006)).

Eosinophils are multifunctional effector cells produced in the bone marrow from eosinophil lineage-committed progenitor cells. Eosinophils are implicated in the pathogenesis of a variety of diseases, including asthma, hypereosinophilic syndrome, eosinophil gastrointestinal disorders, and parasitic infections, including helminth infection (see, e.g., Broide, D. et al. *J. Allergy Clin. Immunol.* 127:689-95 (2011); Venge, P. *Clin. Respir. J.* 4 Suppl. 1:15-19 (2010); Anthony, R. et al. *Nat. Rev. Immunol* 7:975-87 (2007); Hogan, S. et al. *Clin. Exp. Allergy* 38:709-50 (2008)).

Eosinophils differentiate from hematopoietic stem cells via a common myeloid progenitor cell in mice through an intermediate granulocyte/macrophage progenitor, then via an eosinophil lineage committed progenitor marked by $CD34^+$ and $CD125^+$ (see, e.g., Iwasaki, H. et al. *J. Exp. Med.* 201:1891-7 (2005)). The cytokine IL-5 is particularly important in eosinophil lineage development, as it promotes the selective differentiation of eosinophils and also stimulates the release of mature eosinophils from the bone marrow (see, e.g., Hogan, S. et al. *Clin. Exp. Allergy* 38:709-50 (2008)). IL-5 has also been shown to promote eosinophil survival by activating MAP kinase, Lyn tyrosine kinase, and PI3 kinase signaling (see, e.g., Kouro, T. et al. *Int. Immunol.* 21:1303-9 (2009); Rosas, M. et al. *J. Leukoc. Biol.* 80:186-95 (2006)).

A lineage-committed eosinophil progenitor population that gives rise exclusively to eosinophils was identified in both murine and human bone marrow (Iwasaki, H. et al. *J. Exp. Med.* 201:1891-7 (2005); Mori, Y. et al. J. Exp. Med. 206:183-93 (2009)). This eosinophil lineage committed progenitor population is IL-5Rα positive, while the non-eosinophil lineage committed progenitors are IL-5Rα negative, and IL-5 was shown to induce the growth and maturation of eosinophils (see, e.g., Iwasaki, H. et al. *J. Exp. Med.* 201:1891-7 (2005); Dyer, K. et al. *J. Immunol.* 181:4004-9 (2008)). Although key transcription factors have been identified to regulate eosinophil lineage commitment (e.g. C/EBP, GATA1 and PU.1), the mechanisms controlling the growth and proliferation of eosinophil progenitor cells in response to IL-5 have heretofore not been well understood.

Multiple studies have demonstrated that EE is associated with marked changes in gene expression, particularly in the esophagus, where ~1% of the human genome has an altered, tissue-specific expression pattern, collectively referred to as the EE transcriptome, that is largely but not fully reversible following disease remission with glucocorticoid therapy (see, e.g., Blanchard, C. et al. *J. Clin. Invest.* 116:536-47 (2006); Blanchard, C. et al. *J. Allergy Clin. Immunol.* 120:1292-300 (2007); Abonia, J. et al. *J. Allergy Clin. Immunol.* 126:140-9 (2010); Sherrill, J. and Rothenberg, M. *J. Allergy Clin. Immunol.* 128:23-32 (2011)). Although several phenotypic subsets of EE patients have emerged, EE esophageal transcriptome analysis has revealed a highly conserved expression profile irrespective of patient phenotype (as defined by sex, atopic status, and familial clustering). However, the sensitivity of the EE transcriptome has not been fully established (see, e.g., Blanchard, C. et al. *J. Allergy Clin. Immunol.* 118:1054-9 (2006); Blanchard, C. and Rothenberg, M. *Gastrointest. Endosc. Clin. N. Am.* 18:133-43 (2008)). In addition to acquired gene expression changes in the esophagus, EE is also an inherited disease that involves a complex combination of genetic and environmental factors (see, e.g., Sherrill, J. and Rothenberg, M. *J. Allergy Clin. Immunol.* 128:23-32 (2011)).

EE studies have uncovered the key interplay of the adaptive and innate immune system, including the key role of IL-13-driven epithelial cell gene responses, including eotaxin-3. Characterization of gene expression differences between patients with EE and non-EE subjects via esophageal microarray expression analysis has established eotaxin-3 as the most overexpressed gene in patients with EE; this finding has been replicated in independent studies (see, e.g., Blanchard, C. et al. *Int. J. Biochem. Cell Biol.* 37:2559-73 (2005); Bhattacharya, B. et al. *Hum. Pathol.* 38:1744-53 (2007); Lucendo, A. et al. *Am. J. Gastroenterol.* 103:2184-93 (2008)).

IL-13-induced epithelial gene and protein expression changes are central to the pathogenesis of multiple allergic diseases, including EE and asthma. IL-13 is an adaptive immune cytokine that is involved in mediating the effector functions of $T_H2$ responses. The central role of IL-13 in allergic disorders has been demonstrated by the attenuation of experimental allergic diseases in animals with blockade and/or gene deletion of IL-13 and/or its receptor signaling components (see, e.g., Leigh, R. et al. *Am. J. Respir. Crit. Care Med.* 169:860-7 (2004); Yang, M. et al. *J. Immunol.* 177:5595-603 (2006); Grunig, G. et al. *Science* 282:2261-3 (1998); Junttila, I. et al. *J. Exp. Med.* 205:2595-608 (2008); Lee, P. et al. *J. Clin. Invest.* 116:163-73 (2006)).

One of the critical functions of IL-13 is to modify epithelial gene expression at sites of inflammation. IL-13-induced gene expression changes in epithelial cells in vitro have been shown to significantly overlap with gene expression changes seen in patients in vivo (see, e.g., Wills-Karp, M. *Immunol. Rev.* 202:175-90 (2004); Liacouras, C. et al. *J. Allergy Clin. Immunol.* 128:3-20 (128); Rothenberg, M. *Gastroenterology* 137:1238-49 (2009); Blanchard, C. et al. *J. Allergy Clin. Immunol.* 120:1292-1300 (2007); Lee, J. et al. *Am. J. Respir. Cell. Mol. Biol.* 25:474-85 (2001); Laprise, C. et al. *BMC Genomics* 5:21 (2004); Woodruff, P. et al. *Proc. Natl. Acad. Sci. U.S.A.* 104:15858-63 (2007); Zhen, G. et al. *Am. J. Respir. Cell. Mol. Biol.* 36:244-54 (2007)). The epithelial cell has been shown to be a key target cell type for IL-13 mediated responses, making it an attractive model for investigation. For example, epithelial cells are required for IL-13-induced airway hyper-reactivity and mucus production (Kuperman, D. et al. *Nat. Med.* 8:885-9 (2002)), and IL-13-induced epithelial cell gene expression changes have a critical role in the pathogenesis of EE (Blanchard, C. et al. *J. Allergy Clin. Immunol.* 120:1292-1300 (2007)).

Recent early clinical studies with IL-13-neutralizing agents provide evidence that anti-IL-13 holds promise for the treatment of allergic disorders, especially in patient subgroups, based on the expression profiles of various genes (especially periostin) (Corren, J. et al. *N. Engl. J. Med.* 365:1088-98 (2011)). Therefore, study of IL-13-mediated responses and the pathways that regulate IL-13-induced gene expression will provide insight into therapeutic strategies, especially for allergic disorders characterized by IL-13 overproduction, such as EE and asthma.

Most studies concerning the regulation of the EE transcriptome have focused on the induction and regulation of in situ gene expression by cytokines (e.g. IL-13), transcription factors, and co-activators (e.g. STAT6 and CBP) (see, e.g., Blanchard, C. et al. *J. Allergy Clin. Immunol.* 120:1292-300 (2007); Lim, E. et al. *J. Biol. Chem.* 286:13193-204 (2011); Blanchard, C. et al. *J. Immunol.* 184:4033-41 (2010)). However, other regulatory processes, such as those involving microRNAs (miRNAs), have not been explored.

EE-Associated miRNAs

As disclosed herein, certain miRNAs are associated with EE. Additionally, miRNA expression profiles can be studied in RE, which has a highly conserved, disease-specific transcript profile. A patient's miRNA plasma or serum levels can be measured to provide or contribute to an EE diagnosis; this information can be used to determine an appropriate treatment for the patient.

MiRNAs are single-stranded, non-coding RNA molecules of 19-25 nucleotides in length that regulate gene expression post-transcriptionally to silence target genes by either inhibiting protein translation or facilitating the degradation of target mRNAs (see, e.g., Sayed, D. and Abdellatif, M. *Physiol. Rev.* 91:827-87 (2011); Winter, J. et al. *Nat. Cell. Biol.* 11:228-34 (2009)). In animals, miRNAs base pair with the complementary regions in the 3' untranslated regions of mRNA and induce translational repression and/or mRNA degradation depending on the degree of complementarity of the base pairing (Carthew, R. and Sontheimer, E. *Cell* 136:642-55 (2009)). MiRNAs represent a key class of regulators of messenger RNA (mRNA) expression and translation and have diverse roles in fundamental biological processes, such as cell proliferation, differentiation, apoptosis, stress response, and immune response, among many others (see, e.g., Sayed, D. and Abdellatif, M. *Physiol. Rev.* 91:827-87 (2011)). To date, few studies have examined the role of miRNAs in human allergic and/or esophageal diseases, except for the setting of asthma and esophageal cancers (see, e.g., Smith, C. et al. *World J. Gastroenterol.* 16:531-7 (2010); Mattes, J. et al. *Proc. Natl. Acad. Sci. U.S.A.* 106:18704-9 (2009); Kumar, M. et al. *J. Allergy Clin. Immunol.* 128:1077-85 (2011); Collison, A. et al. *J. Allergy Clin. Immunol.* 128:160-7 (2011); Jiang, X. *Mol. and Cell. Biochein.* 353:35-40 (2011); Lu, T. et al. *J. Immunol.* 182: 4994-5002 (2009); Lu, T. et al. *J. Immunol.* 187:3362-73 (2011)).

MiRNAs represent a particularly attractive class of molecules in the regulation of the EE transcriptome, as a single miRNA can target hundreds of genes and can mediate the epigenetic mechanisms underlying gene-environment interactions, which can have a key but heretofore unexplored role in EE (see, e.g., Sato, F. et al. *Febs J.* 278:1598-609 (2011)). In addition, miRNA involvement in EE is interesting due to the recent identification of a key role of a specific T helper type 2 ($T_H2$)-associated miRNA, namely miR-21, in critically regulating T helper cell polarization, as EE involves a local polarized $T_H2$ response (see, e.g., Blanchard, C. et al. *J. Allergy Clin. Immunol.* 127:208-17 (2011); Lu, T. et al. *J. Immunol.* 182:4994-5002 (2009); Straumann, A. et al. *J. Allergy Clin. Immunol.* 108:954-61 (2001)).

Different hematopoietic lineages have significant differences in their miRNA expression (see, e.g., Navarro, F. and Lieberman, J. *J. Immunol.* 184:5939-47 (2010); Petriv, O. et al. *Natl. Acad. Sci. U.S.A.* 107:15443-8 (2010)). While various miRNAs have been shown to regulate the differentiation and lineage commitment of hematopoietic progenitor cells (see, e.g., Navarro, F. and Lieberman, J. *J. Immunol.* 184:5939-47 (2010); Georgantas, R. et al. *Proc. Nat. Acad. Sci. U.S.A.* 104:2750-5 (2007)), the mechanism for miRNA regulation over the development of hematopoietic cells after lineage commitment, including regulation of eosinophil progenitor cell growth by miRNAs, has heretofore not been well-described.

Although multiple cytokines (including IL-3, IL-5, and GM-CSF) and transcription factors (including Gata1 and PU1.1) have been shown to regulate the growth of eosinophil progenitors (see, e.g., Rothenberg, M. and Hogan, S. *Annu. Rev. Immunol.* 24:147-174 (2006)), other regulatory molecules, such as miRNAs, can have a role in regulating or fine-tuning this process. One recent report has shown that miR-21* can regulate the pro-survival effect of GM-CSF on eosinophils (Wong, C. et al. *Immunobiology,* 218:255-62 (2013)).

Although the miRNA let-7 has been shown to target IL-13 directly, and miR-155 has been shown to target IL-13Rα1 (Martinez-Nunez, R. et al. *J. Biol. Chenz.* 286:1786-94 (2011); Kumar, M. et al. *J. Allergy Clin. Immunol.* 128: 1077-85, e1-10 (2011); Polikepahad, S. et al. *J. Biol. Chem.* 285:30139-49 (2010)), there has heretofore been little evidence to demonstrate that IL-13-induced miRNAs can regulate or fine tune IL-13 mediated-responses.

MiRNA Expression Profiles

As described herein, a comprehensive analysis of global miRNA expression profiles was conducted on the esophageal tissues of patients with active EE, active chronic esophagitis, EE patients in remission after glucocorticoid treatment who have a mainly normalized EE transcriptome (see, e.g., Blanchard, C. et al. *J. Allergy Clin. Immunol.* 120:1292-300 (2007); Caldwell, J. et al. *J. Allergy Clin. Immunol.* 125:879-888 (2010)), and normal control subjects; this study established a miRNA signature for EE patients. This EE miRNA signature is distinct from that of chronic esophagitis patients and is largely reversible upon disease remission.

Specifically, 21 upregulated and 11 downregulated miRNAs were identified in patients with active EE, including miR-21 and miR-223 as the most upregulated miRNAs and miR-375 as the most downregulated miRNA in patients with EE. These miRNAs can therefore serve as biomarkers for EE alone or in combination with other biomarkers. Three of the differentially regulated miRNAs in the esophageal biopsies, namely miR-146a, miR-146b, and miR-223, were also differentially regulated in EE patient plasma samples; these miRNAs can therefore be used as non-invasive biomarkers for EE alone or in combination with other biomarkers.

This EE-associated miRNA signature correlated with the degree of tissue eosinophilia and was distinct from patients with chronic (non-eosinophilic) esophagitis. The differential miRNA expression was largely reversible in patients that responded to glucocorticoid therapy. These results therefore demonstrate the dynamic expression of miRNAs in a human allergic disease and the role for tissue and blood miRNAs as biomarkers to provide insight into disease diagnosis, response to therapy, and the degree of allergic inflammation.

As described herein, the role of miRNA in regulating $T_H2$-associated diseases, including EE, was established. Studies on the roles and regulations of the miRNAs differentially regulated in EE can lead to improved patient diagnosis and facilitate the development of miRNA mimics and inhibitors as therapies for EE patients.

MiR-21, which has been shown to regulate IL-12 expression and the balance of $T_H1$ vs. $T_H2$ responses in mice (see, e.g., Lu, T. et al. *J. Immunol.* 182:4994-5002 (2009); Lu, T. et al. *J. Immunol.* 187:3362-73 (2011)), was found to be one of the most up-regulated miRNAs in EE patients. Due to the high level of species conservation of the miR-21 binding site in the 3' untranslated region of IL12p35, miR-21 can have a similar role in human allergic inflammation (see, e.g., Lu, T. et al. *J. Immunol.* 182:4994-5002 (2009)). The results described herein provide the first set of human data that substantiate that miR-21 can have a similar role in human allergic inflammation.

Both miR-223 and miR-21 were recently found to be up-regulated in eosinophilic esophagitis patients (Lu, T. et al. *J. Allergy Clin. Immunol.,* 129:1064-1075 e1069 (2012)). They are the top two miRNAs correlated with eosinophil levels in patient esophageal biopsies. Using systems biology analysis, miR-223 and miR-21 were found to co-regulate a set of interacting target genes involved in eosinophil proliferation and differentiation (Lu, T. et al. *J. Allergy Clin. Immunol.,* 129:1064-1075 e1069 (2012)). Because miR-21 promotes cell proliferation, the up-regulation of miR-223 can provide a check and balance in the system given the ability of miR-223 to promote eosinophil maturation.

Furthermore, because miR-21*, a complementary miRNA of miR-21, was up-regulated after GM-CSF treatment and can inhibit the apoptosis of eosinophils (Wong, C. et al. *Immunobiology*, 218:255-62 (2013)), the minor miR-NAs can also have a role in regulating the proliferation of eosinophil progenitors, adding another level of complexity. Therapies targeting miRNAs, including miR-21, miR-223, and their minor miR* forms, can allow fine-tuning of the eosinophil level in various diseases.

Upregulation of miR-21 in patients with EE can partially explain the increased $T_H2$ cytokine levels and $T_H2$ responses seen in EE patients. As described herein, esophageal miR-21 levels were found to be inversely correlated with esophageal IL-12p35 levels. Up-regulation of miR-21 in EE patients can therefore partially explain the increased $T_H2$ cytokines and $T_H2$ responses seen in EE patients. Studies using human data can further elucidate the role of miR-21 in human allergic inflammation.

Co-regulated miR-21 target genes in EE patients were found to be significantly enriched in the regulation of T cell polarization and IFNγ production. Direct analysis of a myriad of esophageal transcripts for correlation with miR-21 demonstrated strong correlations with key elements of the EE transcriptome, including cell-specific markers for key inflammatory cells (such as eosinophils and mast cells), as well as CCL26 (also known as eotaxin-3), which is functionally involved in eosinophil recruitment (see, e.g., Shinkai, A. et al. *J. Immunol.* 163:1602-10 (1999)) and POSTN (periostin), which is involved in tissue remodeling (see, e.g., Stansfield, W. et al. *Ann. Thorac. Surg.* 88:1916-21 (2009)) and eosinophilia (see, e.g., Blanchard, C. et al. *Mucosal Inzmunol.* 1:289-96 (2008)), and which has recently shown to be a key biomarker for anti-IL-13 responsiveness in human asthma (Corren, J. et al. *N. Engl. J. Med.* 365:1088-98 (2011)). These data provide the first human evidence to substantiate the recent findings that miR-21 critically regulates the polarization of adaptive immunity in mice (Lu, T. et al. *J. Immunol.* 187:3362-73 (2011)), supporting the previous finding that miR-21 regulates $T_H1$ vs. $T_H2$ balances by targeting IL-12p35 expression (Lu, T. et al. *J. Immunol.* 182:4994-5002 (2009)).

As described herein, let-7c was found to be down-regulated, meaning let-7c can be used to regulate IL-13 levels (Polikepahad, S. et al. *J. Biol. Chem.* 285:30139-49 (2010)). Up-regulation of miR-146a was found in EE patients. As miR-146a has recently been demonstrated to selectively regulate Treg-mediated suppression of $T_H1$ cells (Lu, L. et al. *Cell* 142:914-29 (2010)), up-regulation of miR-146a can suppress $T_H1$ responses and promote $T_H2$ responses.

These findings support a model whereby multiple miR-NAs coordinate polarized $T_H$ responses in the pathogenesis of EE. Recent human studies on two other $T_H2$ associated diseases, namely atopic dermatitis and ulcerative colitis, have identified a role for miRNA in regulating T cell proliferation and epithelial-derived chemokine production, as well as up-regulation of miR-21 in ulcerative colitis and down-regulation of let-7 in atopic dermatitis (Wu, F. et al. *Gastroenterology* 135:1624-1635 (2008); Sonkoly, E. et al. *J. Allergy Clin. Immunol.* 126:581-9 (2010)).

One of the defining histological features of EE is intense eosinophil infiltration in the esophagus. As described herein, a majority of the dysregulated miRNAs demonstrate significant correlation between miRNA expression level and esophageal eosinophil count, reflecting disease severity. Functional enrichment analyses were performed for the two miRNAs that most strongly correlated with eosinophil levels, namely miR-21 and miR-223; these analyses empirically predicted that both miRNAs regulate levels of tissue eosinophilia, demonstrating the interplay between these two miRNAs in allergic inflammation. Both miRNAs correlated significantly with IL-5, a key eosinophil growth factor shown to be contributory in murine models of EE and human EE (see, e.g., Mishra, A. et al. Gastroenterology 134:204-14 (2008); Assa'ad, A. et al. *Gastroenterology* 141:1593-604 (2011)).

Another significant histological finding in EE patients is epithelial basal layer hyperplasia. In particular, miR-203 is known to repress epithelial cell proliferation and promote epithelial cell differentiation (see, e.g., Yi, R. et al. *Nature* 452:225-9 (2006)). As such, repression of miR-203 can in part explain the observed epithelial hyperplasia.

Several of the EE-associated miRNAs have been linked with esophageal squamous carcinoma or with Barrett's esophagus, including let-7 (Liu, Q. et al. *Mol. Biol. Rep.* 39:123946 (2012)), miR-142-3p (Lin, R. et al. *J. Surg. Oncol.* 105:175-82 (2011)), miR-203 (Yuan, Y. et al. *BMC Cancer* 11:57 (2011)), miR-210 (Tsuchiya, S. et al. *J. Biol. Chem.* 286:420-8 (2011)), miR-223 (Li, S. et al. *J. Biomed. Sci.* 18:24 (2011)), miR-375 (Li, X. et al. *Dig. Dis. Sci.* 56:2849-56 (2011)), and miR-21 (Matsushima, K. et al. *Digestion* 82:138-44 (2010)). Some miRNAs, such as miR-21, have been shown to be oncomirs and/or tumor suppressors (see, e.g., Medina, P. et al. *Nature* 467:86-90 (2010); Hatley, M. et al. *Cancer Call* 18:282-93 (2010)). While EE is not considered to be a pre-malignant condition, EE involves marked epithelial cell hyperplasia, and these miR-NAs can have a role in this feature of EE.

As described herein, miR-675 was found to be the only disease remission-induced miRNA. MiR-675 is derived from the H19 gene, which is a paternally imprinted gene (see, e.g., Cai, X. and Cullen, B. *RNA* 13:313-6 (2007)). The over-expression of H19 is commonly associated with various cancers (see, e.g., Tsang, W. Carcinogenesis 31:350-8 (2010)). H19 was previously found to be induced in glucocorticoid responder patients compared to EE patients or normal controls; this induction was not seen in patients that did not respond to glucocorticoid therapy (Caldwell, J. et al. *J. Allergy Clin. Immunol.* 125:879-888 (2010)).

As described herein, the miR-675 expression pattern closely resembles that of H19. Since the exact roles of H19 and its miRNA product, namely miR-675, in the disease remission process have heretofore been unknown, elucidating their functions can provide information regarding the disease remission process in EE. Based on the role H19 and miR-675 can have in DNA methylation responses and the unique overexpression of this miRNA specifically within patients in remission, miR-675 can be involved in epigenetic programming in the esophageal cells of EE remission patients.

As described herein, the expression levels of a selected set of EE-associated miRNAs in EE patient plasma samples were measured. MiR-146a, miR-146b, and miR-223 were found to be up-regulated in the EE plasma samples compared to controls (allergic individuals without EE). These miRNAs can therefore serve as non-invasive biomarkers for EE alone or in combination with other non-invasive biomarkers.

Plasma miRNAs have been reported to exist both within exosomes and in protein-bound vesicle-free form (see, e.g., Arroyo, J. et al. *Proc. Natl. Acad. Sci. U.S.A.* 108:5003-8 (2011); Rabinowits, G. et al. *Clin. Lung Cancer* 10:42-6 (2009)). The circulating miRNAs can be taken up by cells through exosome uptake or pinocytosis (see, e.g., Valadi, H. et al. *Nat. Cell Biol.* 9:654-9 (2007); Tian, T. et al. *J. Cell. Biochem.* 111:488-96 (2010)). Mast cells have been found to release exosomes containing miRNA (see, e.g., Valadi, H. et al. Nat. Cell Biol. 9:654-9 (2007)). Mast cells also express high levels of both miR-146a and miR-146b (see, e.g., Sonkoly, E. et al. *PLoS One* 2:e610 (2007); Mayoral, R. et al. *J. Immunol.* 182:433-45 (2009)). EE patients have concomitant esophageal mastocytosis (see, e.g., Abonia, J. et al. *J. Allergy Clin. Immunol.* 126:140-9 (2010); Aceves, S. et al. *J. Allergy Clin. Immunol.* 126:1198-204 (2010); Dellon, E. et al. *Am. 0.1 Gastroenterol.* 106:264-71 (2011)), which could account for the elevated miR-146a and miR-146b levels seen in the serum of EE patients. Since miR-146a has been found to selectively promote Treg-mediated suppression of $T_H1$ response, an increased circulating level of plasma miR-146a can further propagate or help maintain the $T_H2$ responses seen in EE patients.

As described herein, while plasma miR-146a and miR-223 returned to baseline levels during EE remission, miR-146b remained elevated in EE remission patients. While the specific role of miR-146b in regulating adaptive immune responses has not been investigated, miR-146a and miR-146b have an identical seed sequence that is critical for miRNA-mediated target gene expression. Therefore, miR-146b can also suppress $T_H1$ responses and promote $T_H2$ responses. EE patients in remission often relapse as time progresses (see, e.g., Assa'ad, A. et al. *J. Allergy Clin. Immunol.* 119:731-8 (2007)). Therefore, an elevated level of miR-146b can predispose EE patients in remission to a relapse.

Targeted Ablation of miR-21 Decreases Murine Eosinophil Progenitor Cell Growth

MiR-21 has been reported to be up-regulated in a variety of disorders associated with eosinophilia, including asthma (see, e.g., Lu, T. et al. *Immunol.* 182:4994-5002 (2009)), ulcerative colitis (see, e.g., Wu, F. et al. *Gastroenterology* 135:1624-35 e1624 (2008)), and eosinophilic esophagitis (Lu, T. et al. *J. Allergy Clin. Immunol.*, 129:1064-75 (2012)). MiR-21 has been reported to be pro-proliferative and anti-apoptotic by targeting multiple tumor suppressor genes (see, e.g., Krichevsky, A. and Gabriely, G. *J. Cell. Mol. Med.* 13:39-53 (2009); Papagiannakopoulos, T. et al. *Cancer Res.* 68:8164-72 (2008); Hatley, M. et al. *Cancer Cell* 18:282-93 (2010)). Several of the miR-21 target genes, including Apaf1 and PTEN, have been implicated in inhibiting eosinophil proliferation or promoting its apoptosis (see, e.g., Jakicla, B. et al. *Rheumatology* (Oxford) 48:1202-7 (2009); Adachi, T. et al. *J. Immunol.* 179:8105-11 (2007)). Although the transcription factor Gfi1 has been found to repress miR-21 expression during the transition from common myeloid progenitor to the granulocyte/macrophage progenitor stage, thereby promoting neutrophil/monocyte differentiating conditions (see, e.g., Velu, C. et al. *Blood* 113:4720-8 (2009)), little information has heretofore been available regarding the function of miR-21 during eosinophil differentiation.

As described herein, miR-21 was found to be among the most up-regulated miRNAs in patients with EE and has the highest correlation with esophageal eosinophil levels. MiR-21 has been identified as a regulator of eosinophil progenitor growth and is the first miRNA proven to have a role in directly regulating eosinophil development. MiR-21 was found to be up-regulated during eosinophil differentiation from eosinophil progenitors, and targeted ablation of miR-21 was found to decrease eosinophil progenitor growth.

MiR-21 is shown to be progressively up-regulated during IL-5-driven eosinophil differentiation from progenitor cells in vivo. Eosinophil progenitor cultures derived from miR-$21^{-/-}$ mice were found to have increased levels of apoptosis as indicated by increased levels of annexin V positivity compared to those of miR-$21^{+/+}$ mice. MiR-$21^{-/-}$ mice were found to have decreased eosinophil colony forming unit capacity in the bone marrow and reduced blood eosinophil levels in vivo. Therefore, targeted ablation of miR-21 in the eosinophil progenitor cultures leads to reduced eosinophil progenitor growth capacity.

Whole genome microarray analysis of miR-$21^{+/+}$ and miR-$21^{-/-}$ eosinophil progenitor cultures identified differentially regulated genes between miR-$21^{+/+}$ and miR-$21^{-/-}$ eosinophil progenitor cultures. These included genes involved in cell proliferation (e.g. Ms4a3, Grb7, and Pik3r6), cell cycle, and immune response; therefore, these pathways were identified as those pathways in eosinophils most significantly affected by miR-21.

These results demonstrate that miR-21 can directly regulate the development of eosinophils by influencing the growth capacity of eosinophil progenitors. Since mature cosinophils lose their proliferative capacity and do not divide, the up-regulation of miR-21 can prevent premature loss of the proliferative potential of eosinophil progenitors. Further elucidation of the roles of miR-21 in regulating eosinophil levels and immunoinflammatory responses can lead to therapeutic options for eosinophilic disorders.

No differentially regulated genes were identified at day 4 of the eosinophil progenitor culture, supporting previous findings that progenitor cell growth under the influence of stem cell factor (SCF) and Flt-3L is not regulated by miR-21. There were 38 differentially regulated genes that were identified between days 8 and 14, with only one (Psrc1) being a predicted target of miR-21. Computational analysis identified an overall functional effect exactly in the pathways (e.g. regulation of cell proliferation and cell cycle) associated with the observed phenotype and the known role of miR-21 in other systems (Krichevsky, A. and Gabriely, G. *J. Cell. Mol. Med.* 13:39-53 (2009); Hatley, M. et al. *Cancer Cell* 18:282-93 (2010)). As such, miR-21 can exert some effects on direct targets that synergistically interact to ultimately regulate eosinophilopoeisis. Moreover, miR-21 can regulate additional genes at the protein level that were not identified by the genomic screen in the current study. The observed decreased growth capacity of the miR-$21^{-/-}$ eosinophil progenitors is likely due to modest regulation of a combination of miR-21 targets.

More than a dozen anti-proliferative genes have been reported as miR-21 targets, including Pdcd4, Pten, Tpm1, Apaf1, Btg2, Map2k3, RhoB, and Ski, among many others (Krichevsky, A. and Gabriely, G. *J. Cell. Mol. Med.* 13:39-53 (2009); Hatley, M. et al. *Cancer Cell* 18:282-93 (2010)). Among these, over-expression of Pten has been shown to attenuate eosinophil survival (Adachi, T. et al. *J. Immunol.* 179:8105-11 (2007)), and Apaf-1 is part of the intrinsic apoptosis pathway that is suppressed by IL-5 signaling (Dewson, G. et al. *Blood* 98:2239-47 (2001)). The observed decreased growth capacity of the miR-$21^{-/-}$ eosinophil progenitors can be due to modest regulation of a combination of miR-21 targets.

Psrc1, one of the up-regulated genes, is a predicted target of miR-21 based on sequence conservation and binding site potential (Lu, T. et al. *J. Immunol.* 182:4994-5002 (2009)). Over-expression of Psrc1 has been shown to suppress colony formation in lung carcinoma cells (Lo, P. et al. *Oncogene* 18:7765-74 (1999)). The up-regulation of Psrc1 could potentially contribute to the decreased growth of miR-$21^{-/-}$ eosinophil progenitors.

As described herein, the gene Pik3r6, a regulatory subunit for phosphoinositide 3-kinase (PI3 kinase) gamma, was over-expressed in both day 8 and day 12 in the miR-21$^{-/-}$ eosinophil progenitor cultures. PI3 kinase signaling has been shown to be essential for IL-5 mediated eosinophil survival (Rosas, M. et al. *J. Leukoc. Biol.* 80:186-95 (2006)). Pik3r6 has been shown to be expressed primarily in the hematopoietic compartment and can potentially compete with Pik3r5 for binding with p110γ (Suire, S. et al. *Curr. Biol.* 15:566-70 (2005)). The Pik3r6/p110γ heterodimer is four-fold less sensitive than the Pik3r5/p110γ heterodimer (Suire, S. et al. *Curr. Biol.* 15:566-70 (2005)). As described herein, Pik3r6 and Pik3r5 are expressed at similar levels in the wild type eosinophil progenitors. Up-regulation of Pik3r6 can lead to an increased level of Pik3r6/p110γ heterodimer and a decreased level of Pik3r5/p110γ heterodimer, thereby attenuating PI3 kinase signaling. This can in part account for the decreased growth seen in miR-21$^{-/-}$ eosinophil progenitors.

MiR-21 has been known to promote cell growth in various cell types, most notably in tumor cells, by targeting a variety of pro-apoptotic genes both directly and indirectly (Krichevsky, A. and Gabriely, G. *J. Cell. Mol. Med.* 13:39-53 (2009); Hatley, M. et al. *Cancer Cell* 18:282-93 (2010)). As described herein, increased levels of apoptosis were found in miR-21$^{-/-}$ eosinophil cultures compared to miR-21$^{+/+}$ cultures. Potential eosinophil hematopoiesis defects were investigated in the miR-21$^{-/-}$ mice in vivo. The miR-21$^{-/-}$ mice were found to have both decreased eosinophils in the blood and decreased eosinophil colony forming unit capacity in the bone marrow, consistent with the observed phenotype in the ex vivo eosinophil cultures.

MiR-21 has been found to be over-expressed in allergic diseases with significant eosinophilia, including experimental asthma in mice and human EE (Lu, T. et al. *J. Immunol.* 182:4994-5001 (2009); Wu, F. et al. *Gastroenterology* 135:1624-1635 e1624 (2008); Lu, T. et al. *J. Immunol.* 187:3362-73 (2011); Lu, S. et al. *PLoS One,* 7:e40676 (2012)). MiR-21 was previously found to be capable of regulating immunoinflammatory responses by targeting the IL12/IFNγ pathway (Lu, T. et al. *J. Immunol.* 182:4994-5001 (2009); Lu, T. et al. *J. Immunol.* 187:3362-73 (2011)). Regulation of inflammatory response was also found to be one of the significantly enriched pathways represented by the differentially expressed genes in the miR-21 deficient eosinophil progenitor cultures. These results indicate that miR-21 can have additional roles in regulating the immunoinflammatory responses beyond regulation of the IL12/IFNγ pathway. Because miR-21 can also affect eosinophil progenitor growth, therapeutic interventions targeting miR-21 can reduce the levels of eosinophilia in some circumstances.

In summary, miR-21 has been identified as a regulator of eosinophil progenitor growth. This represents the first miRNA demonstrated to have a direct role in regulating eosinophil development. Further elucidating and understanding the roles of miR-21 in regulating the levels of eosinophils and in immunoinflammatory responses can lead to additional therapeutic options for eosinophilic disorders.

MiR-223 Deficiency Increases Eosinophil Progenitor Cell Growth

MiR-223 has been found to be over-expressed in asthma, EE, and atopic dermatitis, where eosinophils are implicated in the disease pathogenesis to varying degrees (Lu, T. et al. *J. Immunol.* 182:4994-5002 (2009); Garbaeki, N. et al. *PLoS One* 6:e16509 (2011); Sonkoly, E. et al. *J. Allergy Clin. Immunol.* 126:581-9 (2010); Mattes, J. et al. *Proc. Natl. Acad. Sci. U.S.A.* 106:18704-0 (2009)). MiR-223 has been shown to target the IGF1 receptor (IGF1R) (see, e.g., Johnnidis, J. et al. *Nature* 451:1125-9 (2008)), which is the major physiologic receptor for IGF1 (see, e.g., Smith, T. *Pharmacol. Rev.* 62:199-236 (2010)). IGF1 is a major anabolic hormone that stimulates cell growth and is a potent inhibitor of programmed cell death; therefore IGF1R can be differentially regulated by miR-223. Although IGF1 has not been previously examined for its impact on eosinophil progenitors, IGF1 and IGF1R inhibitors can be clinically useful for eosinophilic disorders. The expression of miR-223 has been shown to be mediated by myeloid transcription factors PU.1 and C/EBP, factors that are important in eosinophilopoiesis (see, e.g., Fukao, T. et al. *Cell* 129:617-31 (2007)).

As described herein, miR-223 was found to regulate the proliferation and differentiation of eosinophil progenitors; miR-223 was also found to be up-regulated during eosinophil differentiation in an ex vivo bone marrow-derived eosinophil culture model. MiR-223-deficient eosinophil progenitor cells were found to have a hyperproliferative capacity. Mechanistic analysis identified a contributory role for the IGF1 receptor (IGF1R) in mediating eosinophil progenitor cell proliferation.

Gene expression analysis followed by systems biological analysis identified the role of miR-223 in hematopoietic development and cellular growth and function. Consistent with this prediction, miR-223$^{-/-}$ mice had a delay in eosinophil differentiation as assessed by CCR3 expression. These data demonstrate that miRNAs can directly regulate the development of eosinophils by influencing the proliferation and differentiation of eosinophil progenitor cells.

MiR-223 was found to regulate the growth and differentiation of eosinophil progenitors. MiR-223 was found to be up-regulated in an ex vivo bone marrow-derived eosinophil differentiation culture. Targeted ablation of miR-223 leads to an increase in eosinophil progenitor growth, as miR-223$^{-/-}$ cells had a markedly increased growth in response to the eosinophil growth factor IL-5. In addition, miR-223 deficiency led to a defect in eosinophil maturation, as indicated by a delayed up-regulation of surface CCR3 expression.

Up-regulation was found for the miR-223 target gene IGF1R in eosinophil cultures derived from miR-223$^{-/-}$ mice compared to miR-223$^{+/+}$ littermate controls (Johnnidis, J. et al. *Nature* 451:1125-9 (2008)). The up-regulation of IGF1R coincided with the onset of the increased growth seen in the miR-223$^{-/-}$ eosinophil culture. MiR-223 has therefore been identified as a regulator of eosinophil IGF1R levels.

The increased growth observed in the eosinophil cultures derived from miR-223$^{-/-}$ mice was found to be reversible upon treatment with an IGF1R inhibitor. The growth of miR-223$^{+/+}$ eosinophil progenitors can also be inhibited by an IGF1R inhibitor. These data demonstrate that the increased proliferation seen in miR-223$^{-/-}$ eosinophil cultures has not bypassed the IGF1R pathway and provide the first demonstration that IGF1R is involved in eosinophil development.

Several IGF1R inhibitors are currently under development for the treatment of various types of cancer (Yee, D. *Journal of the National Cancer Institute,* 104:975-981 (2012)). These data indicate that the IGF1R inhibitors can potentially also be used to treat patients with eosinophilia, such as the hypereosinophilic syndrome (Arefi, M. et al. *International Journal of Hematology,* 96:320-326 (2012)). Furthermore, miR-223 has been identified as a regulator of eosinophil IGF1R levels. While the up-regulation of IGF1R likely has a contributory role in the increased proliferation seen in the miR-223$^{-/-}$ eosinophil progenitor cultures, this does not preclude the involvement of additional pathways. In particular, this microarray analysis identified multiple additional growth and proliferation-related genes differentially regulated between miR-223$^{+/+}$ and miR-223$^{-/-}$ cultures. These include down-regulation of NAD(P)H:quinone oxidoreductase 1 (NQO1), where NQO1 deficient mice have been found to have a significant increase in blood granulocytes including eosinophils (Long, D. et al. *Cancer Res.*, 62:3030-3036 (2002)). Down-regulation of inhibitor of DNA binding 2 (ID2), whose knockdown has been shown to cause increased eosinophil progenitor growth and delayed eosinophil progenitor differentiation, was also observed (Buitenhuis, M. et al. *Blood*, 105:4272-4281 (2005)).

IGF1R is expressed by eosinophil progenitors, and an IGF1R inhibitor (pricopodphyllin) inhibits eosinophil progenitor cell growth. Both of these findings occur independent of miR223, although the former is regulated by miR223. Therefore, IGF1 is a new pathway involved in eosinophil development for which pharmacological blockade (independent of miR223) demonstrates a positive effect. This is the first report of the relationship between IGF1 and IGF1R in eosinophilia.

While the up-regulation of IGF1R can have a contributory role in the increased growth seen in the miR-223$^{-/-}$ eosinophil progenitor cultures, additional pathways can be involved as well. As described herein, whole genome microarray analysis identified multiple additional growth- and proliferation-related genes differentially regulated between miR-223$^{+/+}$ and miR-223$^{-/-}$ eosinophil progenitor cultures at day 8 of the culture, before the onset of the increased growth, and at day 12. There was a specific enrichment in genes that regulate hematologic cell development known to be involved in eosinophilopoicsis. These include down-regulation of NAD(P)H:quinone oxidoreductase 1 (NQO1), a cytosolic protein protecting cells against oxidative stress, and inhibitor of DNA binding 2 (ID2), an inhibitor of the basic helix-loop-helix family of transcription factors. NQO1-deficient mice have been shown to have a significant increase in blood granulocytes, including eosinophils (Long, D. et al. *Cancer Res.* 62:3030-6 (2002)). Silencing of ID2 has been shown to cause increased eosinophil progenitor growth and delayed eosinophil progenitor differentiation (Buitenhuis, M. et al. *Blood* 105:4272-81 (2005)).

Analysis of eosinophil maturation of the bone marrow-derived eosinophils indicated that the increased growth of the miR-223$^{-/-}$ eosinophil progenitor was associated with a delay in differentiation. The finding that miR-223 can regulate the development of eosinophils by influencing eosinophil progenitor growth and differentiation can therefore be used to design potential therapeutic interventions targeting or affecting levels of miR-223.

In summary, miR-223 has been identified as a regulator of eosinophil progenitor proliferation. IGF1R is up-regulated during in eosinophil development, and miR-223 is a regulator of IGF1R levels. The roles and regulations of miRNAs during eosinophil development can be utilized to lead to novel therapeutic targets for eosinophilic disorders.

MiR-375 Regulates an IL-13-Induced Epithelial Transcriptome

As described herein, a lentiviral strategy and whole-transcriptome analysis were used in epithelial cells to demonstrate that miR-375 over-expression was sufficient to markedly modify IL-13-associated immunoinflammatory pathways in epithelial cells in vitro, further substantiating interactions between miR-375 and IL-13. These results demonstrate that miRNAs have a key role in regulating and fine-tuning IL-13 mediated responses, and miR-375 is a key downstream mediator of IL-13-induced responses.

MiRNA array analysis was used to determine the differentially expressed miRNAs after IL-13 stimulation in two distinct human epithelial cell types, namely esophageal squamous cells and bronchial columnar cells. Among the IL-13-regulated miRNAs, miR-375 showed a conserved pattern of down-regulation between these two epithelial cell types. MiR-375 levels were analyzed in an IL-13-induced murine asthma model, and down-regulation was observed in the murine asthmatic lungs.

Direct examination of human allergic tissue, from esophageal biopsies from patients with EE, indicated that miR-375 was inversely related to the degree of allergic inflammation, including esophageal eosinophil levels and gene expression levels of $T_H2$ cytokines and mast cell specific proteases. MiR-375 over-expression was sufficient to markedly modify IL-13-associated immunoinflammatory pathways in epithelial cells in vitro. These results support a key role of miRNAs, particularly miR-375, in regulating and fine-tuning IL-13 mediated responses.

MiRNAs were identified that were differentially regulated after IL-13 stimulation in human bronchial columnar and esophageal squamous epithelial cells. Among the IL-13-regulated miRNAs, miR-375 was found to be the only miRNA that was down-regulated in both epithelial cell types after IL-13 stimulation in EE patient samples compared to control patients.

As described herein, analysis of different human cell types involved in allergic inflammation identified the highest expression of miR-375 in epithelial cells. MiR-375 was found to be inversely correlated with the level of esophageal eosinophils and expression of the mast cell specific genes CPA3 and TPSAB1. The down-regulation of miR-375 was specific to EE patients; the chronic esophagitis patients had miR-375 expression levels comparable to normal controls. Disease remission with either fluticasone therapy or diet modification was associated with normalization of miR-375 levels; this can be due to the result of reduced IL-13; patients that did not respond to fluticasone therapy continued to have repressed miR-375 levels.

Modulation of miR-375 levels was found to be sufficient to regulate IL-13 mediated gene expression, particularly with pathways involved in immunoinflammatory processes. Levels of miR-375 markedly inversely correlated with a large set of immunoinflammatory genes (including IL-13) in the esophagus of patients with EE.

As described herein, a genome-wide transcriptome-based approach was used to demonstrate that miR-375 can potentiate and repress IL-13-mediated effects, indicating the complex interaction between cytokine and miRNA-mediated gene regulation; miR-375 was therefore sufficient to regulate an IL-13-induced epithelial transcriptome. The inflammatory diseases and immunological diseases are the two most significantly over-represented disease states regulated by miR-375. These include allergy-associated genes, such as MMP12 and MUC4 (Mukhopadhyay, S. et al. *J. Allergy Clin. Immunol.* 126:70-6 (2010); Lavigne, M. et al. *Biochem. Biophys. Res. Comm.* 324:534-54 (2004); Fahy, J. *Am. J. Respir. Crit. Care Med.* 164:S46-51 (2001); Pouladi, M. et al. *Am. J. Respir. Cell. Mol. Biol.* 30:84-90 (2004)).

As further described herein, miR-375 expression was found to be unchanged after 2 hours of IL-13 stimulation, despite the finding of up-regulation of miR-375 after 2 hours of IL-13 stimulation reported in a previous study (Biton, M. et al. *Nat. Immunol.* 12:239-46 (2011)). This inconsistency could be due to the use of the HT-29 human colon adenocarcinoma cell line, as opposed to human esophageal squamous cells and bronchial columnar cells. MiR-375 was found to be down-regulated after 24 and 48 hours of IL-13 stimulation, which is consistent with the previous finding that miR-375 levels were at or below baseline after 16 hours of IL-13 stimulation (Biton, M. et al. *Nat. Immunol.* 12:239-46 (2011)).

While miR-375 down-regulation has been reported in patient samples from multiple $T_H2$-associated diseases, such as atopic dermatitis (Sonkoly, E. et al. *J. Allergy Clin. Immunol.* 126:581-9 (2010)) and ulcerative colitis (Wu, F. et al. *Gastroenterology* 135:1624-35 (2008)), and hyperproliferative diseases, such as esophageal squamous carcinoma (Kong, K. et al. *Gut* 61:33-42 (2011)), up-regulation of miR-375 in a $T_H2$-associated disease in humans has not been reported. Therefore, IL-13 can have the long-term effect of down-regulating miR-375 expression.

MiR-375 has been previously shown to enhance goblet cell differentiation by repressing KLF5 expression (Biton, M. et al. *Nat. Immunol.* 12:239-46 (2011)) and has also been shown to attenuate cell proliferation by targeting IGF1R, PDK1, and YWHAQ (Kong, K. et al. *Gut* 70:2239-49 (2011); Tsukamoto, Y. et al. *Cancer Res.* 70:2339-49 (2010)). As described herein, neither of these pathways was affected in EE patients or upon analysis of miR-375-regulated genes in esophageal epithelial cells (Blanchard, C. et al. *J. Clin. Invest.* 116:536-47 (2006)), indicating that the activity of miR-375 may be dependent on the cellular context, consistent with previous reports (Tsukamoto, Y. et al. *Cancer Res.* 70:2339-49 (2010); de Souza Rocha Simonini, P. et al. *Cancer Res.* 70:9175-84 (2010)).

MiR-375 has been previously reported to regulate TSLP expression in an HT-29 human colonic adenocarcinoma cell line (Biton, M. et al. *Nat. Immunol.* 12:239-46 (2011)). In this study, TSLP and miR-375 were concomitantly induced by IL-13 in HT-29 cells, and knockdown of miR-375 inhibited TSLP production. In addition, over-expression of miR-375 induced TSLP expression in HT-29 cells (Biton, M. et al. *Nat. Immunol.* 12:239-46 (2011)). TSLP has been shown to have an important role in EE pathogenesis (see, e.g., Rothenberg, M. et al. *Nat. Genet.* 42:289-91 (2010); Sherrill, J. et al. *J. Allergy Clin. Immunol.* 126:160-5 (2010)). As described herein, the ability of miR-375 to regulate TSLP expression in esophageal epithelial cells was analyzed. Additionally, miR-375 was found to have no effect on TSLP production, and there was no correlation between miR-375 and TSLP in the esophageal samples. The disparity between these results and previous studies could be due to the use of different cell types and/or different mechanisms in TSLP induction in these cells, since previous studies report that IL-13 induces TSLP expression in HT-29 cells but not in esophageal epithelial cells (Blanchard, C. et al. *J. Allergy Clin. Immunol.* 120:1292-1300 (2007); Biton, M. et al. *Nat. Immunol.* 12:239-46 (2011)).

IL-13 has been found to down-regulate miR-375 and modulate IL-13 regulated gene expression in bronchial epithelial cells; this is relevant to asthma and other IL-13-mediated diseases. However, it is unclear whether over-expression of miR-375 can correct the allergic phenotype in asthma and EE. This can be resolved in future studies utilizing miR-375 lung and/or esophageal epithelial specific transgenic mice.

Previous reports have indicated that the miRNAs miR-203 and miR-223 are differentially regulated in $T_H2$-associated diseases (Wu, F. et al. *Gastroenterology* 135:1624-35 (2008); Sonkoly, E. et al. *J. Allergy Clin. Immunol.* 126: 581-9 (2010)). As described herein, 10 other miRNAs in addition to miR-375 were identified that were differentially regulated in either human esophageal epithelial cells or human bronchial epithelial cells, reflecting cell type-specific effects of IL-13 stimulation.

MiR-375 expression levels were found to reflect disease activity, normalize with remission, and inversely correlate with the degree of allergic inflammation. MiR-375 was strongly associated with parameters germane to allergic responses, including eosinophil levels, gene expression levels of the $T_H2$ cytokines IL-5 and IL-13, the mast cell-specific enzymes CPA3 and TPSAB1, and POSTN (the gene that encodes periostin). Periostin has been demonstrated to have a key role in IL-13 associated remodeling responses (Blanchard, C. et al. *Mucosal. Immunol.* 1:289-96 (2008)), and its level predicts responsiveness to anti-IL-13 therapy in humans (Corren, J. et al. *N. Engl. J. Med.* 365:1088-98 (2011)); therefore, the finding that miR-375 strongly correlates with human POSTN levels in vivo, as described herein, can therefore be used to design potential therapeutic interventions that modulate levels of miR-375.

Treatment Based on miRNA Levels

Embodiments of the invention are directed to methods of treating EE in a patient, wherein the methods comprise analyzing the sample from a patient to determine a level of one or more miRNAs associated with EE, determining whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE, and treating the patient with an appropriate therapeutic strategy based upon the diagnosis.

Embodiments of the invention are also directed to methods of distinguishing EE from other disorders in a subject, wherein the methods comprise analyzing the sample from a patient to determine a level of one or more miRNAs associated with EE, determining whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE or with another disorder, and treating the patient with an appropriate therapeutic strategy based upon the diagnosis. In some embodiments, the other disorder is chronic esophagitis.

Embodiments of the invention are also directed to methods of determining whether a subject with EE has active EE or remission EE, wherein the methods comprise analyzing the sample from a patient to determine a level of one or more miRNAs associated with EE, determining whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with active EE or remission EE, and treating the patient with an appropriate therapeutic strategy based upon the diagnosis.

In embodiments of the invention, the one or more EE-associated miRNAs are selected from the list of genes dysregulated in EE provided in FIG. 1.

In some embodiments, at least one miRNA is selected from FIG. 1. In some embodiments the at least one miRNA includes miR-21. In some embodiments, at least one miRNA is selected from FIG. 1. In some embodiments the at least one miRNA includes miR-21. In some embodiments the at least one miRNA includes miR-223. In some embodiments the at least one miRNA includes miR-375. In some embodiments the at least one miRNA includes miR-146a. In some embodiments the at least one miRNA includes miR-146b.

In some embodiments, at least 2 miRNAs are selected from FIG. 1. In some embodiments, at least 3 miRNAs are selected from FIG. 1. In some embodiments, at least 4 miRNAs are selected from FIG. 1. In some embodiments, at least 5 miRNAs are selected from FIG. 1. In some embodiments, at least 10 miRNAs are selected from FIG. 1. In some embodiments, at least 15 miRNAs are selected from FIG. 1. In some embodiments, at least 20 miRNAs are selected from FIG. 1. In some embodiments, at least 25 miRNAs are selected from FIG. 1. In some embodiments, at least 30 miRNAs are selected from FIG. 1. In some embodiments, all of the miRNAs are selected from FIG. 1.

In some embodiments, 1, 2, 3, 4, 5, 6, 7, 8, or 9 miRNAs are selected from FIG. 1. In some embodiments, 10, 11, 12, 13, 14, 15, 16, 17, 18, or 19 miRNAs are selected from FIG. 1. In some embodiments, 20, 21, 22, 23, 24, 25, 26, 27, 28, or 29 miRNAs are selected from FIG. 1. In some embodiments, 30, 31, or 32 miRNAs are selected from FIG. 1.

In some embodiments, anywhere between 1 to 10 miRNAs are selected from FIG. 1. In some embodiments, anywhere between 1-20 miRNAs are selected from FIG. 1. In some embodiments, anywhere between 1-30 miRNAs are selected from FIG. 1.

In some embodiments, the miRNAs associated with EE are measured using one or more methods and/or tools, including for example, but not limited to, Taqman (Life Technologies, Carlsbad, Calif.), Light-Cycler (Roche Applied Science, Penzberg, Germany), ABI fluidic card (Life Technologies), NanoString® (NanoString Technologies, Seattle, Wash.), NANODROP® technology (Thermo Fisher Scientific (Wilmington, Del.), fluidic card, and the like. The person of skill in the art will recognize such other formats and tools, which can be commercially available or which can be developed specifically for such analysis.

Determination of the miRNA level(s) as described herein can be combined with determination of the levels of one or more non-miRNA biomarkers associated with EE. For example, determination of the miRNA level(s) as described herein can be combined with determination of the levels of one or more genes of the EE transcriptome. Such a determination can include measurement of the gene DNA or RNA, or the gene product. Such genes can include, for example, eotaxin-3, and the like.

Embodiments of the invention are also directed to methods of treating an eosinophilic disorder (other than EE) in a patient, wherein the methods comprise analyzing the sample from a patient to determine a level of one or more miRNAs associated with an eosinophilic disorder, determining whether the level of the one or more miRNAs is up-regulated or down-regulated relative to a level of the one or more miRNAs measured in a normal individual, wherein the presence of an elevated or reduced level of one or more miRNAs associated with an eosinophilic disorder results in the patient being diagnosed with an eosinophilic disorder, and treating the patient with an appropriate therapeutic strategy based upon the diagnosis. Eosinophilic disorders other than EE include, for example, eosinophilic gastrointestinal disorder (EGID) outside of the esophagus, asthma, and the like. In embodiments of the invention, miRNAs associated with asthma include miR375. The method of claim 29, wherein the one or more miRNAs associated with asthma comprises miR375. In some embodiments, the sample comprises lung and/or lung epithelial cells.

EE Therapies

Certain embodiments of the invention involve administering EE therapies, including allergen removal, steroid treatment, dietary management, and the combination of steroid treatment and dietary management. EE therapies also include the use of proton pump inhibitors (PPIs), topical glucocorticoids, such as fluticasone, budesonide, or ciclesonide, humanized antibodies against relevant cytokines and/or mediators, such as eotaxin-1, eotaxin-3, IL-13, IL-5, IL-5Rα, CD49D, SIGLEC-8, IgE, CD300A, TSLP, and/or IL-33, small molecule inhibitors of an eosinophil and/or allergic disease activation pathway, such as a notch-signaling inhibitor or an inhibitor or antagonist of CCR3, CCL11, VLA4, $CRT_H2$, prostaglandin D2, histamine H4 receptor, IL-13, IL-4, and/or the common β chain, and small molecule inhibitors capable of modulating miRNA levels and/or as severing as stem-loop processing inhibitors.

In some embodiments, EE can be treated through the blockade of eosinophil recruitment, such as through CCR3 and/or CCL11 inhibition, adhesion molecule inhibition, CRTH2 and prostaglandin D2 inhibition, histamine H4 receptor inhibition, IL-13 and/or IL-4 blockade, and the like. Compounds that can be used for these purposes include, for example, small molecule CCR3 antagonists and/or eotaxin-1-specific antibodies for CCR3 and/or CCL11 inhibition, CD49D-specific antibodies and/or small molecule VLA4 antagonists for adhesion molecule inhibition, $CRT_H2$ antagonists for $CRT_H2$ and prostaglandin D2 inhibition, small molecule histamine H4 receptor antagonists for histamine H4 receptor inhibition, and IL-13-specific antibodies, IL-4Rα antagonists, IL-4 variants for IL-13 and/or IL-4 blockade, and the like. Specific examples of such compounds include, for example, small molecule CCR3 antagonists, such as LH31407, eotaxin-1-specific antibodies, such as bertilimumab, CD49D-specific antibodies, such as natalizubam, small molecule VLA4 antagonists, such as compound 1, $CRT_H2$ antagonists, such as Ser. No. 00/000,459, small molecule histamine H4 receptor antagonists, such as 1NCB38579, IL-13-specific antibodies, such as lebrikizumab, IL-4Rα antagonists, such as AMG 317, IL-4 variants, such as pitrakinra, and the like.

In some embodiments, EE can be treated through the inhibition of eosinophil survival, such as through IL-5 and/or IL-5Rα blockade, SIGLEC-8 agonism, IgE blockade, activation of inhibitory receptors, TSLP inhibition, and the like. Compounds that can be used for these purposes include, for example, IL-5-specific antibodies, IL-5Rα-specific antibodies, and/or antisense oligonucleotides directed against the common β chain for IL-5 and/or IL-5Rα blockade, SIGLEC-8-specific antibodies for SIGLEC-8 agonism, IgE-specific antibodies for IgE blockade, CD300A-specific antibodies for activation of inhibitory receptors, TSLP-specific antibodies for TSLP inhibition, and the like. Specific examples of such compounds include, for example, IL-5-specific antibodies, such as mcpolizumab and reslizumab, IL-5Rα-specific antibodies, such as benralizumab, antisense oligonucleotides directed against the common β chain, such as TPI ASM8, SIGLEC-8-specific antibodies, IgE-specific antibodies, such as omalizumab, CD300A-specific antibodies, TSLP-specific antibodies, such as AMG 157, and the like In some embodiments, EE can be treated through the inhibition of eosinophil activation, such as through IL-33 blockade, notch inhibition, and the like. Compounds that can be used for these purposes include, for example, IL-33-specific antibodies for IL-33 blockade, notch signaling inhibitors for notch inhibition, and the like. Specific examples of such compounds include, for example, IL-33-specific antibodies, notch signaling inhibitors, such as semagacestat, and the like In some embodiments, EE can be treated through the blockade of eosinophil production, such as through IL-5R blockade, and the like. Compounds that can be used for these purposes include, for example, IL-5Rα-specific antibodies for IL-5R blockade, and the like. Specific examples of such compounds include, for example, IL-5Rα-specific antibodies, such as benralizumab, and the like.

Certain embodiments of the invention involve using miRNAs or modified miRNAs as therapeutic targets or agents. For example, any miRNA(s) associated with EE found to be elevated relative to the level(s) of the one or more miRNAs measured in a normal individual or using one or more corresponding modified miRNA(s) can be used as a therapeutic target or agent.

In some embodiments, EE can be treated by modulating one or more miRNAs via one or more of a number of approaches, including the use of anti-miRNA oligonucleotides (antagomirs, or AMOs), antisense oligonucleotides (ASOs), locked nucleic acids (LNAs) which modify miRNAs or serve as modified antisense oligonucleotides, RNA competitive inhibitors or decoys (miRNA sponges), small molecule inhibitors of miRNA stem-loop processing, and viral vectors expressing one or more miRNA genes, including lentiviral vectors (LVs), adenoviral vectors (AVs), and adeno-associated virus (AAV), and the like. For example, EE therapy can involve the administration of an antagomir directed against a miRNA found to be elevated relative to the level(s) of the one or more miRNAs measured in a normal individual, a miR-21, miR-223, miR-146a, and/or miR-146b antagomir, an IGF1 or IGF1R inhibitor, such as NVP-AEW541 and/or pricopodophyllin, and the like.

The example targeting strategies and compounds presently provided are intended to be representative. One of skill in the art will recognize that different compounds from those listed above can be used to achieve a comparable outcome and how to identify such compounds.

Competitive antagonists of a given miRNA can be generated using previously described techniques (Krutzfeldt J. et al. *Nature*. 438:685-9 (2005); Burnett, J. and Rossi, *J. Chem. Biol.* 19:60-71 (2012); van Rooij, E. et al. *Circ. Res.* 110:496-507 (2012)); these include modification of the phosphorothioate (PS) backbone, LNA modification, chemical substitution at the 2'-position of the sugar ring, cholesterol conjugation at the 3' or 5' end through a hydroxyprolinol linkage, and use of a "guide strand" designed to mimic the miRNA of interest, and the like. The chemistry involved in the targeting of miRNAs is the same as that involved in other RNA-directed therapies, such as siRNA, shRNA, and the like, and the relevant issues relating to drug delivery are the same.

Heretofore unknown anti-miRNA therapeutics can be developed by the screening of various compounds. Compounds that can be screened to determine their utility as anti-miRNA therapeutics include for example, but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular libraries made of D- or L-configuration amino acids, or both, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), organic and inorganic molecules, and the like.

In addition to the more traditional sources of test compounds, computer modeling and searching technologies permit the rational selection of test compounds by utilizing structural information from the ligand binding sites relevant proteins. Such rational selection of test compounds can decrease the number of test compounds that must be screened in order to identify a therapeutic compound. Knowledge of the sequences of relevant proteins allows for the generation of models of their binding sites that can be used to screen for potential ligands. This process can be accomplished in several manners known in the art. A preferred approach involves generating a sequence alignment of the protein sequence to a template (derived from the crystal structures or NMR-based model of a similar protein(s), conversion of the amino acid structures and refining the model by molecular mechanics and visual examination. If a strong sequence alignment cannot be obtained then a model can also be generated by building models of the hydrophobic helices. Mutational data that point towards residue-residue contacts can also be used to position the helices relative to each other so that these contacts are achieved. During this process, docking of the known ligands into the binding site cavity within the helices can also be used to help position the helices by developing interactions that would stabilize the binding of the ligand. The model can be completed by refinement using molecular mechanics and loop building using standard homology modeling techniques. (General information regarding modeling can be found in Schoneberg, T. et. al. *Molecular and Cellular Endocrinology* 151:181-93 (1999); Flower, D. *Biochimica et Biophysica Acta* 1422:207-34 (1999); and Sexton, P. *Current Opinion in Drug Discovery and Development* 2:440-8 (1999).)

Once the model is completed, it can be used in conjunction with one of several existing computer programs to narrow the number of compounds to be screened by the screening methods of the present invention, like the DOCK program (UCSF Molecular Design Institute, San Francisco, Calif.). In several of its variants it can screen databases of commercial and/or proprietary compounds for steric fit and rough electrostatic complementarity to the binding site. Another program that can be used is FLEXX (Tripos Inc., St. Louis, Mo.).

Chronic Esophagitis Therapies

Any anti-gastroesophgeal reflux disease (GERD) therapy can be used to treat chronic esophagitis. There are various definitions of GERD; some include esophagitis (histological finding of epithelial hyperplasia with acute non-eosinophilic inflammation), others are purely clinical (heartburn), and others are based on measurement of esophageal acid levels (e.g. pH probes). Accordingly, GERD and chronic (non-eosinophilic) esophagitis can be considered to be equivalent as a first approximation, and anti-GERD therapies can be used to treat chronic esophagitis.

Anti-GERD therapies include, for example, antacid administration, H2 agonist administration, and/or PPI therapy, and the like. Certain embodiments of the invention involve administering chronic esophagitis therapies, including antacid administration, H2 agonist administration, and/or PPI therapy.

Administration

The miRNAs, modified miRNAs, or anti-miRNAs used as therapeutic targets or agents can be administered via oral or parenteral delivery routes (subcutaneous or intravenous), as has been described previously (van Rooij, E. et al. *Circ. Res.* 110:496-507 (2012)). Such therapeutics can be administered by any pharmaceutically acceptable carrier, including, for example, any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional medium or agent is incompatible with the active compound, such media can be used in the compositions of the invention. Supplementary active compounds can also be incorporated into the compositions. A pharmaceutical composition of the invention is formulated to be compatible with its intended route of administration. Routes of administration include for example, but are not limited to, intravenous, intramuscular, and oral, and the like. Additional routes of administration include, for example, sublingual, buccal, parenteral (including, for example, subcutaneous, intramuscular, intraarterial, intradermal, intraperitoneal, intracisternal, intravesical, intrathecal, or intravenous), transdermal, oral, transmucosal, and rectal administration, and the like.

Solutions or suspensions used for appropriate routes of administration, including, for example, but not limited to parenteral, intradermal, or subcutaneous application, and the like, can include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose, and the like. The pH can be adjusted with acids or bases, such as, for example, hydrochloric acid or sodium hydroxide, and the like. The parenteral preparation can be enclosed in, for example, ampules, disposable syringes, or multiple dose vials made of glass or plastic, and the like.

Pharmaceutical compositions suitable for injectable use include, for example, sterile aqueous solutions (where water soluble) or dispersions and sterile powders for the extemporaneous preparation of sterile injectable solutions or dispersion, and the like. For intravenous administration, suitable carriers include, for example, physiological saline, bacteriostatic water, Cremophor EL™ (BASF, Parsippany, N.J.) or phosphate buffered saline (PBS), and the like. In all cases, the composition should be fluid to the extent that easy syringability exists. The carrier can be a solvent or dispersion medium containing, for example, water, ethanol, polyol (for example, glycerol, propylene glycol, and liquid polyethylene glycol, and the like), and suitable mixtures thereof, and the like. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, such as, for example, parabens, chlorobutanol, phenol, ascorbic acid, thimerosal, and the like. In many cases, it can be preferable to include isotonic agents, such as, for example, sugars, polyalcohols such as mannitol, sorbitol, and sodium chloride, and the like, in the composition. Prolonged absorption of the injectable compositions can be brought about by including in the composition an agent which delays absorption such as, for example, aluminum monostearate and gelatin, and the like.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets, for example. For oral administration, the agent can be contained in enteric forms to survive the stomach or further coated or mixed to be released in a particular region of the gastrointestinal (GI) tract by known methods. For the purpose of oral therapeutic administration, the active compound can be incorporated with excipients and used in the form of tablets, troches, or capsules, or the like. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following exemplary ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate; a glidant such as colloidal silicon dioxide; a sweetening agent such as sucrose or saccharin; or a flavoring agent such as peppermint, methyl salicylate, or orange flavoring, or the like.

For administration by inhalation, the compounds can be delivered in the form of an aerosol spray from pressured container or dispenser, which contains a suitable propellant, e.g., a gas such as carbon dioxide, or a nebulizer, or the like.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives, and the like. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems, and the like. Biodegradable, biocompatible polymers can be used, such as, for example, ethylene vinyl acetate, polyanhydrides, polyglycolic acid, collagen, polyorthoesters, and polylactic acid, and the like. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference in its entirety.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The details for the dosage unit forms of the invention are dictated by and directly dependent on the unique characteristics of the active compound and the particular therapeutic effect to be achieved, and the limitations inherent in the art of compounding such an active compound for the treatment of individuals. Such details are known to those of skill in the art.

Certain embodiments of the invention include using quantification data from a gene-expression analysis and/or from a miRNA analysis, either from an esophageal biopsy sample, or from a sample of esophageal mucosa, or from a blood sample. Embodiments of the invention include not only methods of conducting and interpreting such tests but also include reagents, kits, assays, and the like, for conducting the tests.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of subjects with a positive test result who are correctly diagnosed; for tests with a high PPV, a positive test indicates the presence of the condition in question. The NPV of a particular diagnostic test represents the proportion of subjects with a negative test result who are correctly diagnosed; for tests with a high NPV, a negative test indicates the absence of the condition. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition.

The correlations disclosed herein, between EE and miRNA levels and/or mRNA levels and/or gene expression levels, provide a basis for conducting a diagnosis of EE, or for enhancing the reliability of a diagnosis of EE by combining the results of a quantification of miRNA with results from other tests or indicia of EE. For example, the results of a quantification of miRNA could be combined with the results of a quantification of one or more cytokines or mRNAs. Thus, even in situations in which a given miRNA, cytokine, or mRNA correlates only moderately or weakly with EE, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

The disclosure, figures, and tables herein make mention of statistical significance and "p values." While p values below 0.05 are considered to be statistically significant, it is within the scope of embodiments of the present invention to make use of correlations having a reported p value above 0.05 as well as below 0.05. For example, in a study having a small sample size but a genuine correlation, a p value can be above 0.05, such as, for example, 0.06, 0.07, 0.08, 0.09, 0.10, 0.15, or more. Since p value is affected by sample size, two studies can have the same proportion of outcomes, and a study with a smaller sample size can have a p value above 0.05, while the study with the larger sample size can have a p value below 0.05, even though the correlation is proportionally the same. Thus, while a p value below 0.05, for any sample size, is a strong indication of a statistically significant correlation, a genuine correlation can exist, that is tested with a small sample size, and the p value of such a test can be above 0.05.

The illustrative embodiments described in the detailed description, drawings, and claims are not meant to be limiting. Having described the invention in detail, it will be apparent that modifications, variations, and equivalent embodiments are possible without departing from the spirit or scope of the subject matter presented herein.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1 miRNA Expression Profiling in EE Patients

A study was undertaken to identify miRNAs that are differentially expressed in EE patients. Esophageal biopsy samples from EE patients and normal controls were analyzed for their miRNA expression profiles, as described below.

Human Esophageal Tissues

Patients were selected without regard to age, race, or sex. Normal patients had symptoms consistent with gastroesophageal reflux disease or EE, but endoscopic and histologic appearances were normal (Abonia, J. et al. *J. Allergy Clin. Immunol.* 126:140-9 (2010)). The inclusion criteria for active EE patients included a clinical diagnosis of EE and eosinophil counts of >24 per 400× high power field (hpf) in the esophageal biopsies; most patients had lack of response to proton pump inhibitor (PPI) therapy (Table 1). The inclusion criteria for active chronic esophagitis patients include a clinical diagnosis of esophagitis and eosinophil counts of 1-15 per 400× hpf in the esophageal biopsies.

Patients with systemic or swallowed topical glucocorticoid use were excluded from the selection of active EE or active chronic esophagitis patients. The inclusion criteria for EE patients responding to glucocorticoid treatment included a history of EE, treatment with swallowed topical glucocorticoid, response as indicated by eosinophil count <2 per 400× hpf, and normalization of histological features of the disease. The EE patients not responding to glucocorticoid treatment had a history of EE, treatment with swallowed topical glucocorticoid, and lack of response as indicated by esophageal eosinophil count >24 per 400× hpf in biopsies obtained at follow-up visits after therapy. These patient characteristics are listed in Table 1.

TABLE 1

Patient clinical characteristics.

| | Normal | EE | Chronic Esophagitis | EE Responding to Steroids | EE not Responding to Steroids |
|---|---|---|---|---|---|
| # of Patients | 23 | 31 | 9 | 20 | 8 |
| Male, n (%) | 11 (48) | 23 (74) | 7 (78) | 16 (80) | 6 (75) |
| Age (yr) | | | | | |
| Mean | 9.26 | 9.29 | 9.06 | 8.32 | 10.96 |
| Range | 1.43-19.01 | 1.89-32.26 | 4.5-16.12 | 3.75-19.43 | 4.3-16.41 |
| Medications | | | | | |
| PPI, n (%)* | 6 (26) | 23 (74) | 2 (22) | 16 (80) | 7 (88) |
| Steroids, n (%) | 0 | 0 | 0 | 20 (100) | 8 (100) |

*The percentages listed reflect total number of patients studied who had taken at least 8 weeks of PPI therapy prior to a diagnostic endoscopy.

Eight normal controls, 10 active EE patients, 5 chronic esophagitis patients, and 6 EE patients responding to glucocorticoid treatment were included in the microarray analysis. The remaining patients were included in the quantitative PCR (qPCR) studies only.

Patients were selected for miRNA microarray analysis and qPCR studies based on systematic enrollment. Patients enrolled in this study between November 2007 and July 2009 were included in the microarray analysis. Additional patients enrolled between July 2009 and June 2011 who met the inclusion criteria and had RNA samples that passed the RNA quality analysis were included in the PCR analysis.

RNA Extraction and miRNA Microarray Analysis

Total RNA, including miRNA, from patient esophageal biopsy samples was isolated using the miRNeasy Mini Kit (Qiagen, Valencia, Calif.), according to the manufacturer's instructions. RNA quality was assessed using the 2100 Bioanalyzer (Agilent Technologies, Santa Clara, Calif.), and only samples with RNA integrity number >8 were included in the analyses. MiRNA expression was profiled using the TaqMan Human MicroRNA Array v2.0 (Applied Biosystems, Carlsbad, Calif.), which includes probes for 667 human miRNAs, as annotated in release 10.0 of the miRBase microRNA Registry (Griffiths-Jones, S. et al. *Nucleic Acids Res.* 34:D140-4 (2006)), according to the manufacturer's protocols (Applied Biosystems). Data analyses were carried out using GeneSpring software (Agilent Technologies). The microarray data have been deposited into the Array Express database, found at http <colon slash slash> www <dot> ebi <dot> ac <dot> uk <slash> arrayexpress, with accession number E-MEXP-3298, in compliance with minimum information about microarray experiment (MI-AME) standards.

MiRNAs differentially regulated between healthy control and EE patients were identified by normalizing the expression data to the average of two endogenous control probes, namely U6 and RNU44, then filtered on cycle threshold values <30 and at least a 2-fold change between normal controls and EE patients. Statistical significance was determined at P<0.05 with Benjamini Hochberg false discovery rate correction. The list of differentially expressed miRNAs was clustered using hierarchical clustering, and a heatmap was generated. Similar analyses were carried out comparing normal controls to chronic esophagitis patients, and patients that did not received glucocorticoid treatment to patients that received glucocorticoid treatment to identify differentially expressed miRNAs between the groups.

qRT-PCR for miRNA

Levels of miRNA expression were measured quantitatively via the TaqMan MicroRNA Assays (Applied Biosystems). The expression levels were then normalized to the U6 endogenous control. Relative expression was calculated using the comparative Ct method (Livak, K. et al. *Method.* 25:402-8 (2001)).

Results

Esophageal biopsy specimens from patients with EoE and healthy control subjects were profiled with the TaqMan Human miRNA Array V2.0, comprising 677 miRNAs, as annotated in version 10 of the miRBase registry, to identify miRNAs differentially expressed in patients with EoE (Griffiths-Jones, S. et al. *Nucleic Acids Res.* 36:D154-8 (2008)). Of the 677 miRNAs assayed, 254 miRNAs were expressed above background levels (Table 2). A comparison between normal controls and EE patients identified 21 up-regulated and 11 down-regulated miRNAs (FIG. 1). The most up-regulated miRNAs included miR-21 and miR-223, and the most down-regulated miRNA was miR-375.

Figure 2A:
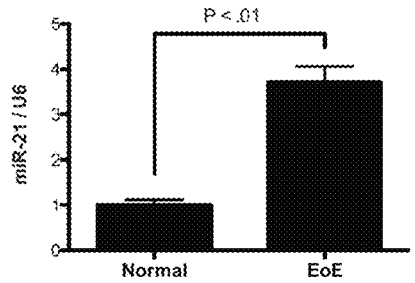
FIGS. 2A-F depict quantitative real time polymerase chain reaction (qRT-PCR) verification of a selected set of differentially expressed miRNAs in normal patients and EE patients. The graphs in FIGS. 2A-E depict the expression of 5 miRNAs, namely (2A) miR-21, (2B) miR-223, (2C) miR-375, (2D) let-7c, and (2E) miR-203. Their relative expression levels were normalized to U6 small nuclear RNA (U6).
Figure 2B:
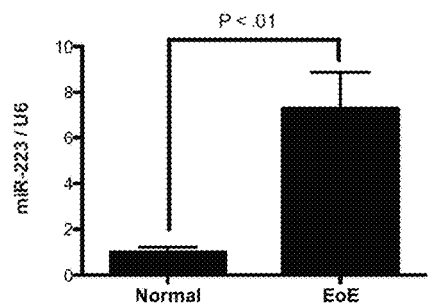
Figure 2C:
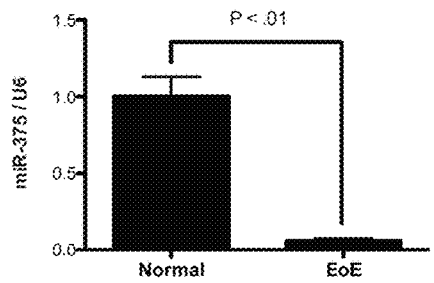
Figure 2D:
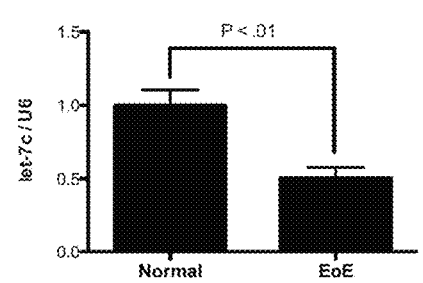
Figure 2E:
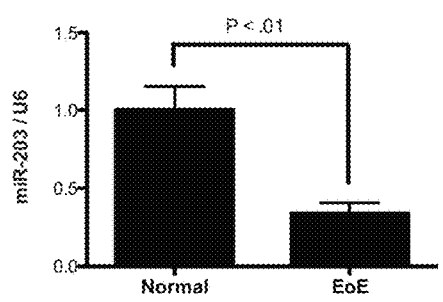
Figure 2F:
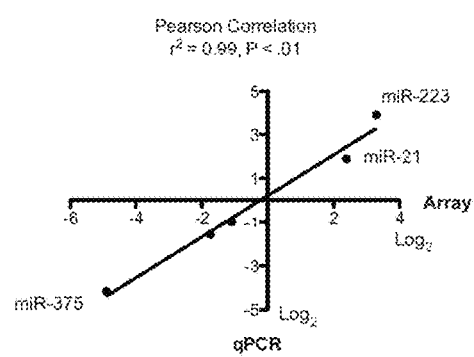

The differentially expressed miRNAs were evaluated by performing quantitative real time polymerase chain reaction (qRT-PCR) on a selected set of differentially expressed miRNAs, including miR-21, miR-223, miR-375, let-7c, and miR-203 (FIG. 2A-E). There was a strong correlation between the qRT-PCR and microarray data, with a Pearson correlation coefficient of 0.99 and p<0.01 (FIG. 2F).

TABLE 2

Log$_2$ fold change of all miRNAs expressed above background levels.

| Gene Symbol | Normal | Chronic Esophagitis | EE | Fluticasone Responders |
|---|---|---|---|---|
| U6 | 0.005 | 0.010 | 0.070 | −0.065 |
| RNU24 | 0.052 | −0.203 | 0.040 | 0.170 |
| RNU43 | −3.572 | −3.124 | −0.249 | 0.020 |
| RNU44 | −0.005 | −0.010 | −0.070 | 0.065 |
| RNU48 | −0.023 | −0.031 | 0.249 | 0.093 |
| RNU6B | 0.055 | −0.319 | −0.050 | −0.039 |
| hsa-let-7a | 0.046 | 0.026 | −0.019 | 0.007 |
| hsa-let-7b | 0.254 | 0.140 | −0.057 | −0.230 |
| hsa-let-7c | 0.114 | −0.092 | −0.973 | −0.099 |
| hsa-let-7d | 0.065 | 0.033 | 0.001 | 0.152 |
| hsa-let-7e | −0.074 | −0.141 | −0.390 | −0.103 |
| hsa-let-7f-2* | −0.033 | −0.259 | −0.153 | −0.109 |
| hsa-let-7f | −0.138 | 0.146 | −0.250 | 0.151 |
| hsa-let-7g | −0.005 | 0.261 | 0.089 | 0.553 |
| hsa-miR-1 | −0.960 | −1.173 | −2.695 | −2.563 |
| hsa-miR-100 | −0.027 | −0.144 | −0.602 | 0.333 |
| hsa-miR-101 | −0.029 | −0.117 | −0.060 | 0.353 |
| hsa-miR-103 | −0.099 | −0.178 | −0.184 | 0.254 |
| hsa-miR-106a | −0.155 | 0.034 | −0.055 | 0.189 |
| hsa-miR-106b* | −0.749 | 0.676 | 2.046 | 1.049 |
| hsa-miR-106b | −0.111 | 0.210 | 0.234 | 0.628 |
| hsa-miR-107 | 0.089 | 0.190 | −0.677 | 0.192 |

TABLE 2-continued

Log₂ fold change of all miRNAs expressed above background levels.

| Gene Symbol | Normal | Chronic Esophagitis | EE | Fluticasone Responders |
|---|---|---|---|---|
| hsa-miR-10a | 0.129 | −0.352 | −0.076 | −0.210 |
| hsa-miR-10b* | −0.172 | −0.278 | −0.183 | −0.199 |
| hsa-miR-10b | −0.258 | −0.063 | −0.083 | −0.029 |
| hsa-miR-125a-5p | −0.009 | −0.428 | 0.016 | −0.469 |
| hsa-miR-125b | 0.170 | 0.216 | −0.067 | 0.505 |
| hsa-miR-126* | 0.146 | −0.294 | −0.240 | 0.041 |
| hsa-miR-126 | 0.160 | −0.108 | −0.200 | −0.188 |
| hsa-miR-127 | 0.067 | −0.726 | −0.248 | −0.936 |
| hsa-miR-128a | 0.019 | 0.266 | 0.185 | 0.369 |
| hsa-miR-130a | 0.215 | 0.323 | 0.328 | 1.002 |
| hsa-miR-130b | −0.012 | 0.359 | 0.509 | 0.753 |
| hsa-miR-132 | 0.062 | 0.321 | 1.858 | −0.013 |
| hsa-miR-133a | −0.694 | −0.988 | −2.194 | −2.236 |
| hsa-miR-135a* | 0.163 | −0.495 | −0.379 | −0.780 |
| hsa-miR-135a | 0.278 | 0.607 | −0.381 | 0.505 |
| hsa-miR-135b* | 0.004 | 0.024 | 0.465 | 0.436 |
| hsa-miR-135b | 0.076 | 0.271 | −0.243 | 0.551 |
| hsa-miR-138-1* | 0.154 | −0.393 | 0.257 | −0.244 |
| hsa-miR-138 | −0.241 | −0.183 | 0.684 | −0.348 |
| hsa-miR-139-5p | 0.184 | −0.092 | −0.415 | 0.067 |
| hsa-miR-140-3p | 0.101 | −0.250 | 0.203 | −0.106 |
| hsa-miR-140 | 0.199 | −0.206 | 0.521 | −0.281 |
| hsa-miR-141 | −0.061 | 0.091 | −0.203 | 0.712 |
| hsa-miR-142-3p | 0.184 | 0.521 | 2.219 | 0.489 |
| hsa-miR-142-5p | −0.087 | 0.206 | 1.854 | 0.411 |
| hsa-miR-143 | 0.420 | −0.177 | −0.180 | −0.706 |
| hsa-miR-144* | −0.112 | −0.996 | −1.429 | 0.021 |
| hsa-miR-145* | 0.377 | −0.590 | −0.711 | −0.982 |
| hsa-miR-145 | 0.184 | −0.904 | −1.032 | −1.493 |
| hsa-miR-146a | 0.150 | 0.114 | 1.635 | −0.280 |
| hsa-miR-146b | 0.042 | 0.249 | 2.153 | −0.046 |
| hsa-miR-148a | −0.059 | 0.132 | −0.365 | 0.372 |
| hsa-miR-148b* | 0.072 | −0.064 | 0.174 | 0.140 |
| hsa-miR-148b | 0.024 | 0.067 | −0.033 | 0.292 |
| hsa-miR-149 | 0.021 | 0.007 | −0.366 | −0.230 |
| hsa-miR-150 | −0.143 | −0.156 | 0.692 | 0.155 |
| hsa-miR-15l-3p | 0.008 | −0.311 | 0.335 | 0.238 |
| hsa-miR-152 | 0.046 | −0.006 | 0.413 | 0.000 |
| hsa-miR-155 | −4.901 | −2.608 | −4.867 | 0.547 |
| hsa-miR-15a* | −0.096 | −0.469 | −0.102 | −0.108 |
| hsa-miR-15a | −0.157 | −0.097 | 0.677 | −5.024 |
| hsa-miR-15b* | −4.120 | −2.228 | −6.134 | 0.968 |
| hsa-miR-15b | −0.055 | 0.034 | 0.048 | 0.675 |
| hsa-miR-16-1* | −0.301 | −0.355 | 0.559 | −0.062 |
| hsa-miR-16 | −0.074 | −0.228 | −0.223 | −0.182 |
| hsa-miR-17* | −0.185 | −0.392 | −0.473 | 0.006 |
| hsa-miR-17 | −0.121 | 0.022 | −0.037 | 0.257 |
| hsa-miR-181a-2* | 0.021 | −0.356 | −0.905 | 0.052 |
| hsa-miR-181a | 0.262 | 0.375 | 0.407 | 0.511 |
| hsa-miR-182 | 0.125 | 0.342 | −0.595 | −0.155 |
| hsa-miR-183* | −0.243 | −0.314 | −1.218 | 0.182 |
| hsa-miR-183 | −0.077 | 0.052 | −0.637 | 0.135 |
| hsa-miR-185 | 0.071 | 0.091 | 0.930 | 0.226 |
| hsa-miR-186 | −0.203 | −0.496 | −0.586 | −0.520 |
| hsa-miR-188-5p | 0.198 | −0.605 | 0.261 | −0.333 |
| hsa-miR-18a | 0.067 | 0.444 | 0.787 | 0.426 |
| hsa-miR-18b | −3.585 | −1.188 | −3.780 | 0.876 |
| hsa-miR-190 | −0.061 | 0.336 | −0.107 | 0.804 |
| hsa-miR-191 | 0.049 | −0.127 | 0.013 | −0.034 |
| hsa-miR-192 | 0.535 | 2.019 | 0.286 | 1.957 |
| hsa-miR-193a-3p | −0.119 | −0.791 | −1.513 | −0.406 |
| hsa-miR-193a-5p | −0.050 | −0.603 | −1.261 | −0.243 |
| hsa-miR-193b* | −1.347 | −1.035 | −7.696 | 0.082 |
| hsa-miR-193b | 0.048 | −0.346 | −1.910 | −0.190 |
| hsa-miR-194 | 0.487 | 2.388 | 0.125 | 1.506 |
| hsa-miR-195 | 0.157 | −0.176 | −0.034 | −0.107 |
| hsa-miR-197 | 0.001 | −0.021 | 0.137 | 0.306 |
| hsa-miR-199a-3p | 0.160 | −0.182 | 0.327 | −0.202 |
| hsa-miR-19a | −0.010 | 0.123 | 0.288 | 0.119 |
| hsa-miR-19b-1* | 0.027 | 0.074 | 0.379 | 0.169 |
| hsa-miR-19b | 0.005 | 0.022 | 0.071 | 0.222 |
| hsa-miR-200a* | 0.056 | −0.064 | 0.066 | 0.210 |
| hsa-miR-200a | 0.036 | 0.220 | 0.003 | 0.476 |
| hsa-miR-200b* | −0.105 | −0.157 | −0.270 | 0.400 |
| hsa-miR-200b | −0.063 | 0.036 | −0.409 | 0.247 |
| hsa-miR-200c | 0.017 | 0.233 | −0.240 | 0.126 |
| hsa-miR-203 | −0.059 | −0.324 | −1.843 | 0.099 |
| hsa-miR-204 | −0.035 | 1.078 | −1.204 | 0.139 |
| hsa-miR-205 | −0.159 | −0.037 | −0.283 | −0.227 |
| hsa-miR-20a* | 0.020 | −0.282 | −0.181 | 0.088 |
| hsa-miR-20a | −0.001 | 0.140 | 0.047 | 0.325 |
| hsa-miR-20b | 0.028 | −0.086 | 0.094 | 0.022 |
| hsa-miR-21* | 0.019 | 0.506 | 2.639 | 0.227 |
| hsa-miR-21 | −0.058 | 0.840 | 2.332 | 0.596 |
| hsa-miR-210 | 0.038 | −0.240 | −1.570 | 0.200 |
| hsa-miR-211 | −0.099 | −0.728 | −2.985 | −0.028 |
| hsa-miR-212 | 0.005 | 0.377 | 1.914 | 0.290 |
| hsa-miR-214 | 0.158 | −0.554 | 0.644 | −0.686 |
| hsa-miR-215 | −0.516 | 1.547 | −3.082 | 1.916 |
| hsa-miR-218 | 0.090 | −0.234 | −0.494 | 0.193 |
| hsa-miR-22* | −0.186 | −0.621 | −0.697 | −0.010 |
| hsa-miR-22 | −1.148 | 1.084 | 0.308 | 1.058 |
| hsa-miR-221 | −0.144 | −0.172 | 0.286 | −0.085 |
| hsa-miR-222* | −0.076 | −0.093 | 1.057 | −0.063 |
| hsa-miR-222 | 0.071 | 0.118 | 0.425 | −0.019 |
| hsa-miR-223* | 0.249 | −0.076 | 3.303 | 0.183 |
| hsa-miR-223 | 0.042 | 0.125 | 3.348 | 0.223 |
| hsa-miR-224 | −0.024 | −0.066 | −0.455 | 0.259 |
| hsa-miR-23b | 0.040 | 0.084 | −0.265 | −0.169 |
| hsa-miR-24 | −0.067 | −0.062 | −0.317 | 0.165 |
| hsa-miR-25 | −0.084 | 0.041 | 0.303 | 0.342 |
| hsa-miR-26a-1* | 0.074 | −0.096 | 0.081 | 0.184 |
| hsa-miR-26a-2* | 0.025 | −0.433 | 1.020 | 0.434 |
| hsa-miR-26a | 0.004 | 0.017 | −0.132 | 0.336 |
| hsa-miR-26b* | 0.082 | −0.131 | 0.375 | 0.114 |
| hsa-miR-26b | −0.024 | 0.024 | −0.115 | 0.367 |
| hsa-miR-27a* | −0.027 | −0.220 | 0.338 | 0.153 |
| hsa-miR-27a | −0.081 | 0.151 | 0.376 | 0.414 |
| hsa-miR-27b* | −0.079 | −0.130 | 0.756 | 0.027 |
| hsa-miR-27b | −0.074 | 0.227 | 0.330 | 0.514 |
| hsa-miR-28-3p | −0.114 | −0.221 | −0.164 | 0.146 |
| hsa-miR-28 | −0.120 | −0.187 | 0.245 | 0.067 |
| hsa-miR-296 | −0.114 | 0.207 | −0.397 | 0.756 |
| hsa-miR-29a* | −0.054 | −0.524 | 0.511 | −0.266 |
| hsa-miR-29a | 0.292 | 0.414 | 1.205 | 0.441 |
| hsa-miR-29b | 0.120 | 0.391 | 1.290 | 0.761 |
| hsa-miR-29c* | 0.119 | −0.226 | 0.207 | −0.057 |
| hsa-miR-29c | −0.166 | 0.085 | −0.067 | 0.671 |
| hsa-miR-301 | 0.028 | 0.035 | 0.241 | 0.084 |
| hsa-miR-301b | −0.105 | 0.141 | 0.492 | 0.312 |
| hsa-miR-30a-3p | 0.300 | −0.599 | −0.900 | −0.349 |
| hsa-miR-30a-5p | 0.254 | −0.368 | −0.345 | 0.221 |
| hsa-miR-30b | −0.129 | −0.103 | −0.399 | 0.371 |
| hsa-miR-30c | −0.005 | −0.013 | −0.364 | 0.220 |
| hsa-miR-30d* | 0.011 | −0.322 | −0.010 | 0.255 |
| hsa-miR-30d | 0.283 | −0.406 | −0.138 | 0.155 |
| hsa-miR-30e-3p | 0.139 | −0.532 | −0.413 | −0.190 |
| hsa-miR-30e | 0.120 | −0.367 | −0.194 | 0.070 |
| hsa-miR-31 | −0.183 | 0.077 | −0.961 | −0.117 |
| hsa-miR-32 | 0.017 | 0.297 | −0.142 | 0.299 |
| hsa-miR-320 | −0.119 | −0.229 | −0.331 | −0.101 |
| hsa-miR-324-3p | 0.024 | 0.003 | −0.348 | 0.121 |
| hsa-miR-324-5p | −0.038 | 0.256 | 0.109 | 0.583 |
| hsa-miR-328 | 0.270 | −0.074 | −0.150 | −0.043 |
| hsa-miR-331 | 0.094 | 0.230 | −0.152 | 0.418 |
| hsa-miR-335* | −0.246 | −0.405 | −0.215 | 0.413 |
| hsa-miR-335 | −0.098 | −0.256 | 0.065 | 0.143 |
| hsa-miR-339-3p | −0.094 | −0.140 | −0.094 | 0.037 |
| hsa-miR-339-5p | −0.070 | 0.592 | 1.144 | 1.286 |
| hsa-miR-33a* | −0.059 | −0.031 | −0.097 | 0.062 |
| hsa-miR-340* | −0.080 | −0.299 | 0.439 | 0.018 |
| hsa-miR-340 | −0.068 | 0.209 | 0.793 | 0.139 |
| hsa-miR-342-3p | −0.021 | 0.043 | 0.754 | −0.007 |
| hsa-miR-345 | −0.110 | 0.214 | 0.626 | 0.297 |
| hsa-miR-34a* | −0.044 | −0.492 | 0.141 | −0.140 |
| hsa-miR-34a | −0.090 | −0.132 | 0.000 | 0.295 |
| hsa-miR-34c | 0.746 | −0.396 | 3.306 | 0.526 |
| hsa-miR-361 | 0.020 | 0.362 | 0.272 | 0.389 |
| hsa-miR-362-3p | 0.064 | 0.079 | 0.143 | 0.310 |
| hsa-miR-362 | 0.006 | 0.136 | 0.016 | 0.076 |

TABLE 2-continued

Log₂ fold change of all miRNAs expressed above background levels.

| Gene Symbol | Normal | Chronic Esophagitis | EE | Fluticasone Responders |
|---|---|---|---|---|
| hsa-miR-365 | −0.044 | −0.564 | −1.684 | −0.107 |
| hsa-miR-374 | −0.017 | −0.035 | −0.177 | 0.154 |
| hsa-miR-374-5p | 0.025 | 0.145 | −0.151 | 0.427 |
| hsa-miR-375 | −0.032 | −0.363 | −4.953 | 0.073 |
| hsa-miR-376c | 0.455 | −0.335 | 0.399 | −0.088 |
| hsa-miR-378 | −0.115 | −0.311 | −0.219 | 0.220 |
| hsa-miR-378 | 0.011 | −0.378 | 0.025 | 0.124 |
| hsa-miR-380-5p | −0.109 | −0.638 | 0.067 | −0.462 |
| hsa-miR-411 | 0.028 | −0.413 | −0.433 | −0.746 |
| hsa-miR-422a | −0.006 | 0.030 | 0.210 | −0.079 |
| hsa-miR-423-5p | −0.065 | −0.254 | 0.194 | 0.221 |
| hsa-miR-425* | −0.008 | 0.205 | 0.871 | 0.278 |
| hsa-miR-425-5p | 0.021 | 0.367 | 0.419 | 0.443 |
| hsa-miR-429 | 0.041 | 0.266 | −0.125 | 0.463 |
| hsa-miR-451 | −0.179 | −0.586 | −1.137 | 0.210 |
| hsa-miR-452 | 0.070 | 0.051 | −0.338 | 0.248 |
| hsa-miR-454 | −0.074 | 0.055 | 0.436 | −0.100 |
| hsa-miR-455-3p | −0.105 | 0.274 | 0.742 | 0.478 |
| hsa-miR-455 | 0.084 | 0.246 | 0.605 | 0.535 |
| hsa-miR-483-5p | 0.751 | 0.744 | 0.759 | −0.391 |
| hsa-miR-484 | 0.031 | −0.202 | 0.070 | 0.001 |
| hsa-miR-491 | 0.013 | −0.162 | −0.168 | 0.141 |
| hsa-miR-494 | 0.945 | 1.112 | 0.886 | 0.306 |
| hsa-miR-495 | −0.057 | −0.345 | −0.226 | −0.848 |
| hsa-miR-497 | 0.094 | −0.847 | −0.727 | −0.440 |
| hsa-miR-500 | −0.709 | −0.105 | −2.617 | 0.970 |
| hsa-miR-500 | −0.060 | 0.109 | 0.228 | 0.370 |
| hsa-miR-501 | 0.023 | 3.372 | 1.185 | 5.325 |
| hsa-miR-502-3p | −0.003 | −0.068 | 0.068 | 0.294 |
| hsa-miR-502 | −0.050 | 0.414 | 0.395 | 0.874 |
| hsa-miR-505* | 0.090 | −0.424 | 0.469 | −0.065 |
| hsa-miR-532-3p | −0.012 | −0.071 | −0.142 | 0.239 |
| hsa-miR-532 | 0.036 | −0.263 | −0.024 | −0.019 |
| hsa-miR-545 | 0.024 | 1.117 | 0.560 | 1.007 |
| hsn-miR-565 | 0.039 | −0.143 | 0.907 | 0.143 |
| hsa-miR-574-3p | 0.051 | −0.452 | −0.657 | −0.234 |
| hsa-miR-576-3p | −0.150 | −0.269 | −0.008 | 0.064 |
| hsa-miR-579 | −0.015 | 0.073 | −0.291 | 0.445 |
| hsa-miR-590-5p | 0.009 | −0.127 | 0.056 | 0.016 |
| hsa-miR-592 | −0.135 | 0.816 | 1.663 | 0.054 |
| hsa-miR-597 | 0.244 | 0.582 | 0.668 | 0.774 |
| hsa-miR-598 | 0.003 | 0.037 | −0.302 | 0.285 |
| hsa-miR-625* | 0.129 | −0.100 | 0.664 | 0.168 |
| hsa-miR-625 | 0.034 | 0.236 | 0.839 | 0.516 |
| hsa-miR-628-5p | 0.041 | 0.079 | 0.863 | −0.103 |
| hsa-miR-629 | −0.013 | −0.114 | −0.200 | 0.226 |
| hsa-miR-629 | −0.068 | −0.584 | −0.378 | 0.187 |
| hsa-miR-642 | −0.041 | 0.403 | 1.165 | 1.110 |
| hsa-miR-650 | 0.166 | −3.439 | 9.602 | 1.714 |
| hsa-miR-652 | 0.206 | 0.504 | 0.366 | 0.622 |
| hsa-miR-660 | −0.046 | 0.002 | 0.038 | 0.433 |
| hsa-miR-661 | 0.329 | −0.214 | 0.820 | −0.477 |
| hsa-miR-671-3p | 0.012 | 0.069 | 0.522 | 0.062 |
| hsa-miR-675 | 0.150 | −0.208 | −4.643 | 7.873 |
| hsa-miR-7-1* | −0.259 | −0.202 | 0.257 | 0.229 |
| hsa-miR-7 | 0.158 | 0.399 | 1.221 | 0.640 |
| hsa-miR-708 | 0.079 | −0.180 | −0.563 | 0.407 |
| hsa-miR-744* | −0.005 | −0.212 | −0.678 | 0.095 |
| hsa-miR-744 | 0.055 | 0.034 | −0.335 | 0.107 |
| hsa-miR-760 | 0.194 | −0.633 | −0.054 | −0.896 |
| hsa-miR-766 | −2.682 | −0.455 | 1.014 | 0.580 |
| hsa-miR-768-3p | −0.005 | −0.081 | 0.770 | 0.167 |
| hsa-miR-769-5p | −0.064 | −0.285 | 0.263 | 0.196 |
| hsa-miR-801 | 0.084 | −0.460 | 3.908 | −0.568 |
| hsa-miR-877 | 0.233 | −0.078 | 0.571 | −0.423 |
| hsa-miR-885-5p | −0.184 | 0.003 | −0.027 | 0.781 |
| hsa-miR-886-3p | −0.032 | −0.099 | 1.583 | −0.316 |
| hsa-miR-886-5p | 0.094 | 0.177 | 1.528 | −0.277 |
| hsa-miR-9 | −0.123 | 0.018 | −0.222 | 0.145 |
| hsa-miR-923 | 0.853 | 0.445 | −0.866 | −0.802 |
| hsa-miR-92a-1* | −0.333 | 0.151 | 1.129 | 0.872 |
| hsa-miR-92a | −0.052 | 0.107 | 0.198 | 0.491 |
| hsa-miR-93* | −0.051 | 0.006 | 0.242 | 0.308 |
| hsa-miR-93 | −0.008 | 0.004 | 0.385 | −0.081 |
| hsa-miR-942 | −0.347 | 0.008 | 0.164 | 0.530 |
| hsa-miR-944 | 0.007 | −0.182 | −0.081 | 0.130 |
| hsa-miR-95 | −0.051 | 0.229 | 0.301 | 0.565 |
| hsa-miR-96 | −0.063 | −0.129 | −0.525 | 0.195 |
| hsa-miR-99a* | 0.158 | −0.326 | −0.600 | 0.285 |
| hsa-miR-99a | −0.052 | −0.113 | −0.619 | 0.274 |
| hsa-miR-99b* | −0.088 | 0.298 | 0.204 | 1.290 |
| hsa-miR-99b | 0.043 | −0.055 | 0.131 | −0.018 |

The asterisk (*) after the name of the miRNA indicates the minor form of the miRNA derived from the passenger strand.

Example 2

Specificity of Differentially Expressed miRNA in EE Patients

A subsequent study was undertaken to determine whether the miRNA expression signature identified in Example 1 was specific to EE. The miRNA expression profile of EE patients was compared to that of healthy controls, as well as patients who presented with symptoms of EE but were ultimately diagnosed with chronic (non-eosinophilic) esophagitis.

Figure 3A:
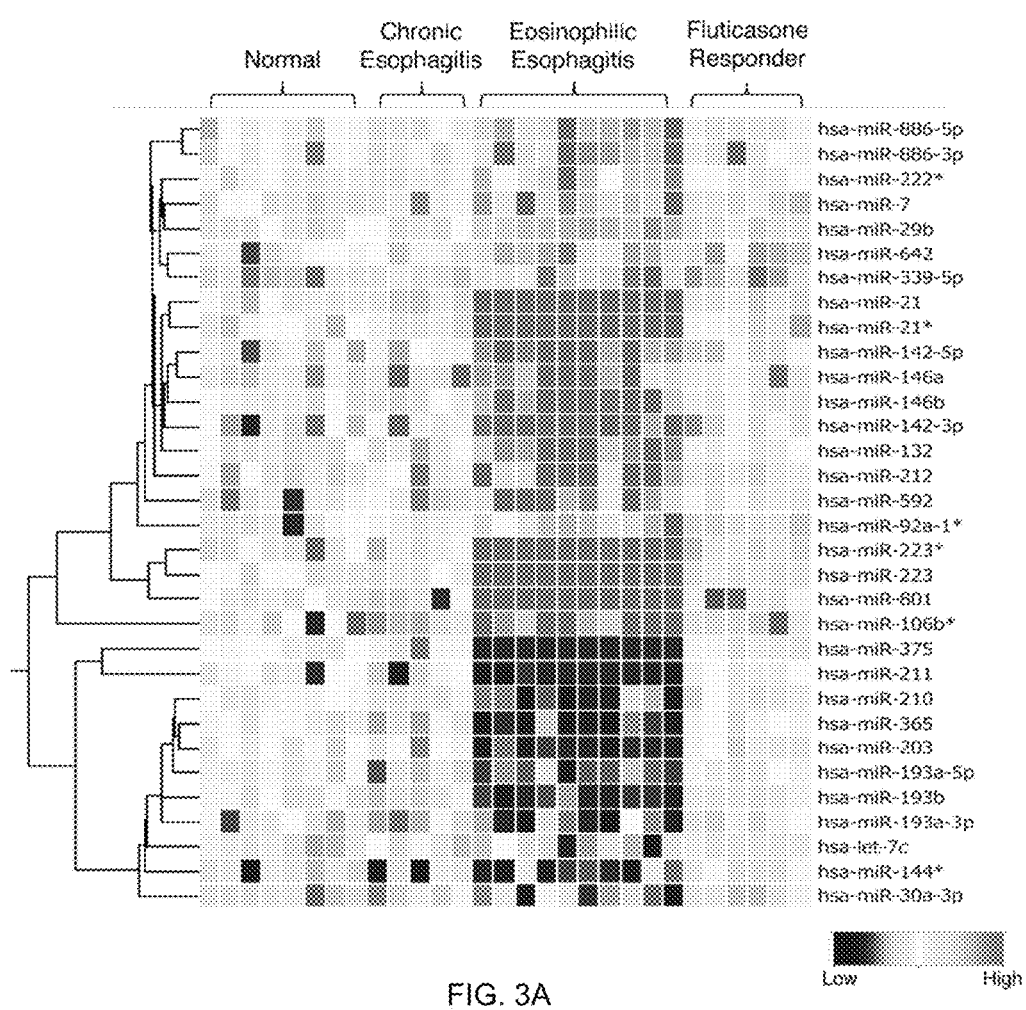
FIGS. 3A-C depict miRNA expression profiles in normal patients and EE patients compared to chronic esophagitis patients and EE patients responding to glucocorticoid therapy, as well as correlation of miR-21 and miR-223 with EE signature genes.

The chronic esophagitis patients had a miRNA expression profile that was similar to normal healthy controls and distinct from EE patients (FIG. 3A). No miRNAs that were differentially regulated between normal controls and chronic esophagitis patients were identified.

Example 3

Reversibility of Differentially Expressed miRNA in EE Patients

A subsequent study was undertaken to determine whether the EE miRNA expression signature was fixed or reversible in patients who responded to glucocorticoid treatment and had normalization of esophageal histology, including eosinophil counts. Active EE patients were compared to EE patients that responded to fluticasone propionate therapy.

Of the 32 differentially expressed miRNA, 27 were normalized. The reversible miRNAs included all of the most highly up-regulated and down-regulated miRNAs (FIG. 3A). There were 5 up-regulated miRNAs that were still dysregulated in glucocorticoid responder patients, including miR-7, miR-29b, miR-642, miR-339-5p, and miR-92a-1*.

Example 4

Correlation of miRNA Expression Levels with Esophageal Eosinophil Counts

A subsequent study was undertaken to determine whether the magnitude of miRNA expression changes correlated to the eosinophil counts in the biopsies of EE patients. Out of the 32 miRNAs that were differentially regulated in EE patients, 24 significantly correlated with esophageal eosinophil counts (Table 3). The most up-regulated miRNAs, namely miR-21 and miR-223, also had the strongest correlation of their expression level to the eosinophil counts.

TABLE 3

Correlation between miRNA expression level and peak eosinophil counts in EE patient biopsies.

| | P value | Significance | P < .05? | R square |
|---|---|---|---|---|
| hsa-miR-21 | 0.0002 | +++ | Yes | 0.663 |
| hsa-miR-223 | 0.0002 | +++ | Yes | 0.657 |
| hsa-miR-132 | 0.0003 | +++ | Yes | 0.642 |
| hsa-miR-223* | 0.0005 | +++ | Yes | 0.617 |
| hsa-miR-146b | 0.0005 | +++ | Yes | 0.615 |
| hsa-miR-801 | 0.0005 | +++ | Yes | 0.617 |
| hsa-miR-29b | 0.0005 | +++ | Yes | 0.614 |
| hsa-miR-21* | 0.0006 | +++ | Yes | 0.606 |
| hsa-miR-375 | 0.0015 | ++ | Yes | 0.552 |
| hsa-miR-212 | 0.0015 | ++ | Yes | 0.551 |
| hsa-miR-203 | 0.0019 | ++ | Yes | 0.538 |
| hsa-miR-142-5p | 0.0052 | ++ | Yes | 0.463 |
| hsa-miR-211 | 0.0060 | ++ | Yes | 0.452 |
| hsa-let-7c | 0.0065 | ++ | Yes | 0.447 |
| hsa-miR-642 | 0.0085 | ++ | Yes | 0.425 |
| hsa-miR-210 | 0.012 | + | Yes | 0.396 |
| hsa-miR-222* | 0.012 | + | Yes | 0.393 |
| hsa-miR-365 | 0.013 | + | Yes | 0.390 |
| hsa-miR-142-3p | 0.021 | + | Yes | 0.348 |
| hsa-miR-886-3p | 0.021 | + | Yes | 0.346 |
| hsa-miR-193b | 0.022 | + | Yes | 0.343 |
| hsa-miR-92a-1* | 0.023 | + | Yes | 0.339 |
| hsa-miR-339-5p | 0.034 | + | Yes | 0.302 |
| hsa-miR-886-5p | 0.035 | + | Yes | 0.298 |
| hsa-miR-146a | 0.051 | ns | No | 0.261 |
| hsa-miR-592 | 0.060 | ns | No | 0.246 |
| hsa-miR-106b* | 0.066 | ns | No | 0.236 |
| hsa-miR-193a-5p | 0.068 | ns | No | 0.234 |
| hsa-miR-193a-3p | 0.150 | ns | No | 0.152 |
| hsa-miR-7 | 0.240 | ns | No | 0.104 |
| hsa-miR-30a-3p | 0.810 | ns | No | 0.005 |
| hsa-miR-144* | 0.999 | ns | No | 0.000 |

+++: $P < 0.001$;
++: $P < 0.01$;
+: $P < 0.05$;
ns: not significant, $P > 0.05$.
The asterisk (*) after the name of the miRNA indicates the minor form of the miRNA derived from the passenger strand.

Example 5

Correlation of MiR-21 and MiR-223 Expression Levels with Major EE Signature Genes A subsequent study was undertaken to determine whether the expression of miR-21 and miR-223 could be correlated to previously identified EE signature genes.

qRT-PCR

Esophageal mRNA from EE patients was reverse-transcribed to cDNA by using the High Capacity cDNA Reverse Transcription Kit (Applied Biosystems) following the manufacturer's protocol, using the TaqManreagents for amplification of EE signature genes (Applied Biosystems) (Abonia, J. et al. *J. Allergy Clin. Immunol.* 126:140-9 (2010); Blanchard, C. et al. *J. Clin. Invest.* 116:536-47 (2006); Blanchard, C. et al. *J. Allergy Clin. Immunol.* 120:1292-300 (2007)). The EE signature genes are listed in Table 4.

TABLE 4

List of EE signature genes used for correlation analysis.

| Entrez Gene ID | Gene Name | Description |
|---|---|---|
| 55 | ACPP | Acid phosphatase, prostate |
| 72 | ACTG2 | Actin, gamma 2, smooth muscle, enteric |
| 246 | ALOX15 | Arachidonate 15-lipoxygenase |
| 383 | ARG1 | Arginase, liver |
| 10344 | CCL26 | Chemokine (C-C motif) ligand 26 |
| 1232 | CCR3 | Chemokine (C-C motif) receptor 3 |
| 131450 | CD200R1 | CD200 receptor 1 |
| 978 | CDA | Cytidine deaminase |
| 60437 | CDH26 | Cadherin-like 26 |
| 3426 | CFI | Complement factor I |
| 10370 | CITED2 | Cbp/p300-interacting transactivator, with Glu/Asp-rich carboxy-terminal domain, 2 |
| 1178 | CLC | Charcot-Leyden crystal protein |
| 9071 | CLDN10 | Claudin 10 |
| 1215 | CMA1 | Chymase 1, mast cell |
| 1296 | COL8A2 | Collagen, type VIII, alpha 2 |
| 1359 | CPA3 | Carboxypeptidase A3 (mast cell) |
| 10321 | CRISP3 | Cysteine-rich secretory protein 3 |
| 8727 | CTNNAL1 | Catenin (cadherin-associated protein), alpha-like 1 |
| 1828 | DSG1 | Desmoglein 1 |
| 2009 | EML1 | Echinoderm microtubule associated protein like 1 |
| 2312 | FLG | Filaggrin |
| 9245 | GCNT3 | Glucosaminyl (N-acetyl) transferase 3, mucin type |
| 134266 | GRPEL2 | GrpE-like 2, mitochondrial (*E. coli*) |
| 27306 | HPGDS | Hematopoietic prostaglandin D synthase |
| 3269 | HRH1 | Histamine receptor H1 |
| 3512 | IGJ | Immunoglobulin J polypeptide, linker protein for immunoglobulin alpha and mu polypeptides |
| 3596 | IL13 | Interleukin 13 |
| 3565 | IL4 | Interleukin 4 |
| 3567 | IL5 | Interleukin 5 (colony-stimulating factor, eosinophil) |
| 3568 | IL5RA | Interleukin 5 receptor, alpha |
| 3576 | IL8 | Interleukin 8 |
| 3759 | KCNJ2 | Potassium inwardly-rectifying channel, subfamily J, member 2 |
| 25984 | KRT23 | Keratin 23 (histone deacetylase inducible) |
| 4321 | MMP12 | Matrix metallopeptidase 12 (macrophage elastase) |
| 4585 | MUC4 | Mucin 4, cell surface associated |
| 4747 | NEFL | Neurofilament, light polypeptide 68 kDa |

TABLE 4-continued

List of EE signature genes used for correlation analysis.

| Entrez Gene ID | Gene Name | Description |
|---|---|---|
| 5367 | PMCH | Pro-melanin-concentrating hormone |
| 10631 | POSTN | Periostin, osteoblast specific factor |
| 64092 | SAMSN1 | SAM domain, SH3 domain and nuclear localization signals 1 |
| 9120 | SLC16A6 | Solute carrier family 16, member 6 (monocarboxylic acid transporter 7) |
| 5172 | SLC26A4 | Solute carrier family 26, member 4 |
| 84651 | SPINK7 | Serine peptidase inhibitor, Kazal type 7 (putative) |
| 7130 | TNFAIP6 | Tumor necrosis factor, alpha-induced protein 6 |
| 7177 | TPSAB1 | Tryptase alpha/beta 1 |
| 85480 | TSLP | Thymic stromal lymphopoietin |
| 23554 | TSPAN12 | Tetraspanin 12 |
| 11045 | UPK1A | Uroplakin 1A |
| 7348 | UPK1B | Uroplakin 1B |

Real-time PCR amplification was performed on a Taqman 79001HT Real-Time PCR System (Applied Biosystems). The amplification protocol consisted of a hot start of 95° C. for 10 min, followed by 40 cycles of 15 seconds at 95° C. and 1 minute at 60° C. The expression correlation study between miR-21, miR-223, and 48 EE genes was performed on GraphPad Prism (GraphPad Software, La Jolla, Calif.) software.

Negative log of p values from Pearson correlation analysis were plotted to demonstrate correlation significance with EE genes. To control for the increased risk of false positives due to the number of statistical tests performed, a Bonferroni correction was applied based on the number of gene expression profiles compared. Because the average pairwise correlation between gene expression profiles was 0.54, a principal components analysis was applied to determine the effective number of independent comparisons (Cheverud, J. *Heredity* 87:52-8 (2001)). Using this approach, a p-value of 0.002 was required to achieve a family-wise error rate of 0.05.

Results

Figure 3B:
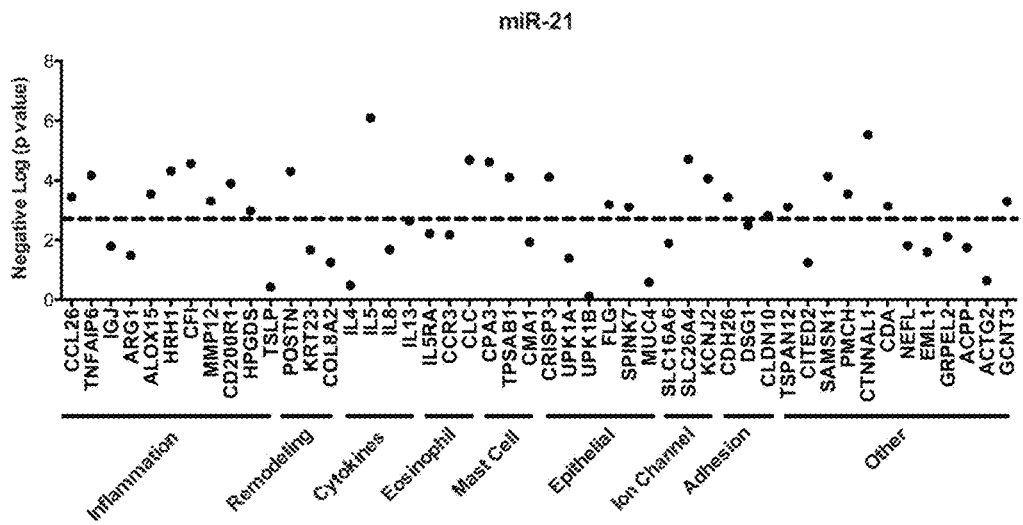
Figure 3C:
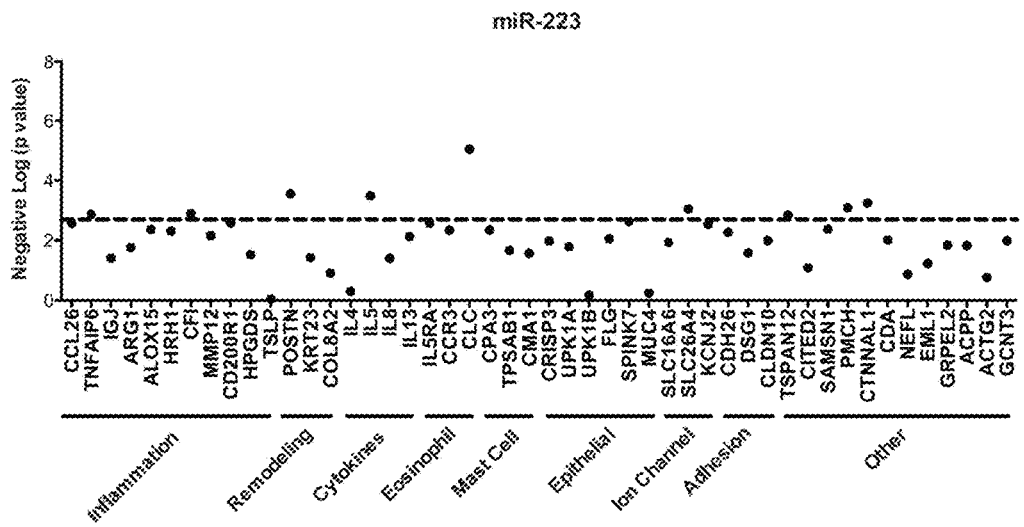

MiR-21 was found to be significantly correlated with the esophageal expression of genes involved in inflammation, including CCL26 (eotaxin-3), remodeling including POSTN (periostin), eosinophilia including IL-5, and cell specific markers for eosinophils (CLC) and mast cells (CPA3 and TPSAB1) (FIG. 3B). In addition, miR-21 significantly correlated with the gene CTNNAL1, which has been implicated in cell growth, proliferation, and wound repair (FIG. 3B) (Xiang, Y. et al. *J. Cell. Biochem.* 103:920-30 (2008)). MiR-223 had the highest correlation with POSTN, IL-5, and CLC (FIG. 3C).

Example 6

MiR-675 is Found to be a Disease Remission-Induced miRNA in EE

Figure 4A:
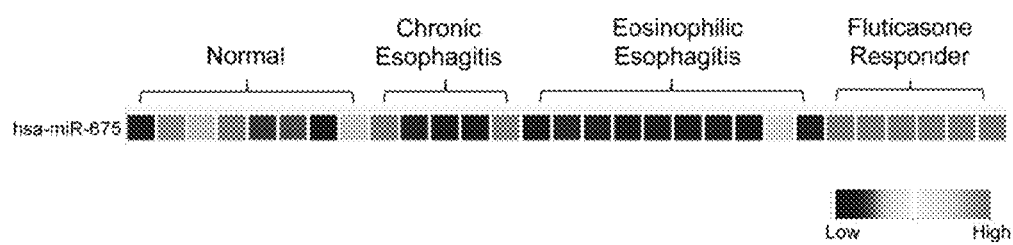
FIGS. 4A-B depict the miRNAs that are differentially regulated in EE patients in remission.

A subsequent study was undertaken to determine whether any miRNAs were differentially regulated in response to treatment. One miRNA, miR-675, was up-regulated in glucocorticoid responder patients compared to normal, EE, or chronic esophagitis patients (FIG. 4A).

Figure 4B:
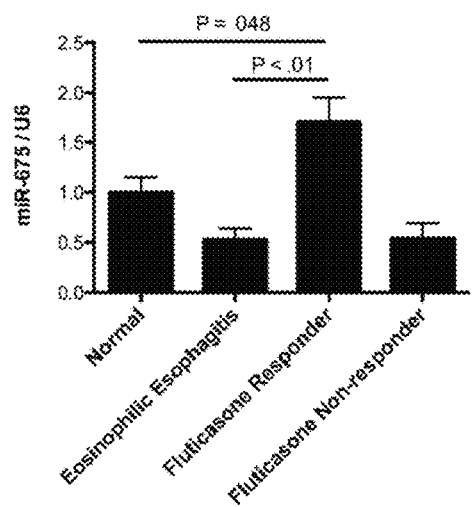

To determine whether miR-675 is a glucocorticoid-induced or EE remission-induced miRNA, miR-675 expression levels were measured in normal controls, EE patients, EE patients that responded to glucocorticoid treatment, and EE patients that did not respond to glucocorticoid treatment, as described in Example 1. The study found that miR-675 was induced in patients that responded to glucocorticoid treatment. MiR-675 was not induced in patients that did not respond to glucocorticoid treatment (FIG. 4B).

Example 7

MiR-21 and MiR-223 Co-Regulated Genes are Significantly Enriched in Pathways Involved in Adaptive Immunity and Regulation of Eosinophils Because miR-21 and miR-223 were found to be the top two upregulated miRNAs in patients with EE, a subsequent study was undertaken to identify mRNA expression patterns that significantly correlated with the expression of miR-21 and miR-223. The study was conducted on esophageal RNA samples subjected to RNA-Seq analysis, as well as previously published mRNA gene expression microarray experiments (see, e.g., Blanchard, C. et al. *J. Clin. Invest.* 116: 536-47 (2006); Abonia, J. et al. *J. Allergy Clin. Immunol.* 126:140-9 (2010)).

Analysis of miR-21 and miR-223 Co-Regulated Genes by RNA-Seq and Gene Expression Microarray RNA-Seq data were obtained from esophageal RNA samples from 11 EE patients by the Genomic Sequencing Core Laboratory at Cincinnati Children's Hospital Medical Center. The RNA-Seq was aligned to the GrCh37 build of the human genome using the Ensembl annotations as a guide for TopHat (Johns Hopkins University, Baltimore, Md.; University of California, Berkeley, Calif.; Harvard University, Cambridge, Mass.) (Trapnell, C. et al. *Bioinformatics* 25:1105-11 (2009)). The resulting files were then analyzed with Cufflinks ((Johns Hopkins University, Baltimore, Md.; University of California, Berkeley, Calif.; California Institute of Technology) to test for differential expression and differential regulation (Trapnell, C. et al. *Nat. Biotechnol.* 28:511-1 (2010)).

Figure 5A:
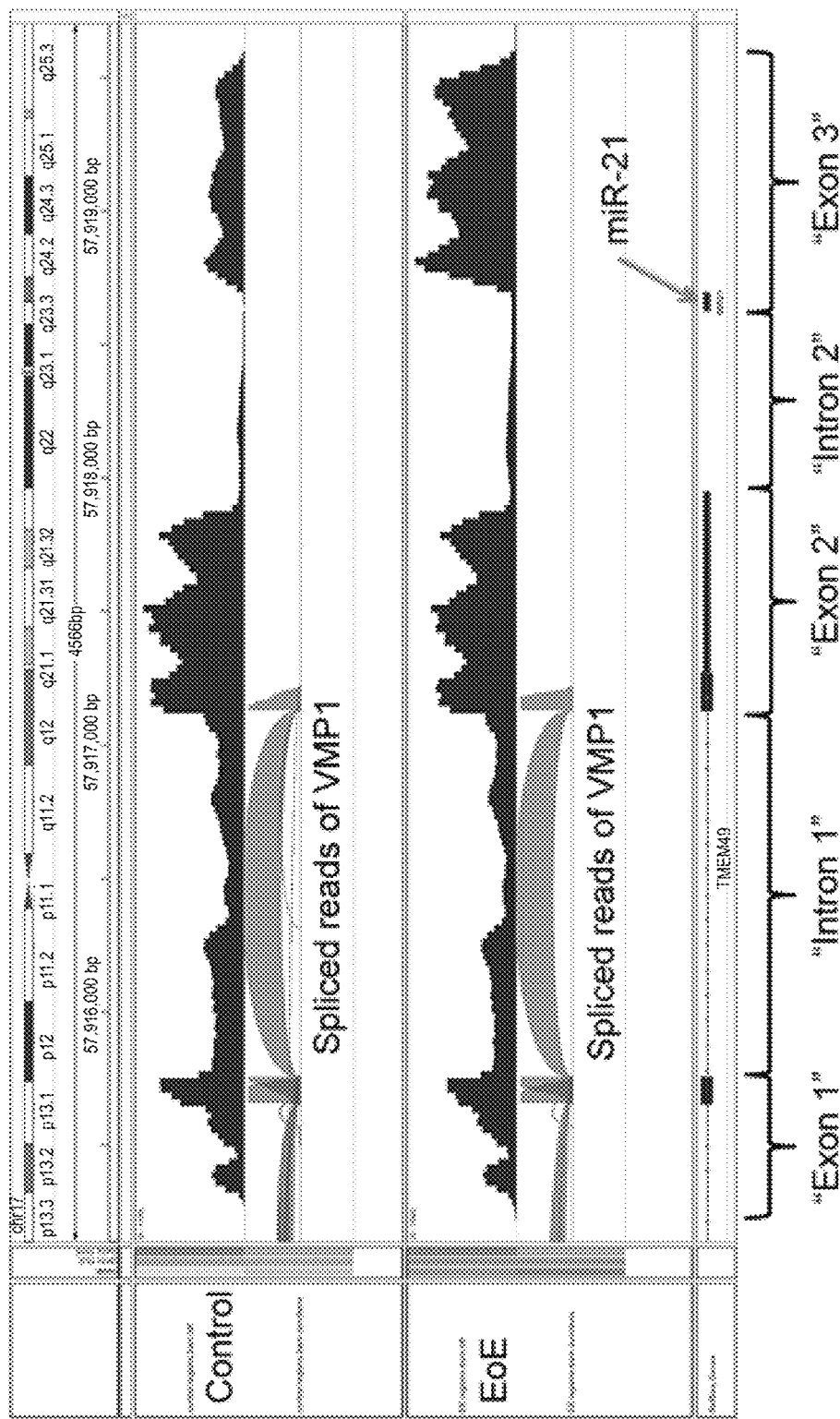
FIGS. 5A-B depict regions identified as primary transcripts for miR-21 and miR-223 (pri-miR-21 and pri-miR-223) during RNA sequencing (RNA-Seq) analysis.
Figure 5B:
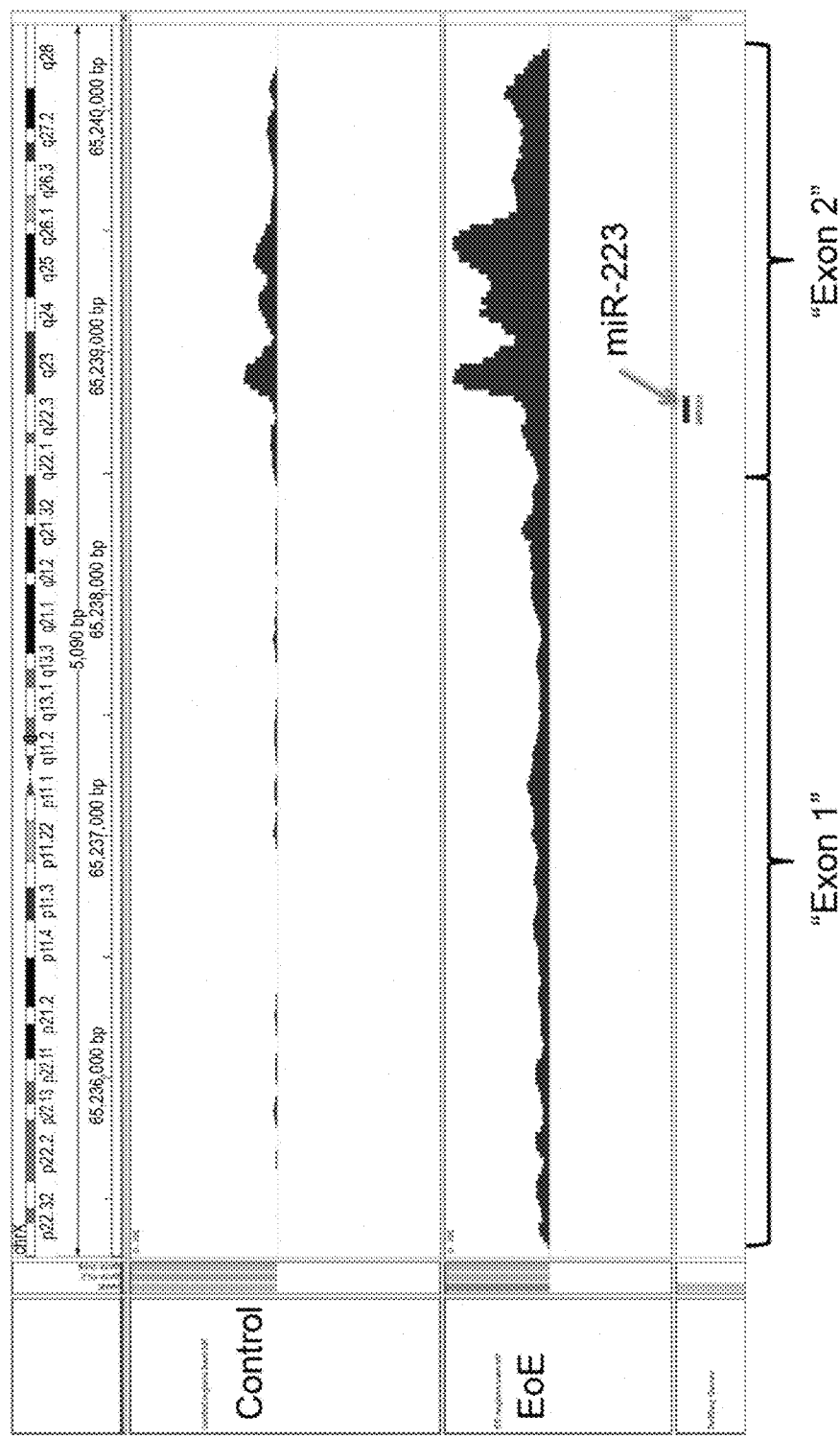

The 3' region of miR-21 was identified as the best representation of pri-miR-21 (labeled as exon 3 in FIG. 5A). The region 3' of miR-223 was identified as the best representation of pri-miR-223 (labeled as exon 2 in FIG. 5B) (Saini, H. et al. *BMC Genomics* 9:564 (2008)).

The pri-miR-21 region was found to be significantly enriched in the EE patients compared to the control patients. The expression pattern of the pri-miR-21 was then correlated with the other gene expression patterns present from the RNA-Seq expression profiles. MiR-223 was analyzed in a similar fashion. Gene expression microarray experiments from EE patients were also analyzed (Abonia, J. et al. *J. Allergy Clin. Immunol.* 126:140-9 (2010); Blanchard, C. et al. *J. Clin. Invest.* 116:536-47 (2006)).

MiR-21 and miR-223 were correlated using the Human U133 probes (Affymetrix, Santa Clara, Calif.) that best corresponded to the miRNA. A correlated gene is one whose expression follows similar or inverse trends with the miRNA in question. These probes were then correlated with microarray expression data, and 470 probes correlated well with at least one of the miRNA probes. The genes that showed the highest correlations and the most highly differentially regulated genes in the previously published EE transcriptome were used as a training set alongside genes related to $T_H1/T_H2$ differentiation and eosinophilia that are target genes of miR-21 and miR-223 (Chen, J. et al. *Nucleic Acids Res.* 37:W305-11 (2009)). The genes that showed patterns related to miR-21 or miR-223 were then analyzed to determine significant pathways and annotations related to $T_H1/T_H2$ differentiation and eosinophil development and function. The genes were then clustered based on the strength of the annotations associated with them. The results were rendered as a Cytoscape (open source software) map (FIGS. 6A-B).

Results

Figure 6A:
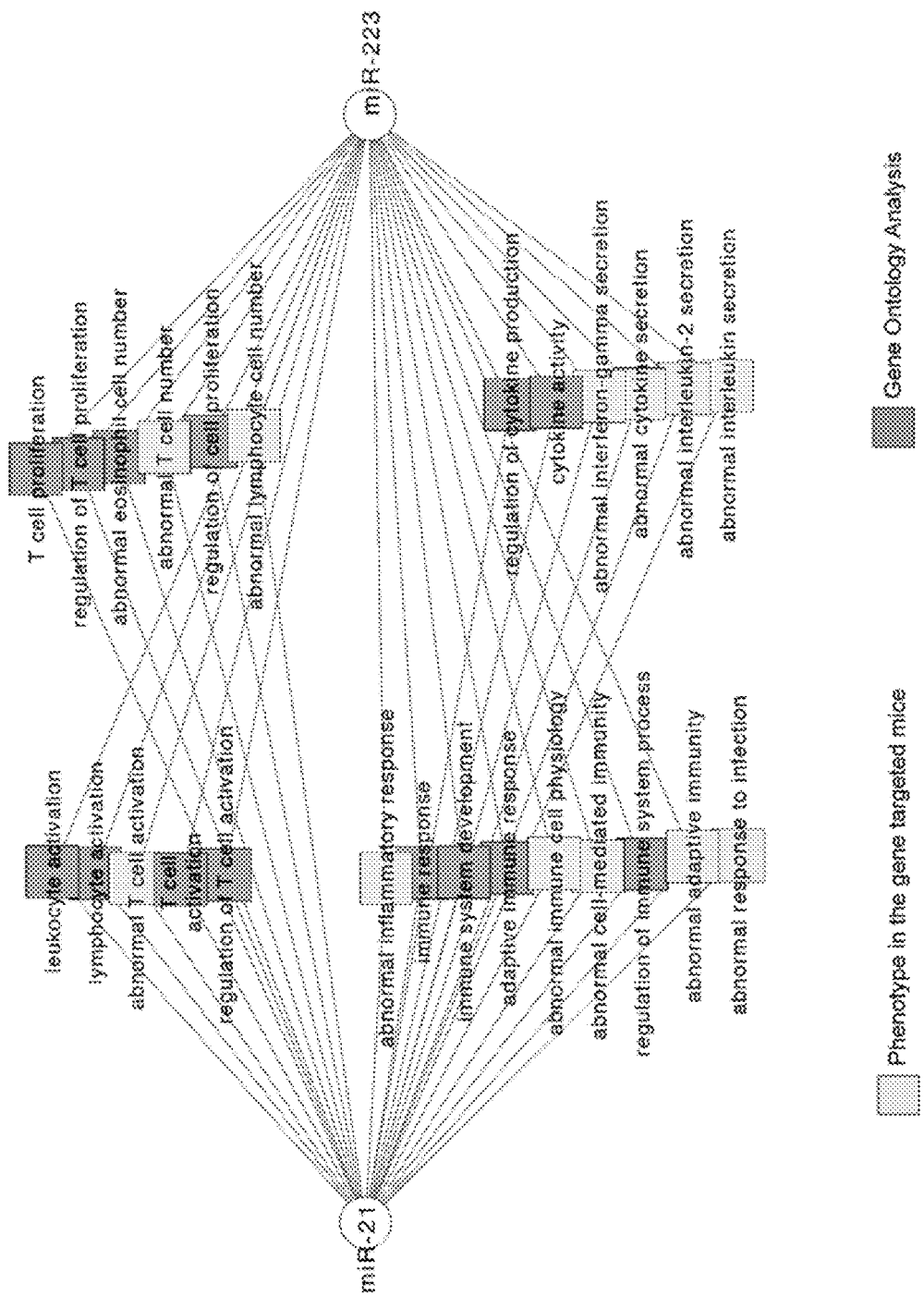
FIGS. 6A-C depict gene enrichment analyses of miR-21 and miR-223 co-regulated genes in EE patients, with extensive enrichment of genes with functional features associated with T cell polarization, IFNγ signaling, and regulation of eosinophilia among genes whose expression is correlated with miR-21 and miR-223 expression in the esophageal biopsies. The networks are shown as Cytoscape (open source software, see http <colon slash slash> www <dot> cytoscape <dot> org) graph networks generated from TopppCluster (Cincinnati Children's Hospital Medical Center, Cincinnati, Ohio) network analysis.
Figure 6B:
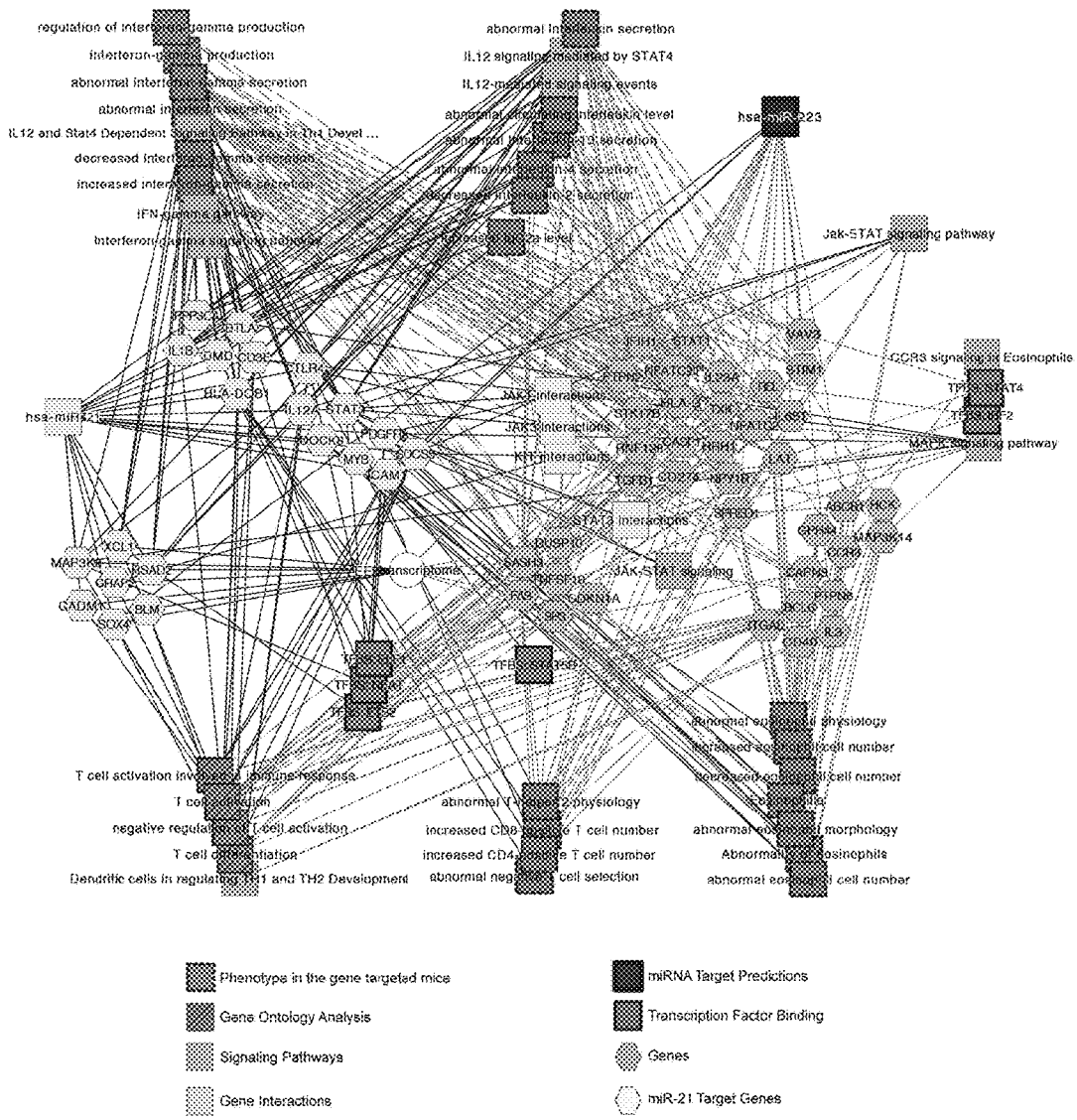
Figure 6C:
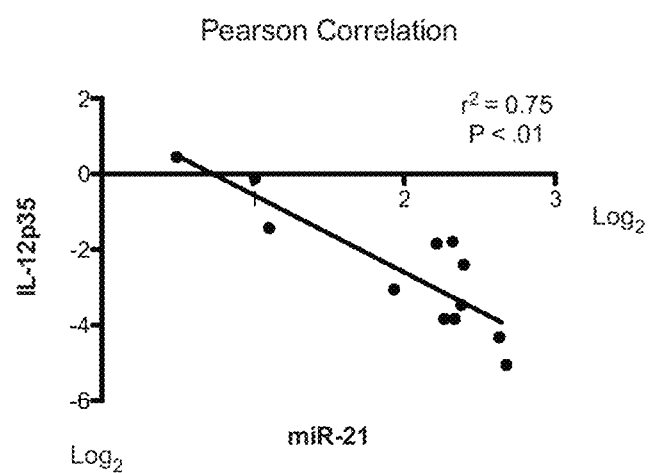
Figure 7:
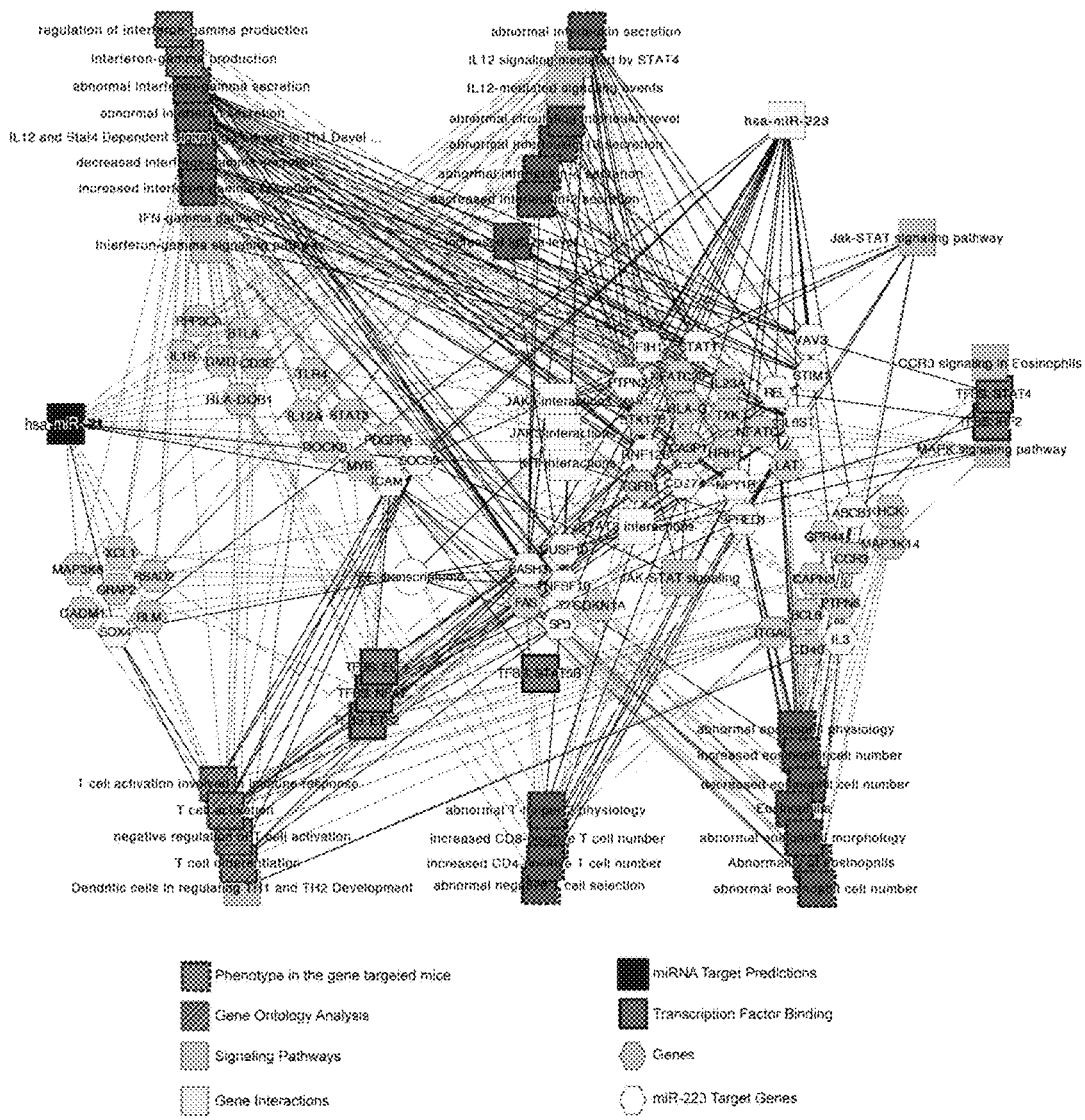
FIG. 7 depicts gene enrichment analysis of miR-21 and miR-223 co-regulated genes in EE patients. The miR-223 targets that are significantly correlated with miR-223 expression or in the EE transcriptome are highlighted as hexagons.

MiR-21 and miR-223 were found to interactively regulate many similar pathways, including leukocyte proliferation, leukocyte activation, cytokine production, and immune response (FIG. 6A). The co-regulated target genes of miR-21 and miR-223 were involved in adaptive immune system polarization, IFNγ signaling, and regulation of eosinophilia (FIG. 6B, FIG. 7). The significantly enriched pathways included regulation of interleukin secretion, interferon production and signaling, and T-cell differentiation and activation (FIG. 6B). Esophageal IL-12p35 levels showed a strong inverse correlation with esophageal miR-21 levels (FIG. 6C). This is consistent with the previous finding that miR-21 regulates $T_H1$ versus $T_H2$ balance by targeting IL-12p35 expression (Lu, T. et al. *J. Immunol.*, 182:494-5002 (2009); Lu, T. et al. *J. Immunol.*, 187:3362-73 (2011)).

Example 8

Identification of Differentially Expressed MiRNAs from EE Patient Plasma Samples MiRNAs have recently been reported to be present in plasma samples in a stable form protected from endogenous RNAse activities (Mitchell, P. et al. *Proc. Natl. Acad. Sci. U.S.A.*, 105:10513-8 (2008)). Plasma miRNAs can therefore be used as noninvasive biomarkers ((Mitchell, P. et al. *Proc. Natl. Acad. Sci. U.S.A.*, 105:10513-8 (2008); Zahm, A. et al. *J. Pediatr. Gastroenterol. Nutr.*, 53:26-33 (2011); Shen, J. et al. *Lab. Invest.*, 91:579-87 (2011)). Accordingly, a study was undertaken to evaluate a subset of the miRNAs found to be differentially regulated in the esophageal biopsies of EE patients to determine whether these miRNAs could also be differentially regulated in patient plasma samples.

Patient Selection for Plasma miRNA Analysis

For the plasma miRNA level analysis, normal atopic controls (defined as patients having asthma, allergic rhinitis, and/or eczema) were selected to control for the atopy commonly seen in EE patients. The active EE patients were selected based on a clinical diagnosis of EE and eosinophil counts of ≥24 per 400× hpf in the esophageal biopsies. Patients with systemic or swallowed topical glucocorticoid use were excluded from the selection of normal atopic control or active EE patients. The EE remission patients were selected based on a history of EE and treated with swallowed topical glucocorticoid, with response as indicated by eosinophil count ≤1 per 400× hpf and normalization of histological features of the disease.

Patients were selected retrospectively from cell-free plasma samples collected between November 2007 and June 2011 based on the selection criteria outlined and the availability of sufficient quantity of plasma samples for RNA isolation. A total of 13 normal, 13 EE, and 14 EE remission patients were included in the plasma miRNA analysis. Three normal, 4 EE, and 3 EE remission patients included in the plasma miRNA analysis overlapped with patients selected for esophageal miRNA microarray analysis. Other patients included in the esophageal miRNA microarray analysis did not have sufficient quantities of plasma samples available for RNA isolation.

RNA Isolation from Human Plasma Samples

Cell-free human plasma samples (750 μl) were mixed with Trizol LS reagent (Life Technologies, Carlsbad, Calif.) at a 1:3 ratio, with 1 μg of RNA from the bacteriophage MS2 added as carrier RNA. The bacteriophage MS2 RNA was selected as a carrier RNA because it does not contain miRNAs. The RNA was then extracted using the miRNEasy Mini Kit (Qiagen) according to the manufacturer's protocols.

Detection of Plasma miRNAs

Plasma (prepared from Na-EDTA tubes) miRNAs were reverse transcribed using MegaPlex RT primers (Applied Biosystems), Human pool set V2.1 with pre-amplification (Applied Biosystems), according to the manufacturer's protocols. The pre-amplified samples were diluted 1:40, and 1.5 μl of the diluted product was then used in a 15 μl PCR reaction using the TaqMan miRNA Assays (Applied Biosystems), following the manufacturer's protocols.

Results

Using plasma samples from EE patients and normal controls, the expression levels of the 10 most differentially regulated miRNAs associated with EE were determined. This analysis included 6 up-regulated miRNAs, namely miR-21, miR-132, miR-142-3p, miR-146a, miR-146b, and miR-223, and four down-regulated miRNAs, namely miR-203, miR-210, miR-365, and miR-375.

None of the down-regulated miRNAs was detected in the EE or normal control plasma samples after 40 cycles of PCR. Of the up-regulated miRNAs, the expression of miR-142-3p, miR-146a, miR-146b, and miR-223 was detected in all of the plasma samples. The expression of miR-21 and miR-132 were only detected in some of the samples at low levels and were not analyzed further.

Because miR-16 has been reported to have a constant expression level in plasma samples (Shen, J. et al. *Lab. Invest.* 91:579-87 (2011)), miR-16 was used as an endogenous control to determine the differential expression of the miRNAs between EE patient plasma samples and normal controls. There were no significant differences in the average $C_T$ value of miR-16 between normal and EE patients (25.5±0.4 vs, 26.0±1.1, respectively).

Figure 8A:
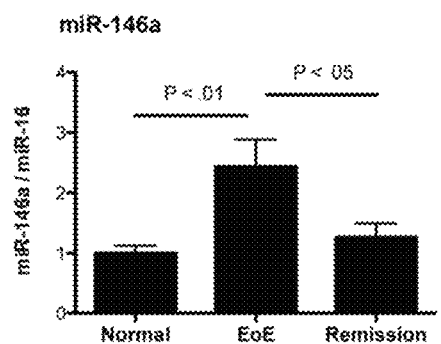
FIGS. 8A-C depict miRNAs differentially expressed in the plasma of active EE patients and EE remission patients compared to normal controls. The graphs in FIGS. 8A-C depict the expression of 3 miRNAs, namely (FIG. 8A) miR-146a, (FIG. 8B) miR-146b, and (FIG. 8C) miR-223, which were determined in plasma samples from active EE patients and EE remission patients and were compared to normal controls. The relative expression levels were normalized to miR-16. N=13-14 plasma samples per group; data are represented as mean±SEM; NS: not significant with P >0.05.
Figure 8B:
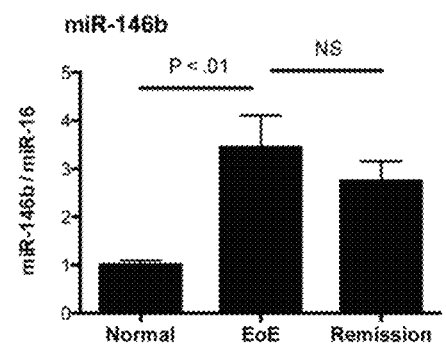
Figure 8C:
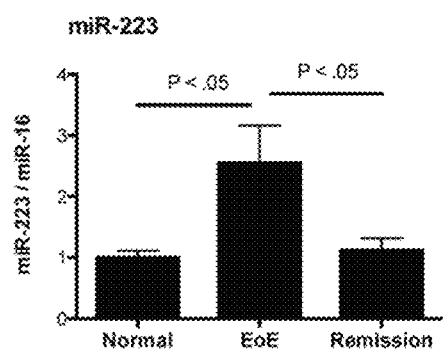
Figure 9:
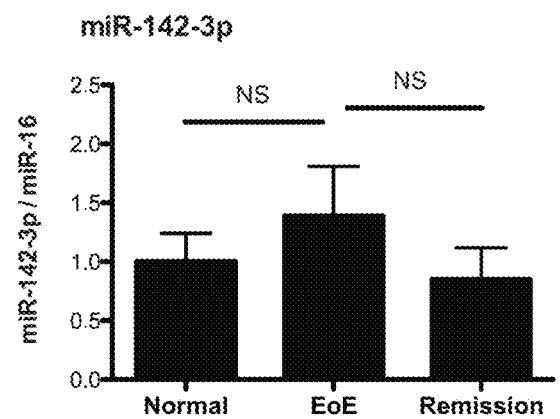
FIG. 9 depicts miR-142-3p expression levels in patient plasma samples. Expression of miR-142-3p was determined in plasma samples from active EE patients and EE remission patients compared to normal controls. The relative expression levels were normalized to miR-16. N=13-14 plasma samples per group; data are represented as mean±SEM; NS: not significant, with P >0.05.

Comparing EE patients to normal controls, miR-146a, miR-146b, and miR-223 were found to be up-regulated in EE patient plasma samples (FIGS. 8A-C). While miR-146a and miR-223 returned to baseline levels in EE remission patients, miR-146b remained elevated (FIGS. 8A-C). Using a 1.5-fold change cut-off, the positive predictive value and negative predicative value of normal controls vs. active EE patients and active EE patients vs. EE patients in remission were calculated (Table 5). The levels of miR-142-3p were not changed between any of the groups (FIG. 9).

TABLE 5

Positive predictive value and negative predictive value of differentially regulated serum miRNAs.

|  | Normal vs. Active EE | | Active EE vs. EE Remission | |
| --- | --- | --- | --- | --- |
|  | Positive Predictive Value | Negative Predictive Value | Positive Predictive Value | Negative Predictive Value |
| miR-146a | 0.82 | 073 | 0.60 | 0.66 |
| miR-146b | 0.91 | 0.30 | 0.50 | 0.50 |
| miR-223 | 0.77 | 0.64 | 0.63 | 0.62 |

Example 9

Elucidation of the Functional Role of MiR-21 in EE

A study was undertaken to determine the functional role for miR-21, as this was the most induced miRNA in the esophagus of EE patients. Wild type (WT) and miR-21 gene knockout (KO) mice (Lu, T. et al. *J. Immunol.* 187:3362-73 (2011)) were subjected to an experimental model of EE, elicited by repeated exposure to the allergen *Aspergillus fumigatus*, as reported (Mishra, A. et al. *J. Clin. Invest.* 107:83-90 (2001)). Saline challenge was used on WT and KO mice as a control. Following allergen exposure or saline challenge, the number of eosinophils in the esophagus was quantitated by anti-major basic protein immunohistochemistry, followed by morphometric analysis.

Figure 10:
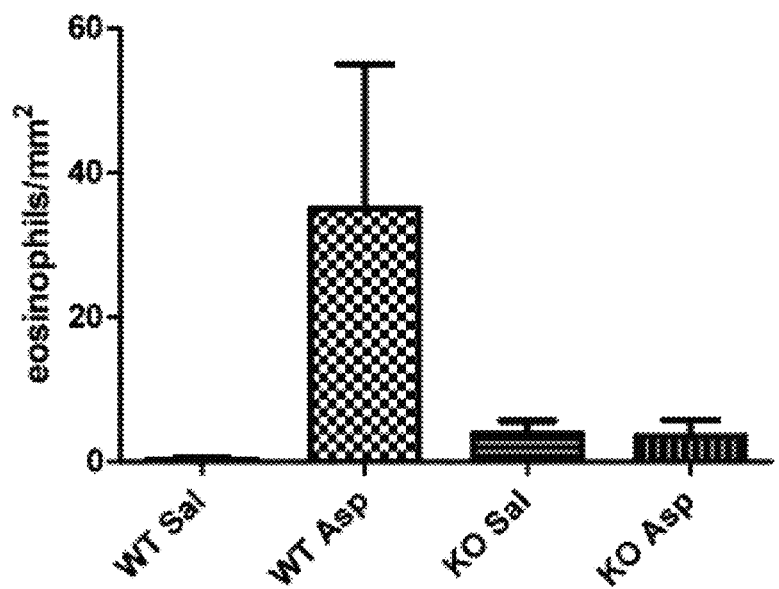
FIG. 10 depicts esophageal eosinophil counts for wild type (WT) mice and miR-21 gene knockout (KO) mice under saline control (Sal) or upon exposure to the allergen *Aspergillus fumigatus* (Asp).

As shown in FIG. 10, miR-21 KO mice were markedly protected from the development of experimental EE. These findings demonstrate a functional role for miR-21 in the elicitation of experimental EE and further support the utility of anti-miR-21 therapeutic agents, such as miR-21 antagomirs.

Example 10

Expression of MiR-21 in an Ex Vivo Culture of Bone Marrow-Derived Eosinophils

A study was conducted to determine the role of miR-21 in eosinophil development and function. A murine ex vivo bone marrow-derived eosinophil culture model that generates >90% eosinophils after 14 days of culture was utilized (Dyer, K. et al. *J. Immunol.* 181:4004-9 (2008)).

Mice

MiR-21 gene targeted mice were backcrossed for 5 generations into the C57BL/6 background, described by a previous protocol (Lu, T. et al. *J. Immunol.* 187:3362-73 (2011)). Littermate controls were used for all experiments. All animals used were housed under specific pathogen-free conditions in accordance with institutional guidelines.

Bone Marrow-Derived Cell Cultures

Bone marrow cells were collected from femurs and tibia of the mice, and the stem/progenitor cell-enriched low-density fraction was isolated by gradient centrifugation using the Histopaque 1083 (Sigma, St. Louis, Mo.), according to the manufacturer's protocol. The low density fraction of bone marrow cells were cultured in Iscove's Modified Dulbecco's Media (IMDM) with 10% fetal bovine serum (FBS), 100 U/ml penicillin, and 100 μg/ml streptomycin supplemented with 100 ng/mL stem cell factor and 100 ng/mL FLT-3 ligand (Peprotech, Rocky Hill, N.J.) from day 0 to day 4 at a concentration of $1 \times 10^6$/mL in 6-well plates.

For eosinophil differentiation, the stem cell factor and FLT-3 ligand were replaced with 10 ng/mL IL-5 on day 4, and the cells were cultured for an additional 10 days in the presence of IL-5 (Dyer, K. et al. *J. Immunol.* 181:4004-9 (2008)). One half of the culture media was replaced with fresh media every other day. The cells were counted and concentration was adjusted to $1 \times 10^6$/mL during each media change. Eosinophil maturity was assessed by fluorescence-activated cell sorting (FACS) staining for CCR3 and Siglec-F and/or Diff-Quik (Fisher Scientific) staining of cytospin preparations. For neutrophil differentiation, the stem cell factor and FLT-3 ligand were replaced with 20 ng/mL granulocyte colony-stimulating factor (G-CSF) on day 4, and the cells were cultured for an additional 6 days in the presence of G-CSF. Eosinophil and neutrophil progenitor growth was assessed by counting the cells every 2 days using a hemacytometer.

Quantitative Assessment of miRNA Levels

Levels of miRNA expression were measured quantitatively by using the TaqMan MicroRNA Assay (Applied Biosystems), following the manufacturer's protocol, and assayed on the 7900HT Real-Time PCR System (Applied Biosystems). Normalization was performed using U6 small nuclear RNA. Relative expression was calculated using the comparative $C_T$ method, as previously described (Livak, K. et al. *Method.* 25:402-8 (2001)).

Statistical Analysis

Statistical analyses were performed with the student's t-test or one-way ANOVA with Tukey post-hoc test where appropriate. Statistical significance and the p values are indicated on the figures where appropriate. P values less than 0.05 were considered statistically significant.

Results

Figure 11B:
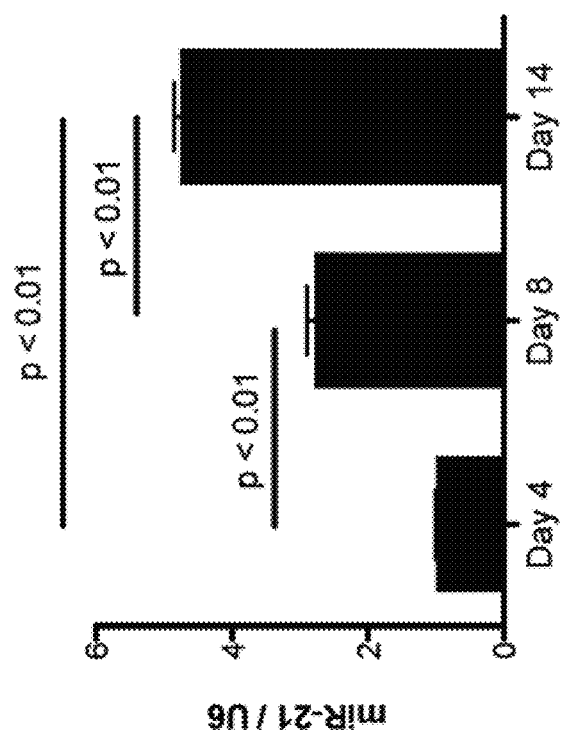
FIGS. 11A-B depict miR-21 induction during eosinophil differentiation.
Figure 11A:
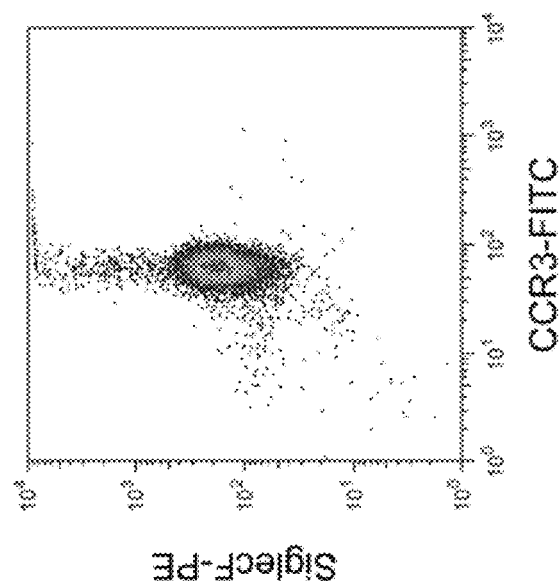

High purity ex vivo bone marrow-derived eosinophils were obtained, as determined by FACS staining for CCR3 and Siglec-F double positive cells, on day 14 (FIG. 11A). Up-regulation of miR-21 was observed during the eosinophil differentiation from day 4 to day 14 (FIG. 11B).

Example 11

Figure 12A:
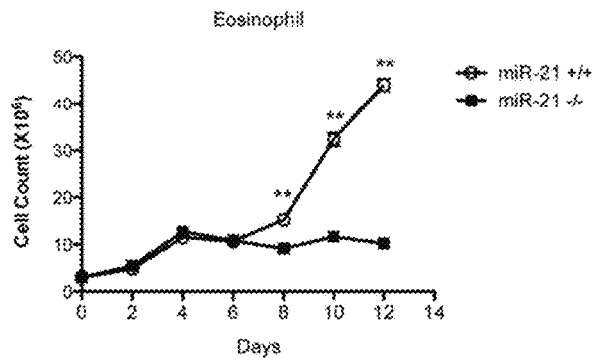
FIGS. 12A-C depict the growth of eosinophil progenitor cells from miR-21$^{-/-}$ mice and miR-21$^{+/+}$ controls during the ex vivo eosinophil culture.
Figure 12B:
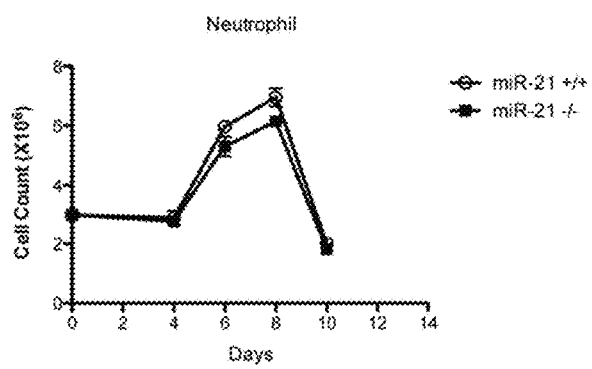
Figure 12C:
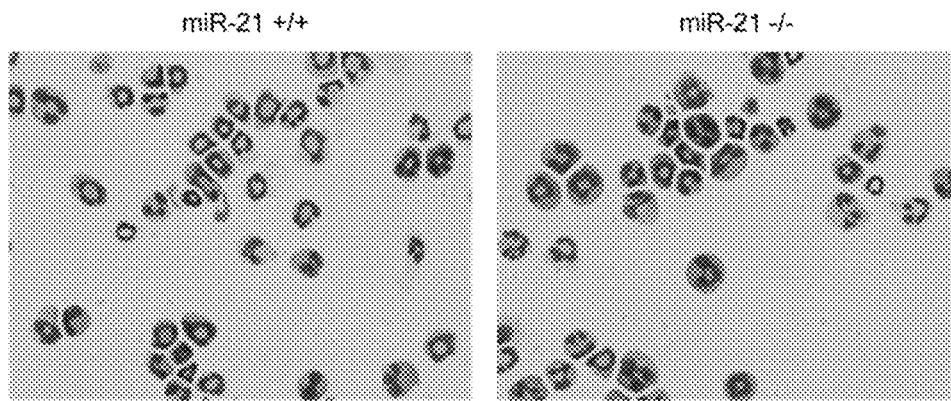

Arrested Eosinophil Progenitor Growth in Eosinophil Cultures Derived from MiR-21$^{-/-}$ Mice In a subsequent study, the effect of miR-21 on eosinophil development was determined. Progenitor cells were cultured into eosinophils, and a profound phenotype in cellular growth was noted. The miR-21$^{-/-}$ mice had a marked arrest in eosinophil progenitor growth compared to controls, with the most prominent effect seen between days 8 and 12 (FIG. 12A). By comparison, neutrophil progenitor growth was not significantly changed (FIG. 12B). The miR-21$^{+/+}$ and miR-21$^{-/-}$ bone marrow-derived eosinophils were morphologically indistinguishable from each other at day 12 (FIG. 12C).

Example 12

Increased Apoptosis in Eosinophil Cultures Derived from MiR-21$^{-/-}$ Mice

In the same study, the levels of apoptosis in the miR-21$^{-/-}$ and miR-21$^{+/+}$ eosinophil progenitor cultures were measured by Annexin V and 7AAD staining. The viable cells are Annexin V and 7AAD double negative. The early apoptotic cells are Annexin V positive and 7AAD negative. The late apoptotic cells are Annexin V and 7AAD double positive.

Figure 13:
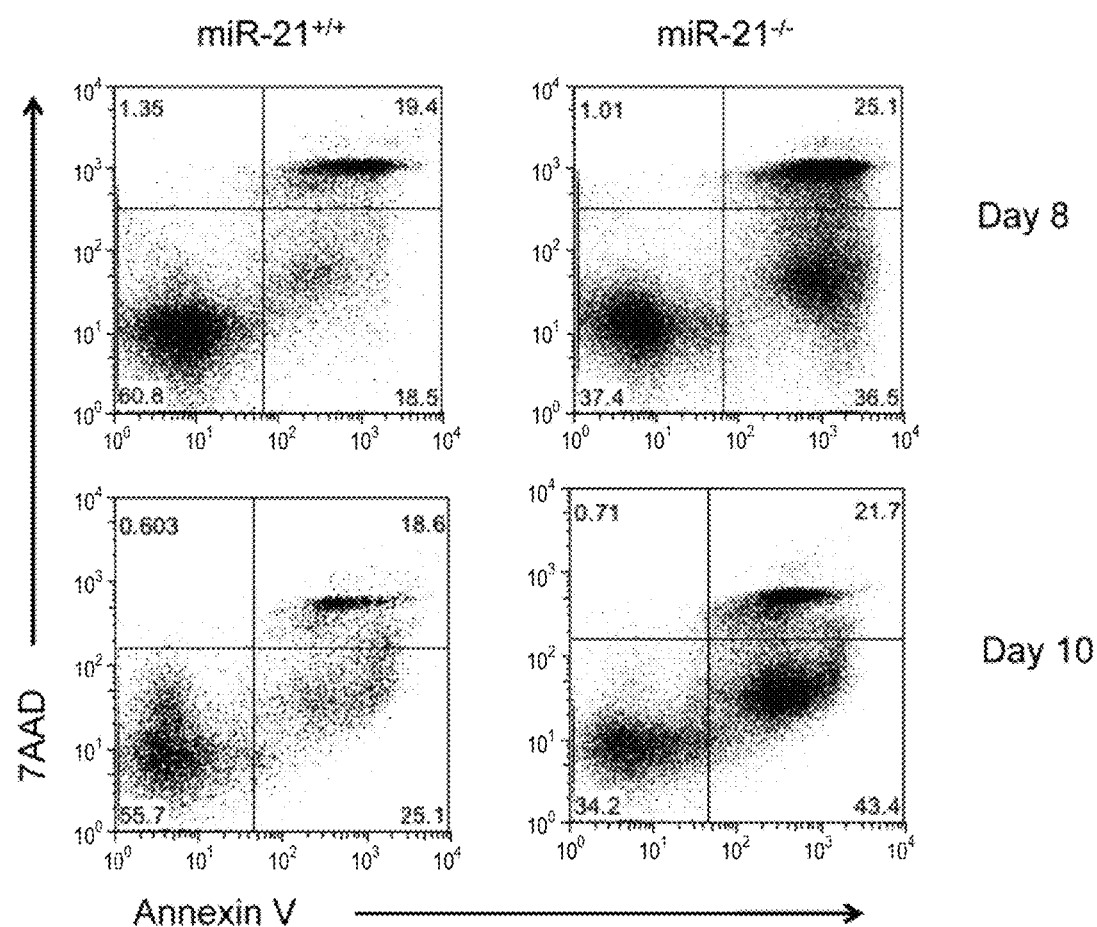
FIG. 13 depicts levels of apoptosis in the eosinophil progenitor culture from the miR-21$^{+/+}$ and miR-21$^{-/-}$ mice. Levels of annexin V and 7AAD staining during eosinophil differentiation culture were determined by fluorescence-activated cell sorting (FACS). The viable cells are annexin V$^-$/7AAD$^-$. The early apoptotic cells are annexin V$^+$/7AAD$^-$, and the late apoptotic cells are annexin V$^+$/7AAD$^+$.

Compared to miR-21$^{+/+}$ cultures, the miR-21$^{-/-}$ eosinophil progenitor cultures have increased levels of both the Annexin V$^+$ 7AAD$^-$ population and the AnnexinV$^+$ 7AAD$^+$ population, indicative of increased levels of apoptosis in the miR-21$^{-/-}$ cultures (FIG. 13).

Example 13

Reduced Eosinophilia in the Blood of MiR-21$^{-/-}$ Mice

A subsequent study was undertaken to determine the consequences of miR-21 on eosinophil hematopoiesis in vivo. This was achieved by determining the blood eosinophil level in the miR-21$^{-/-}$ mice, using FACS to measure blood eosinophil percentage.

Determination of Blood Eosinophil Percentage by FACS

Red blood cells were lysed from mouse blood by using red blood cell (RBC) lysis buffer (Sigma) twice for 5 minutes each time. The eosinophil percentage was determined by FACS staining of blood cells with fluorescein (FITC)-conjugated anti-CCR3 (R&D Systems, Minneapolis, Minn.) and PE-conjugated anti-Siglee-F (BD Biosciences, San Diego, Calif.). The eosinophils analyzed were the CCR3 and Siglee-F double positive cells, as described by a previous protocol (Fulkerson, P. et al. *Proc. Natl. Acad. Sci. U.S.A.* 103:16418-16423 (2006)).

Results

Figure 14A:
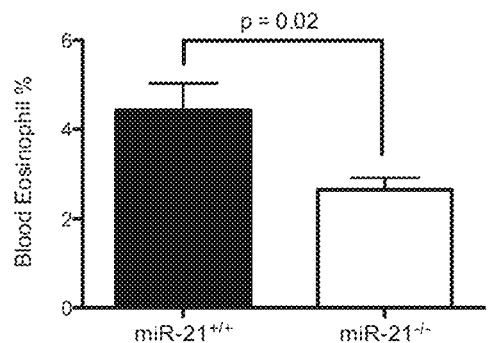
FIGS. 14A-C depict blood eosinophil percentage and bone marrow eosinophil colony forming unit capacity in the miR-21$^{+/+}$ and miR-21$^{-/-}$ mice.

The miR-21$^{-/-}$ mice were found to have a decreased blood eosinophil percentage compared to miR-21$^{+/+}$ littermate controls (FIG. 14A).

Example 14

Reduced Eosinophil Colony-Forming Unit Capacity in the Bone Marrow of MiR-21$^{-/-}$ Mice In the same study, a colony forming unit (CFU) assay was undertaken.

Colony Forming Unit (CFU) Assay

Low density bone marrow fractions were plated at a concentration of 1×10$^5$/ml in M4230 methylcellulose media (Stemcell Technologies, Vancouver, BC, Canada) supplemented with 50 ng/mL of IL-5 for the CFU-Eos assay or at a concentration of 5×10$^4$/ml in M4230 methylcellulose media supplemented with 50 ng/mL G-CSF for the CFU-G assay, according to the manufacturer's protocols. After 8 days of incubation at 37° C. and 5% CO$_2$, eosinophil colonies (CFU-Eos) and neutrophil colonies (CFU-G) were counted and reported as CFU per 10$^5$ cells. Cell morphology of CFU-Eos and CF-G was confirmed by Diff-Quik staining of cytospin preparations of the colonies.

Results

Figure 14B:
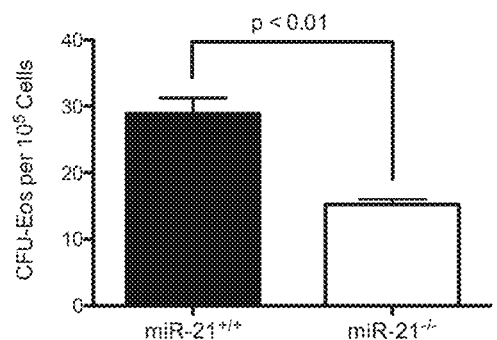
Figure 14C:
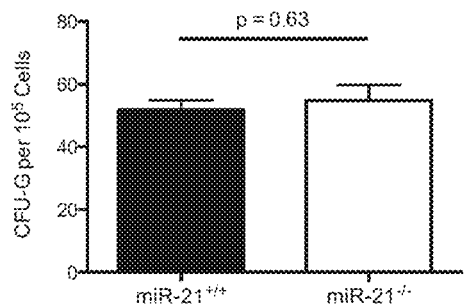

The miR-21$^{-/-}$ mice were found to have decreased eosinophil colony-forming unit capacity in the bone marrow (FIG. 14B). By comparison, the neutrophil colony-forming unit capacity was unchanged (FIG. 14C), indicating an eosinophil progenitor-specific defect.

Example 15

Whole Genome Microarray Analysis of Genes Differentially Regulated Between MiR-21$^{+/+}$ and MiR-21$^{-/-}$ Eosinophil Progenitor Cultures In a subsequent study, a whole genome microarray analysis was performed at days 4, 8, and 12 of the culture in miR-21$^{+/+}$ and miR-21$^{-/-}$ cells. The purpose of the analysis was to gain insight into the potential molecular mechanisms by which miR-21 regulates eosinophil development.

Mouse Genome-Wide mRNA Microarray

The Mouse Gene 1.0ST array (Affymetrix) was used to compare gene expression profiles between miR-21$^{+/+}$ and miR-21-/- eosinophil progenitor cultures at day 4, day 8, and day 12. Microarray data were analyzed using GeneSpring software (Agilent Technologies). Global scaling was performed to compare genes from chip to chip, and a base set of probes was generated by requiring a minimum raw expression level of the 20$^{th}$ percentile out of all probes on the microarray. The resulting probe sets were then baseline transformed and filtered on at least a 1.5-fold difference between miR-21$^{+/+}$ and miR-21$^{-/-}$ eosinophil progenitor cultures.

Figure 15A:
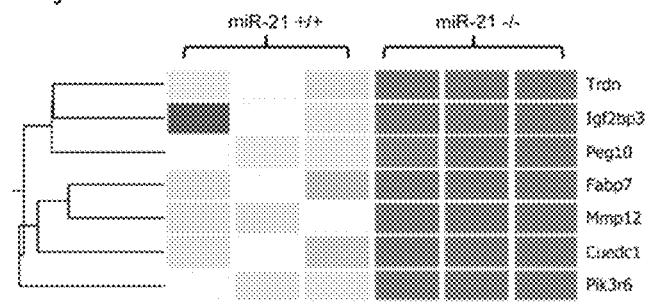
FIGS. 15A-D present heatmaps of differentially regulated genes between miR-21$^{+/+}$ and miR-21$^{-/-}$ eosinophil progenitor cultures at day 8 and day 12.
Figure 15B:
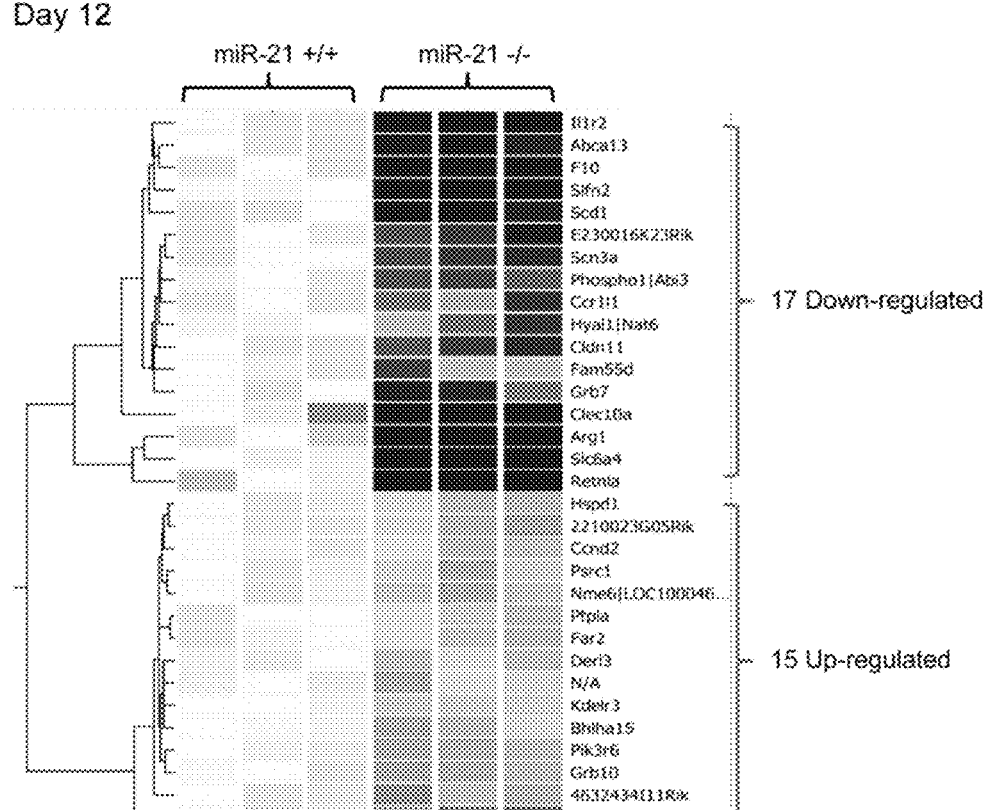

Statistical significance was determined at p<0.05 with Benjamini Hochberg false discovery rate correction. The resulting list of genes was clustered using hierarchical clustering, and a heatmap was generated (FIGS. 15A-B). Biological functional enrichment analysis was carried out using ToppGene/ToppCluster (Cincinnati Children's Hospital Medical Center) (Chen, J. et al. *Nucleic Acids Res.* 37:W305-11 (2009); Kaimal, V. et al. *Nucleic Acids Res.* 38:W96-102 (2010)). The microarray data have been deposited into the Array Express database, found at http <colon slash slash> www <dot> ebi <dot> ac <dot> uk <slash> arrayexpress, with accession number E-MEXP-3346, in compliance with MIAME standards.

Quantitative RT-PCR

Total RNA was reverse transcribed using the High Capacity cDNA Reverse Transcription kit (Applied Biosystems), according to the manufacturer's protocol. All primer/probe sets were obtained from Applied Biosytems. Samples were analyzed by TaqMan qRT-PCR for PIK3R6 (Assay 10: Mm01335671_m1), MS4A3 (Assay ID: Mm_00460072_m1), PSRC1 (Assay ID: Mm_00498358_m1), and GRB7 (Assay ID: Mm_01306734_m1) and normalized to HPRT1 (Assay 10: Mm00446968_m1). Relative expression was calculated using the comparative $C_T$ method (Livak, K. and Schmittgen, T. *Methods,* 25:402-408 (2001)).

Results

No differentially regulated genes were observed at day 4, which is consistent with the miR-21 expression data and corresponds to the lack of any observed phenotype at day 4 of the culture. The growth of stem/progenitor cells under the influence of SCF and Flt-3L therefore is not dependent on miR-21. At day 8 of the eosinophil progenitor culture, 7 genes were up-regulated in the miR-21$^{-/-}$ eosinophil progenitor culture compared to the miR-21$^{+/+}$ culture, and there were no down-regulated genes (FIG. 15A; Table 6). At day 12 of the eosinophil progenitor culture, there were 17 down-regulated and 15 up-regulated genes (FIG. 15B; Table 7).

The up-regulated genes include Ms4a3 and Bhlha15, each of which is known to have a role in inhibiting cell growth (see, e.g., Donato, J. et al. *J. Clin. Invest.* 109:51-58 (2002); Jia, D. et al. *Gastroenterology* 135:1687-97 (2008)). The down-regulated genes include Grb7 and Hyal1, each of which has been shown to promote cell growth (see, e.g., Wang, Y. et al. *Clin. Cancer Res.* 16:2529-39 (2010); Tan, J. et al. *Int. J. Cancer* 128:1303-15 (2011)).

Figure 15C:
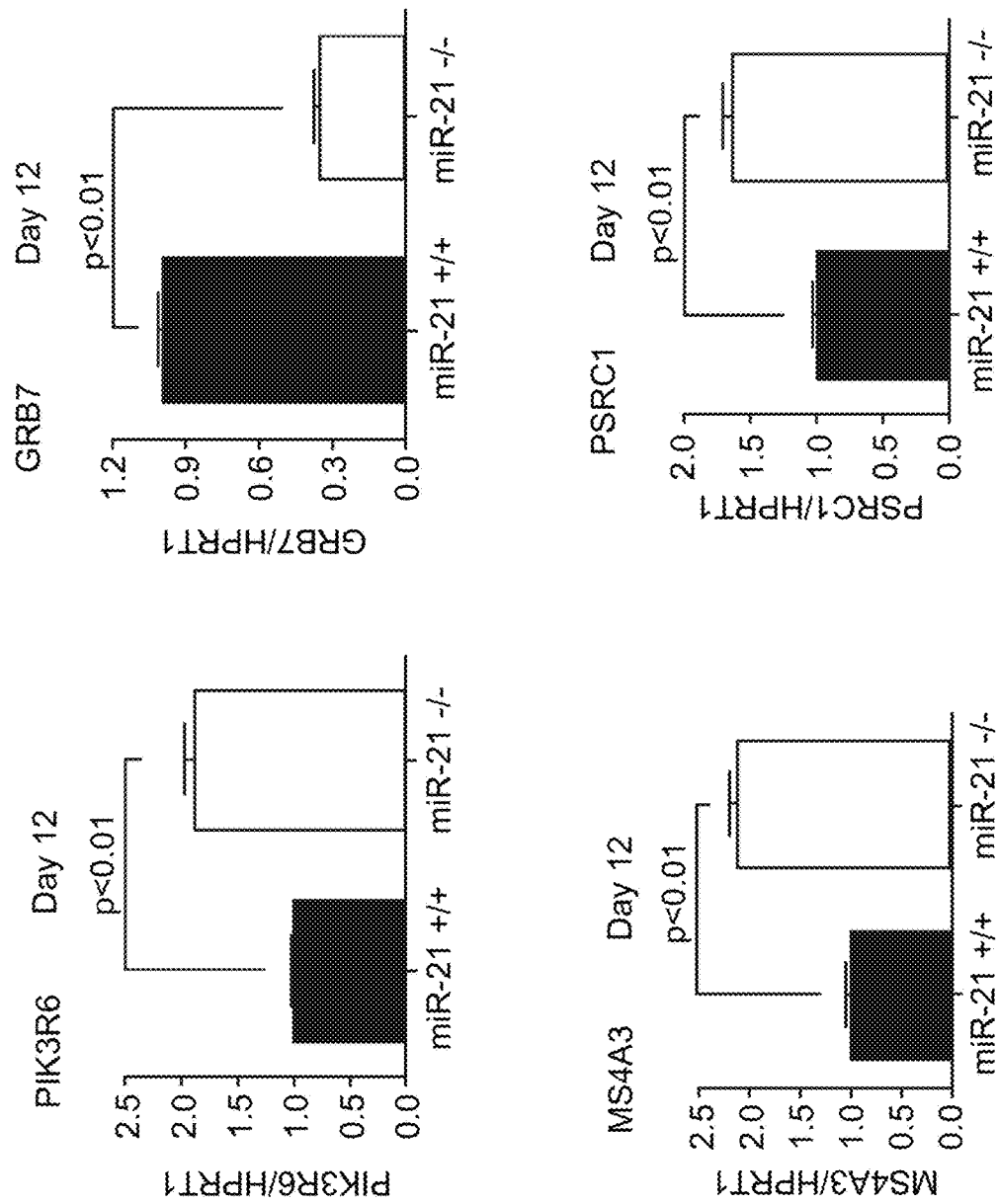
Figure 15D:
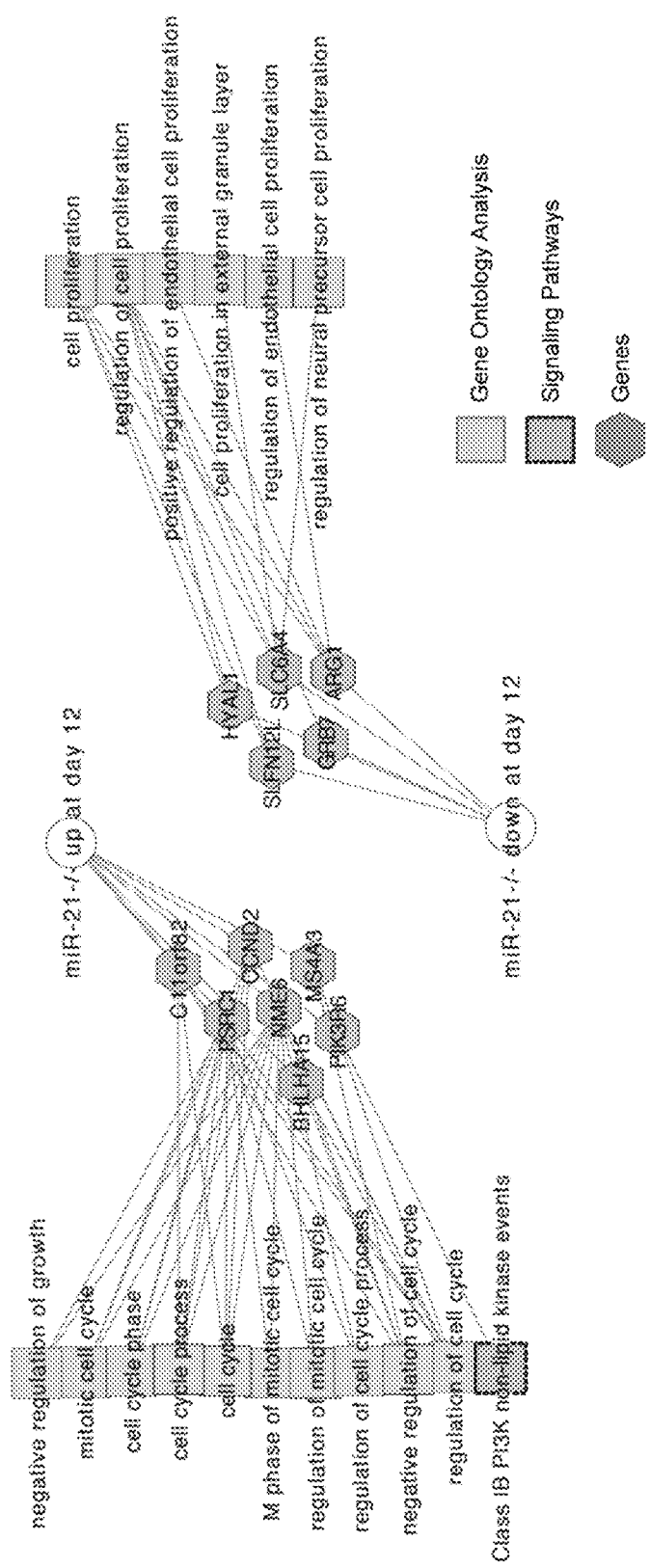
Figure 16:
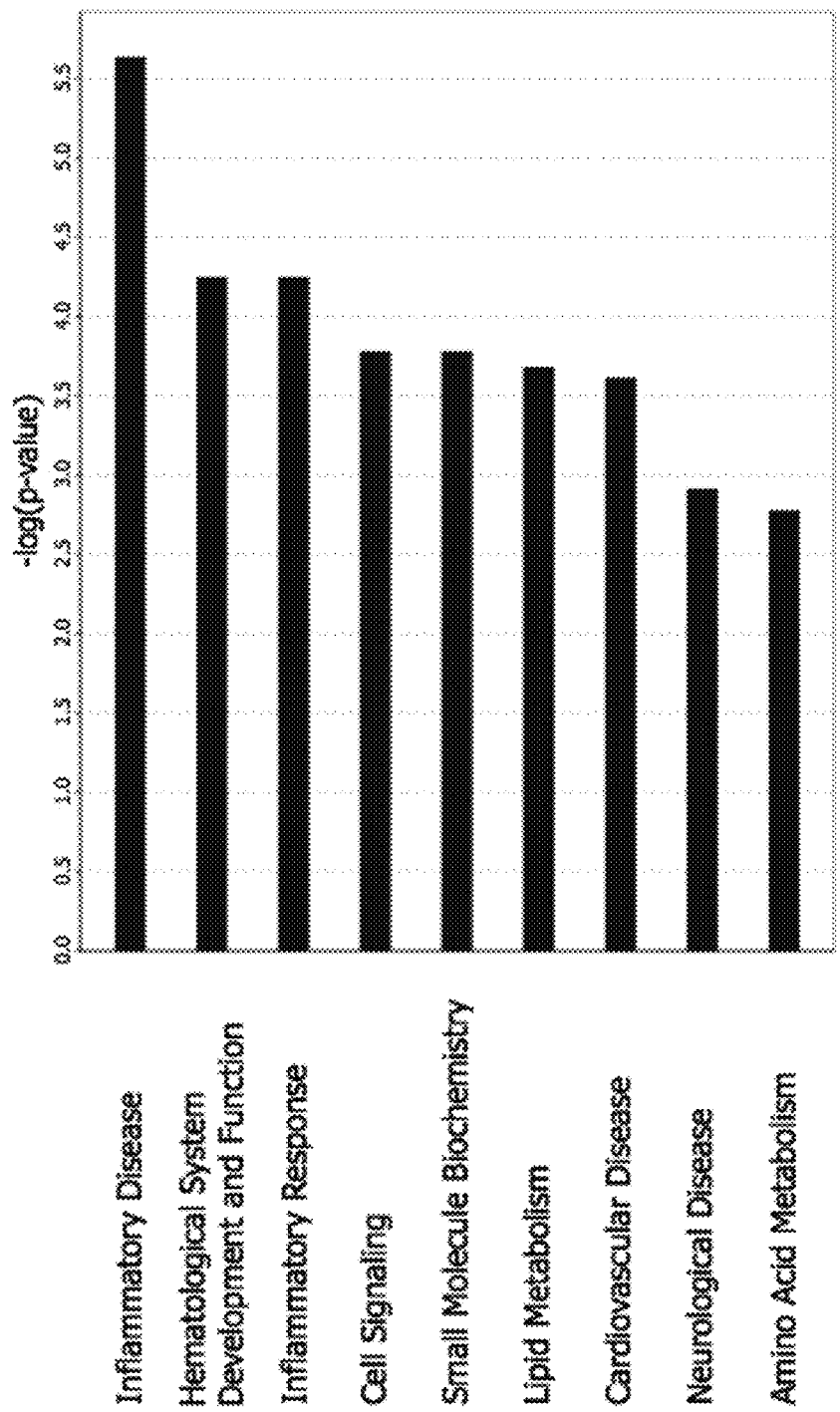
FIG. 16 depicts a biological function enrichment analysis of differentially regulated genes in eosinophil progenitor cultures at day 8. The figure illustrates an analysis of the most significant biological functions represented by the differentially regulated genes between miR-21$^{+/+}$ and miR-21$^{-/-}$ eosinophil progenitor cultures.

To validate the differentially expressed genes, qRT-PCR was performed on a selected set of differentially expressed genes, including PIK3R6, MS4A3, PSRC1 and GRB7 (FIG. 15C). Functional enrichment analysis of the differentially regulated genes identified regulation cell growth and cell cycle as the most significantly enriched pathways at day 12 (FIG. 15D). The top affected biological functions were hematological system development and function, inflammatory disease and response, and cell signaling (FIG. 16).

TABLE 6

List of differentially regulated genes between miR-21$^{+/+}$ and miR-21$^{-/-}$ eosinophil progenitor cultures at day 8.

| Transcript ID | Gene Symbol | Gene Description | Fold Change | Regulation |
|---|---|---|---|---|
| 10362442 | Trdn | Triadin | 1.53 | Up-regulated |
| 10363224 | Fabp7 | Fatty acid binding protein 7, brain | 1.73 | Up-regulated |
| 10377286 | Pik3r6 | Phosphoinositide-3-kinase, regulatory subunit 6 | 1.79 | Up-regulated |
| 10380226 | Cuedc1 | CUE domain containing 1 | 2.00 | Up-regulated |
| 10536294 | Peg10 | Paternally expressed 10 | 1.52 | Up-regulated |
| 10544610 | Igf2bp3 | Insulin-like growth factor 2 mRNA binding protein 3 | 1.74 | Up-regulated |
| 10583056 | Mmp12 | Matrix metallopeptidase 12 | 1.67 | Up-regulated |

Example 16

Expression of MiR-223 in an Ex Vivo Culture of Bone Marrow Derived Eosinophils

A study was conducted to determine the role of miR-223 in eosinophil development and function. A murine ex vivo bone marrow-derived eosinophil culture model that generates >90% eosinophils after 14 days of culture was utilized (Dyer, K. et al. *J. Immunol.* 181:4004-9 (2008)).

Mice

MiR-223 gene targeted mice were backcrossed for 5 generations into the C57BL/6 background, as described in a previous protocol (Lu, T. et al. *J. Immunol.* 187:3362-73 (2011)). Littermate controls were used for all experiments. All animals used were housed under specific pathogen-free conditions in accordance with institutional guidelines. The Institutional Animal Care and Use Committee of the Cincinnati Children's Hospital Medical Center approved the use of animals in these experiments.

Bone Marrow-Derived Eosinophil Cultures

Bone marrow cells were collected from femurs and tibia of the mice, and the stem/progenitor cell-enriched low-

TABLE 7

List of differentially regulated genes between miR-21$^{+/+}$ and miR-21$^{-/-}$ eosinophil progenitor cultures at day 12.

| Transcript ID | Gene Symbol | Gene Description | Fold Change | Regulation |
|---|---|---|---|---|
| 10354732 | Hspd1 | Heat shock protein 1 (chaperonin) | 1.54 | Up-regulated |
| 10364093 | Derl3 | Derl1-like domain family, member 3 | 1.53 | Up-regulated |
| 10377286 | Pik3r6 | Phosphoinositide-3-kinase, regulatory subunit 6 | 1.67 | Up-regulated |
| 10384398 | Grb10 | Growth factor receptor bound protein 10 | 1.76 | Up-regulated |
| 10425287 | Kdelr3 | KDEL (Lys-Asp-Glu-Leu) endoplasmic reticulum protein retention receptor 3 | 1.53 | Up-regulated |
| 10466224 | Ms4a3 | Membrane-spanning 4-domains, subfamily A, member 3 | 1.88 | Up-regulated |
| 10489343 | Ptpla | Protein tyrosine phosphatase-like (proline instead of catalytic arginine), member a | 1.53 | Up-regulated |
| 10495316 | Psrc1 | Proline/serine-rich coiled-coil 1 | 1.51 | Up-regulated |
| 10527323 | Bhlha15 | Basic helix-loop-helix family, member a15 | 1.57 | Up-regulated |
| 10542857 | Far2 | Fatty acyl CoA reductase 2 | 1.52 | Up-regulated |
| 10548105 | Ccnd2 | Cyclin D2 | 1.51 | Up-regulated |
| 10559818 | N/A | N/A | 1.50 | Up-regulated |
| 10565570 | 4632434I11Rik | RIKEN cDNA 4632434I11 gene | 1.66 | Up-regulated |
| 10574572 | 2210023G05Rik | RIKEN cDNA 2210023G05 gene | 1.58 | Up-regulated |
| 10589413 | Nme6\|LOC100046163\|LOC100046157 | Non-metastatic cells 6, protein expressed in (nucleoside-diphosphate kinase)\|similar to Nme6 protein\|hypothetical protein LOC100046157 | 1.52 | Up-regulated |
| 10345752 | Il1r2 | Interleukin 1 receptor, type II | −2.16 | Down-regulated |
| 10368343 | Arg1 | Arginase, liver | −4.84 | Down-regulated |
| 10374248 | Abca13 | ATP-binding cassette, sub-family A (ABC1), member 13 | −1.90 | Down-regulated |
| 10377782 | Clec10a | C-type lectin domain family 10, member A | −2.69 | Down-regulated |
| 10378816 | Slc6a4 | Solute carrier family 6 (neurotransmitter transporter, serotonin), member 4 | −3.98 | Down-regulated |
| 10379630 | Slfn2 | Schlafen 2 | −2.06 | Down-regulated |
| 10379710 | E230016K23Rik | RIKEN cDNA E230016K23 gene | −1.64 | Down-regulated |
| 10380566 | Phospho1\|Abi3 | Phosphatase, orphan 1\|ABI gene family, member 3 | −1.59 | Down-regulated |
| 10380927 | Grb7 | Growth factor receptor bound protein 7 | −1.56 | Down-regulated |
| 10436095 | Retnla | Resistin like alpha | −2.99 | Down-regulated |
| 10467979 | Scd1 | Stearoyl-Coenzyme A desaturase 1 | −2.00 | Down-regulated |
| 10483228 | Scn3a | Sodium channel, voltage-gated, type III, alpha | −1.55 | Down-regulated |
| 10491313 | Cldn11 | Claudin 11 | −1.62 | Down-regulated |
| 10570291 | F10 | Coagulation factor X | −2.01 | Down-regulated |
| 10585068 | Fam55d | Family with sequence similarity 55, member D | −1.51 | Down-regulated |
| 10588691 | Hyal1\|Nat6 | Hyaluronoglucosaminidase 1\|N-acetyltransferase 6 | −1.50 | Down-regulated |
| 10598010 | Ccrl1 | Chemokine (C-C motif) receptor 1-like 1 | −1.55 | Down-regulated | density fraction was isolated by gradient centrifugation using the Histopaque 1083 (Sigma), according to the manufacturer's protocol. The low density fraction of bone marrow cells were cultured in IMDM with 10% FBS, 100 U/ml penicillin, and 100 μg/ml streptomycin supplemented with 100 ng/mL stem cell factor and 100 ng/mL FLT-3 ligand (Peprotech) from day 0 to day 4.

Figure 17A:
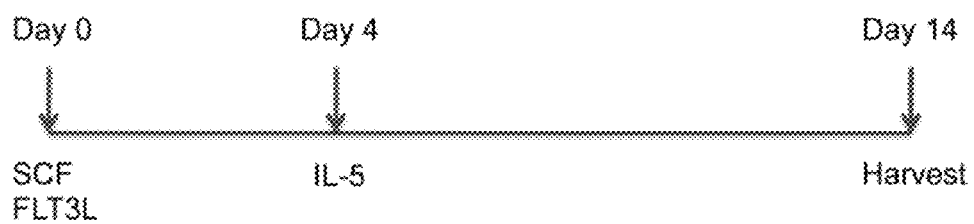
FIGS. 17A-C depict miR-223 induction during eosinophil differentiation.

The stem cell factor and FLT-3 ligand were replaced with 10 ng/mL IL-5 on day 4, and the cells were cultured for an additional 10-12 days in the presence of IL-5 (Dyer, K. et al. *J. Immunol.* 181:4004-9 (2008)). The culture media was changed every other day, and cells were counted and concentration was adjusted to $1 \times 10^6$/mL during each media change. Eosinophil maturity was assessed by FACS staining for CCR3 and Siglec-F and/or Diff-Quik (Fisher Scientific) staining of cytospin preparations. Eosinophil progenitor growth was assessed by counting the cells every 2 days using a hemacytometer. The schematic for the culture of bone marrow-derived eosinophils is shown in FIG. 17A.

Quantitative Assessment of miRNA Levels

Total RNA was isolated using the miRNeasy Mini Kit (Qiagen), according to the manufacturer's protocols. Levels of miRNA expression were measured quantitatively by using the TaqMan MicroRNA Assay (Applied Biosystems), following the manufacturer's protocol, and assayed on the 7900HT Real-Time PCR System (Applied Biosystems). Normalization was performed using U6 small nuclear RNA. Relative expression was calculated using the comparative $C_T$ method, as described in a previous protocol (Livak, K. et al. *Method.* 25:402-8 (2001)).

Statistical Analysis

Statistical analyses were performed with student's t-test or one-way ANOVA with Tukey post-hoc test where appropriate. Statistical significance and the p values were indicated on the figures where appropriate. P values less than 0.05 were considered statistically significant.

Results

Figure 17B:
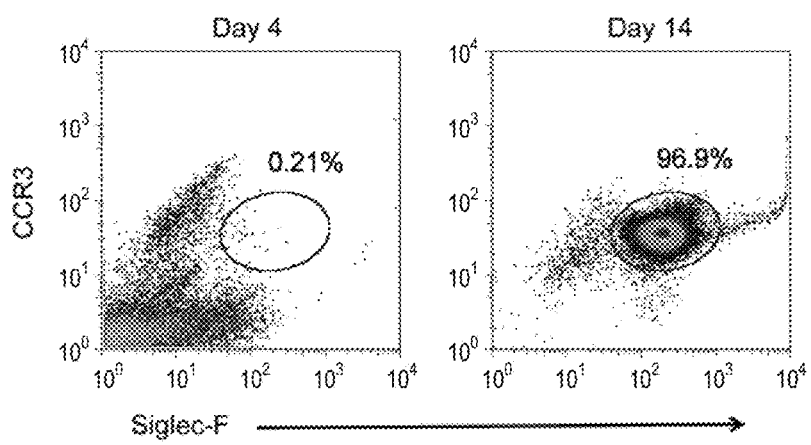
Figure 17C:
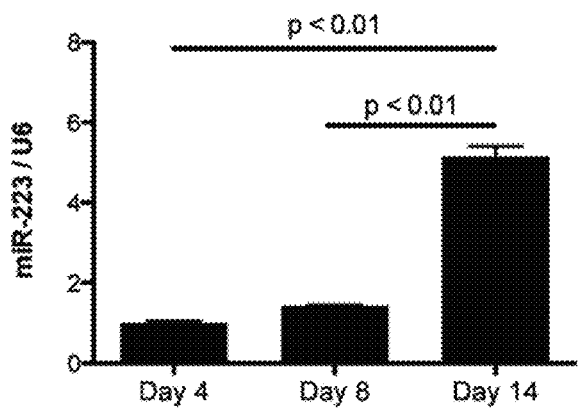

High purity ex vivo bone marrow-derived eosinophils were obtained, as determined by FACS staining for CCR3 and Siglec-F double positive cells, on day 14 (FIG. 17B). Up-regulation of miR-223 was observed during the eosinophil differentiation culture from day 4 to day 14 (FIG. 17C), with the most prominent difference seen between days 8 and 14.

Example 17

Figure 18A:
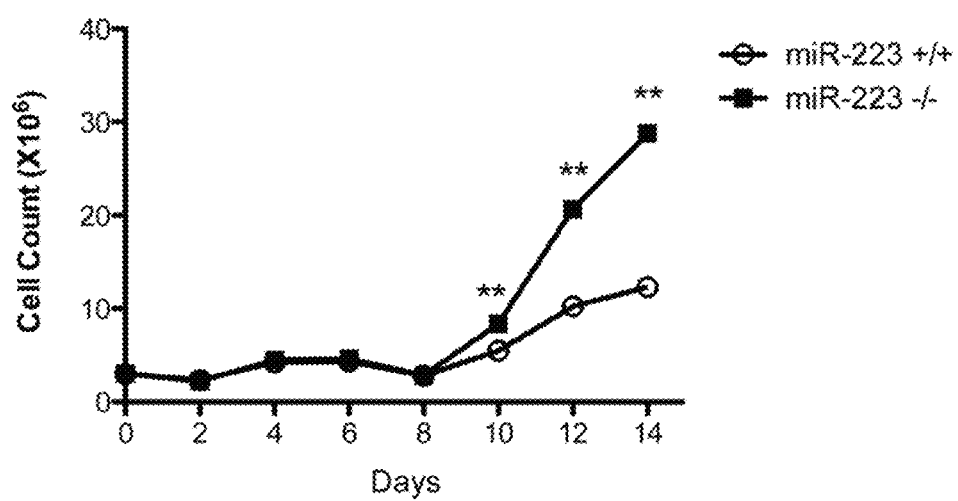
FIGS. 18A-C depict the growth of eosinophil progenitor cells and morphology of mature eosinophils from miR-223$^{+/+}$ and miR-223$^{-/-}$ cultures during the ex vivo eosinophil differentiation culture.
Figure 18B:
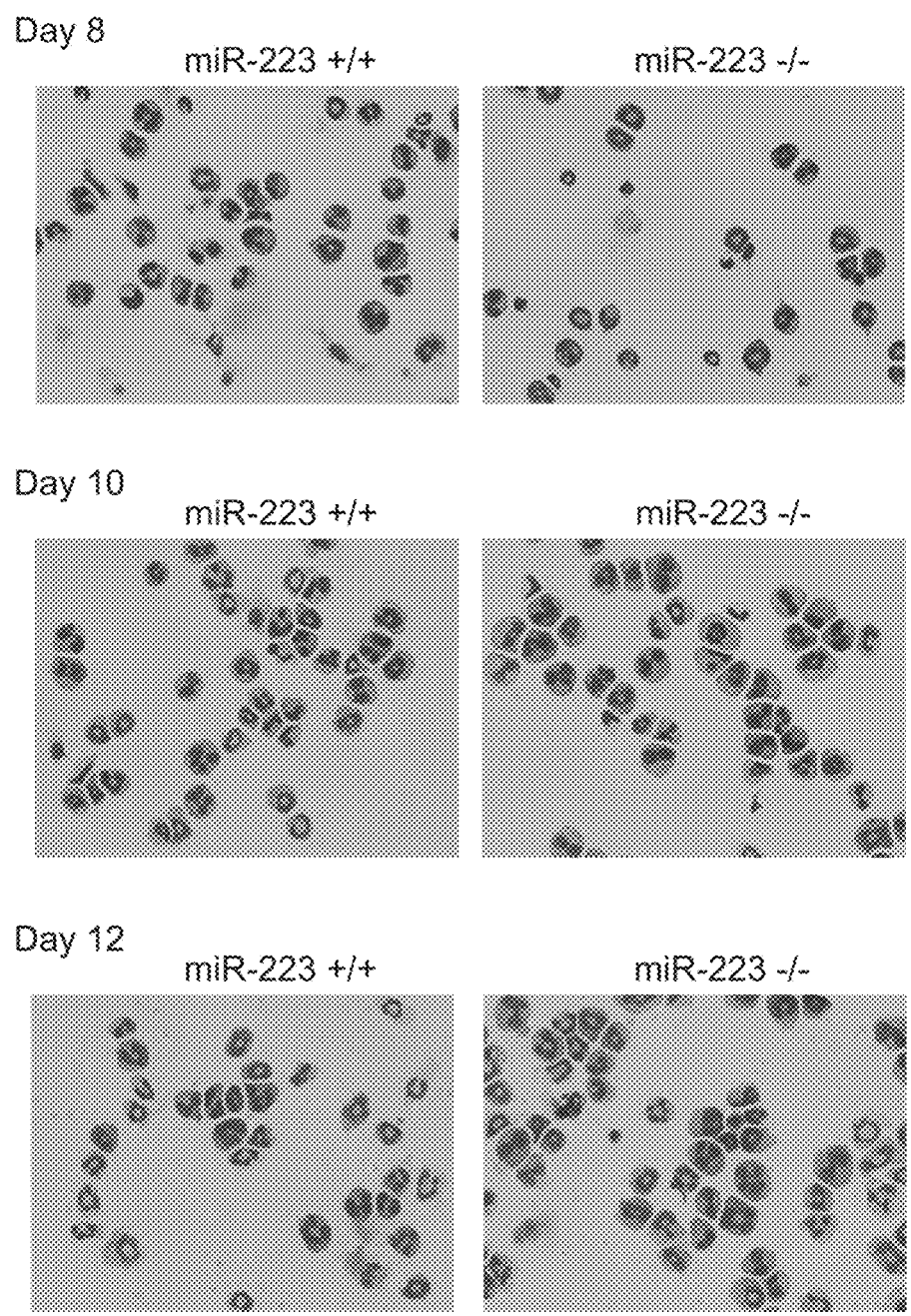
Figure 18C:
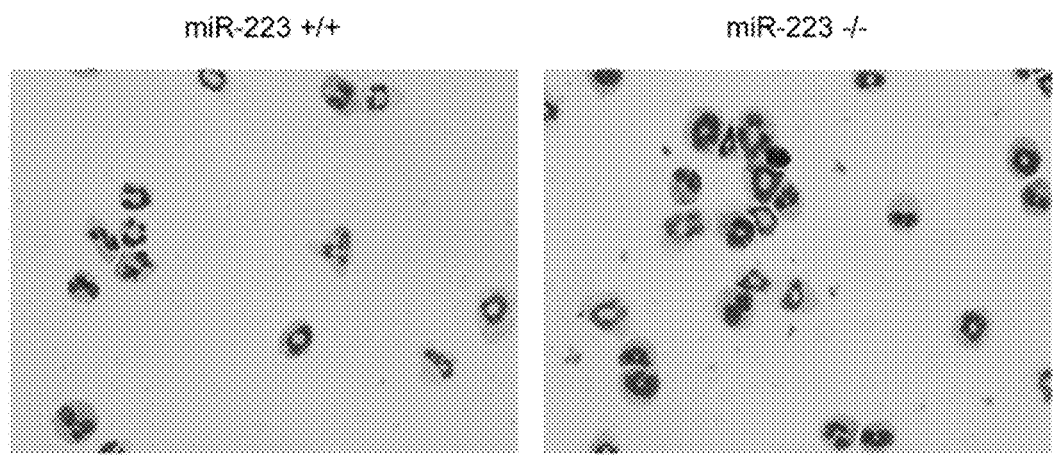

Enhanced Eosinophil Progenitor Proliferation in Eosinophil Cultures Derived from MiR-223$^{-/-}$ Mice In the same study, the effect of miR-223 on the proliferation of eosinophil progenitor cells was determined by culturing bone marrow-derived eosinophils from miR-223$^{-/-}$ mice. Compared to cultures from the wild type littermate controls, the miR-223$^{-/-}$ eosinophil progenitor cultures had a markedly increased proliferation, with the most prominent effect seen between day 10 and day 14 (FIG. 18A). Morphology was monitored at days 8, 10, and 12 (FIG. 18B). The miR-223 and miR-223$^{-/-}$ bone marrow-derived eosinophils were morphologically indistinguishable from each other at day 14 (FIG. 18C).

Example 18

Up-Regulation of IGF1 Receptor in Eosinophil Cultures Derived from MiR-223$^{-/-}$ Mice In the same study, IGF1 receptor (IGF1R) levels were evaluated to determine whether they were differentially regulated between eosinophil cultures derived from miR-223$^{-/-}$ mice and miR-223$^{+/+}$ littermate controls. IGF1 has heretofore not been examined for its impact on eosinophils or their progenitors.

Preparation of Total Cell Lysates and Western Blot

Cells were rapidly washed in phosphate buffered saline and lysed in M-PER mammalian protein extraction reagent (Pierce, Rockford, Ill.), according to the manufacturer's protocol. Protease inhibitor cocktails (Pierce) and phosphatase inhibitor cocktails (Pierce) were added to the M-PER protein extraction reagent immediately before lysis. Western blot analysis was performed, as described in a previous protocol (Lim, E. et al. *J. Biol. Cheng.* 286:13193-204 (2011)). The assay was conducted using an anti-IGF1R antibody (Cell Signaling Technology, Danvers, Mass.) and an anti-GAPDH antibody (Abcam, Cambridge, UK).

Results

Figure 19:
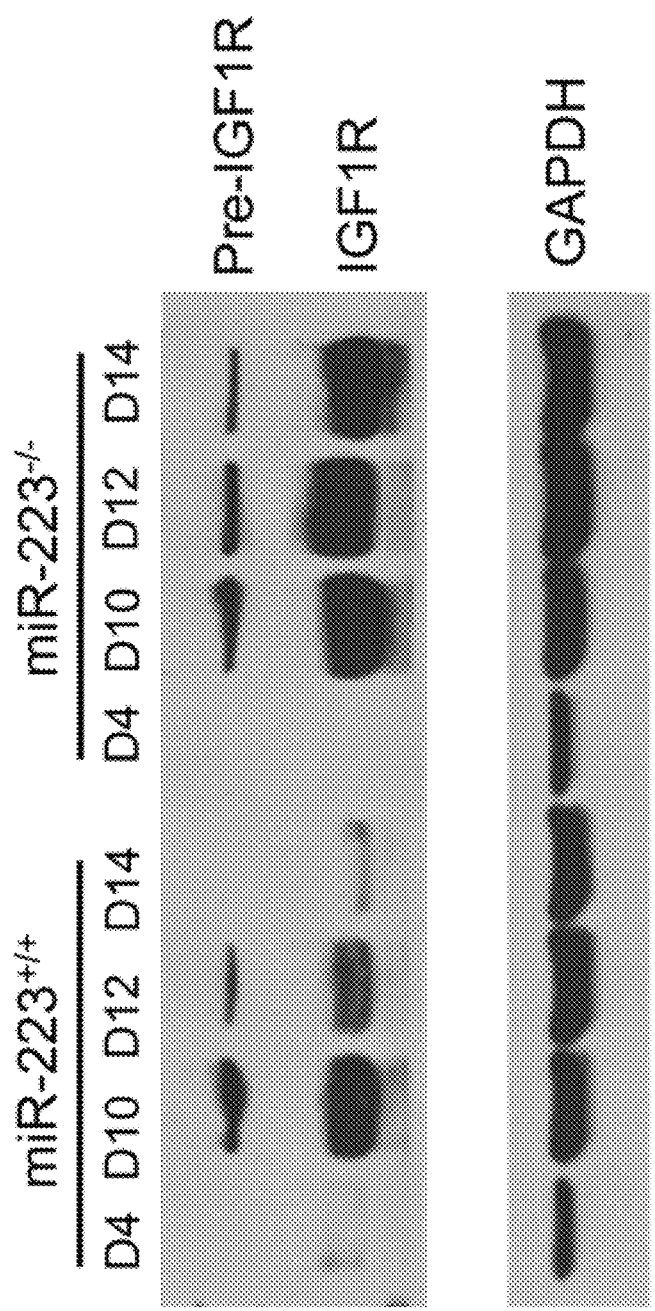
FIG. 19 depicts levels of IGF1R during eosinophil differentiation culture from the miR-223$^{+/+}$ and miR-223$^{-/-}$ mice. The figure presents a western blot showing levels of pre-IGF1R and IGF1R in eosinophil differentiation cultures derived from miR-223$^{+/+}$ and miR-223$^{-/-}$ mice from day 4 to day 14. The housekeeping gene glyceraldehyde 3-phosphate dehydrogenase (GAPDH) was used as a loading control.

IGF1R was not found to be expressed at day 4, indicating that proliferation of progenitor cells under the influence of stem cell factor and FLT-3 ligand is not dependent on IGF1R levels. Significant levels of IGF1R expression were found from day 10 to day 14 of the culture, coinciding with the increased proliferation seen in both the miR-223$^{+/+}$ and miR-223$^{-/-}$ eosinophil cultures (FIG. 18A, FIG. 19). However, in the miR-223$^{+/+}$ cultures, the IGF1R level progressively decreased from day 10 to day 14, reflecting that eosinophil progenitors gradually lose their proliferation capacity during the differentiation process (FIG. 18A, FIG. 19). Compared to the miR-223$^{+/+}$ cultures, the miR-223$^{-/-}$ cultures have significantly increased levels of IGF1R at both day 12 and day 14 (FIG. 19).

Example 19

Reversibility of Increased Proliferation in MiR-223$^{-/-}$ Eosinophil Cultures by Treatment with an IGF1R Inhibitor A subsequent study was undertaken to determine whether the up-regulation of IGF1R was responsible for the increased proliferation seen in eosinophil cultures derived from the miR-223$^{-/-}$ mice.

Analysis of Cell Proliferation after Picropodophyllin Treatment

Bone marrow-derived eosinophils were re-suspended at a concentration of $1 \times 10^6$ cells/ml and treated with DMSO or 2 μM of picropodophyllin at day 8 (Yin, S. et al. *Neuro. Oncol.* 12:19-27 (2010)). Cell growth was determined by cell counting using a hemacytometer on day 10 and day 12. Cell lysates were collected on day 10, and levels of IGF1R expression were determined by western blot.

Bone marrow-derived eosinophils were resuspended at a concentration of $1 \times 10^6$ cells/mL and plated in a 96 well plate at 100 μL per well on day 9 to determine a dose response curve of picropodophyllin. The cells were treated with increasing concentrations of picropodophyllin, and the level of cell growth was determined using Cell-Titer Glo luminescent cell viability assay (Promega, Madison, Wis.), according to the manufacturer's protocol.

Results

Eosinophil cultures were treated on day 8 with 2 μM of picropodophyllin, an IGF1R inhibitor, or an equivalent volume of dimethyl sulfoxide (DMSO) as a control. DMSO treatment had no effect on eosinophil proliferation.

Figure 20A:
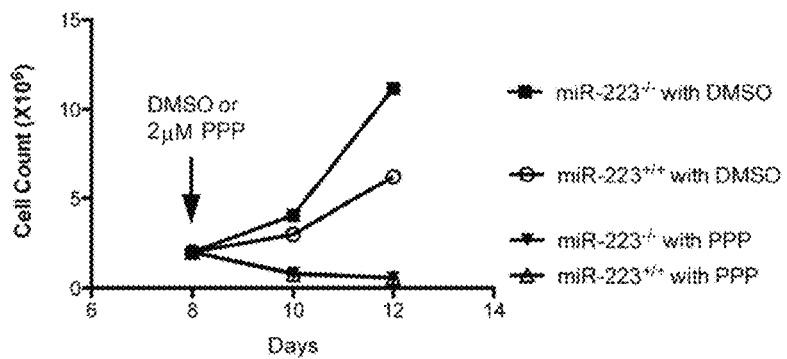
FIGS. 20A-C depict the finding that the increased growth observed in cultures derived from miR-223$^{-/-}$ mice can be reversed by an IGF1R inhibitor.

The miR-223$^{-/-}$ cultures treated with DMSO had significant increases in growth compared to DMSO-treated miR-223$^{+/+}$ cultures (FIG. 20A), confirming the results shown in FIG. 18C. In contrast, treatment with 2 μM of picropodophyllin inhibited the growth of both miR-223$^{+/+}$ and miR-223$^{-/-}$ cultures to a similar extent (FIG. 20A), completely reversing the increased proliferation seen in miR-223$^{-/-}$ cultures.

Figure 20B:
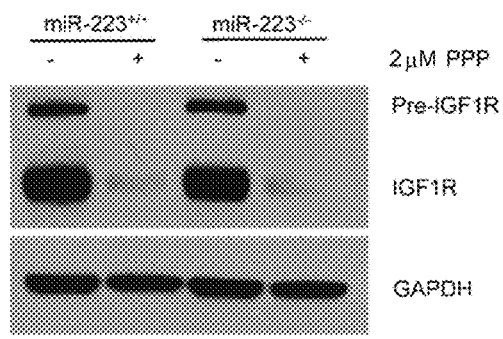
Figure 20C:
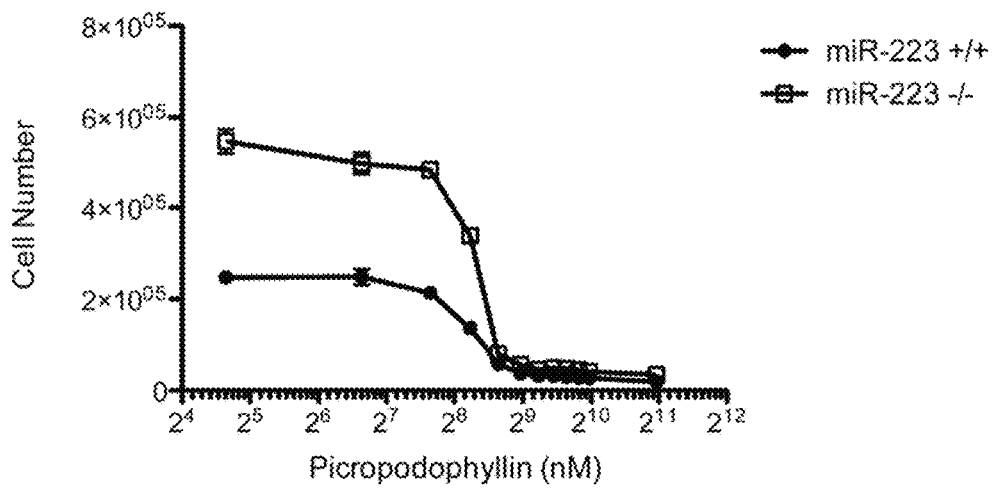

The levels of IGF1R expression were analyzed on day 10 with or without picropodophyllin treatment. Picropodophyllin was found to induce a nearly complete down-regulation of IGF1 receptor in both the miR-223$^{+/+}$ and miR-223$^{-/-}$ cultures (FIG. 20B). Dose-response demonstrated that picropodophyllin inhibited miR-223$^{+/+}$ and miR223$^{-/-}$ eosinophil progenitor growth with similar IC$_{50}$ (FIG. 20C).

Example 20

Figure 21A:
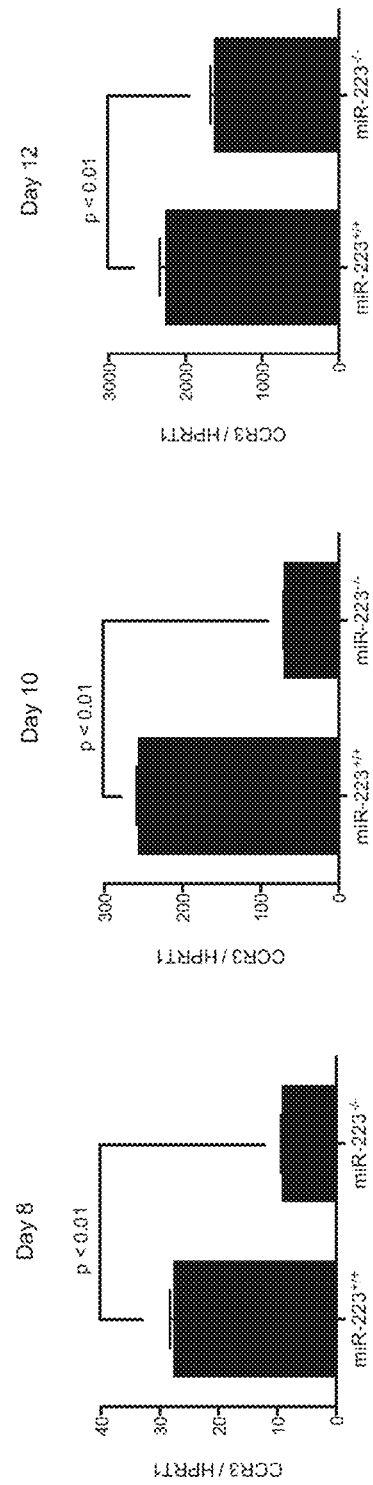
FIGS. 21A-B depict the increased growth observed in eosinophil progenitor cultures derived from miR-223$^{-/-}$ mice, coupled with a delay in eosinophil progenitor differentiation.
Figure 21B:
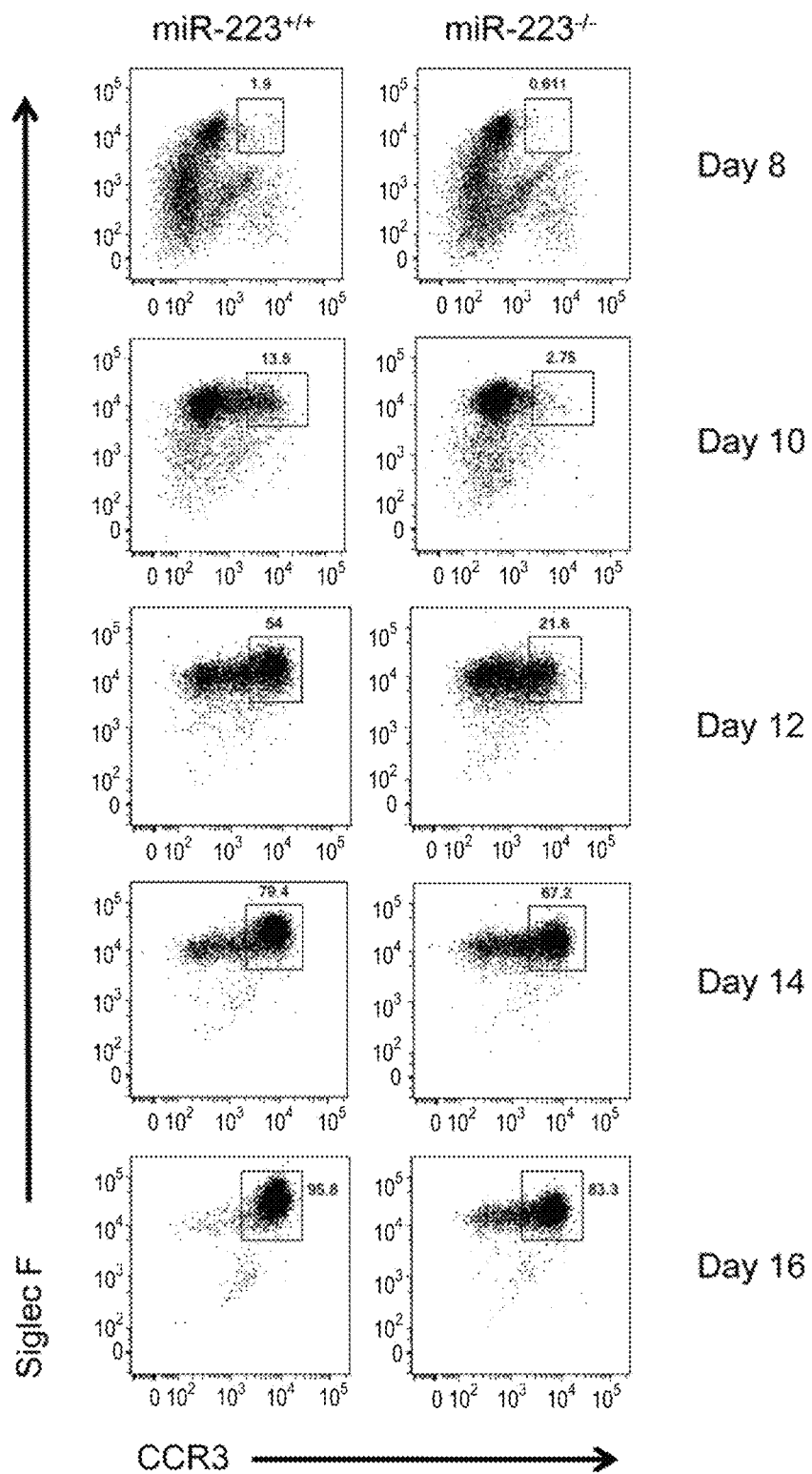

Association Between Increased Proliferation Observed in MiR-223$^{-/-}$ Eosinophil Progenitor Cultures and Delay in Differentiation In the same study, a delayed up-regulation of CCR3 and delayed down-regulation of CD34 in miR-223$^{-/-}$ eosinophil progenitor cultures was observed compared to miR-223$^{+/+}$ eosinophil progenitor cultures, indicative of delayed maturation of the miR-223$^{-/-}$ eosinophil progenitor cells. qPCR analysis of the CCR3 level was performed on day 8, day 10, and day 12 eosinophil progenitor cultures. To determine the surface expression of CCR3 during the eosinophil progenitor culture, FACS analysis of CCR3 and Siglec-F expression was performed from day 8 to day 16 of eosinophil culture.
qRT-PCR for mRNA Total RNA was reverse transcribed using the High Capacity cDNA Reverse Transcription kit (Applied Biosystems). All primer/probe sets were obtained from Applied Biosytems (Applied Biosystems). Samples were analyzed by the TaqMan qRT-PCR (Applied Biosystems) for CCR3 (Assay ID: Mm01216172_m1) and normalized to HPRT1 (Assay ID: Mm00446968_m1). Relative expression was calculated using the comparative C$_T$ method.
Flow Cytometry Analysis of Eosinophil Surface CCR3 Expression One million cultured eosinophil progenitor cells were stained with CCR3-FITC (R&D Systems) and SiglecF-PE (BD Bioscience), which are markers for mature eosinophils. Staining was performed on ice for 30 minutes in staining buffer (0.5% BSA, 0.01% NaN$_3$ in 1×HBSS), according to the manufacturer's protocol (R&D Systems and BD Biosciences). Data was acquired on a BD FACS Canto I flow cytometer (BD Biosciences) and analyzed using FlowJo (TreeStar, Ashland, Oreg.).
Results MiR-223$^{-/-}$ eosinophil progenitors were found to have delayed up-regulation of CCR3 compared with miR-223$^{+/+}$ eosinophil progenitors at all three time points (FIG. 21A), indicative of delayed maturation of the miR-223$^{-/-}$ eosinophil progenitor cells. The mature eosinophils were CCR3$^+$ and Siglec-F$^+$. There were less than 2% CCR3$^+$ Siglec-F$^+$ cells during the eosinophil culture on day 8, indicating that nearly all cells were in the progenitor stage in both the miR-223$^{+/+}$ and miR-223$^{-/-}$ cultures (FIG. 21B). While CCR3$^+$ SigleeF$^+$ cells begin to appear on day 10, there were substantially fewer CCR3$^+$ SigleeF$^+$ cells in the miR-223$^{-/-}$ cultures than in the miR-223$^{+/+}$ cultures. This difference is most pronounced during day 10 and day 12 of the eosinophil progenitor culture (FIG. 21B), concomitant with the onset of the increased proliferation seen in the miR-223$^{-/-}$ cultures (FIG. 18A).

Figure 22A:
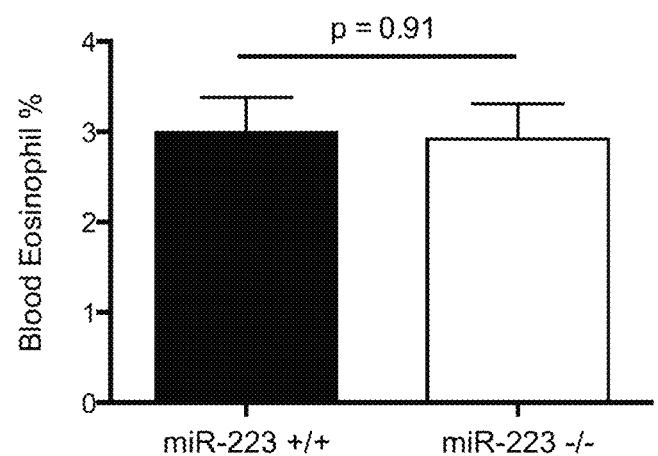
FIGS. 22A-B depict the mature eosinophil levels in the blood and eosinophil progenitor levels in the bone marrow of miR-223$^{+/+}$ and miR-223$^{-/-}$ mice.
Figure 22B:
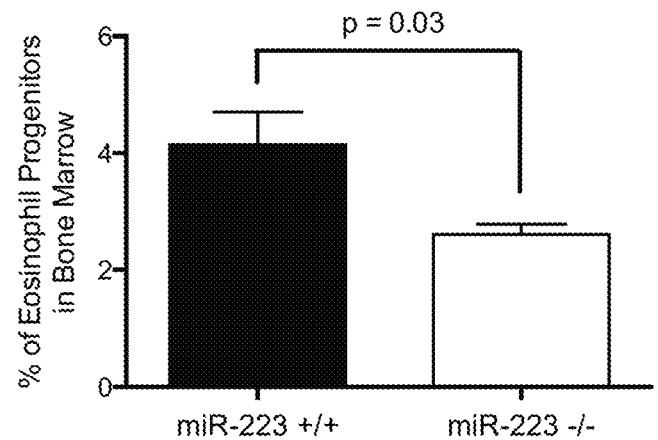

The blood eosinophil levels were measured in vivo, and no difference was found between the miR-223$^{+/+}$ and miR-223$^{-/-}$ mice (FIG. 22A). This is likely due to in vivo compensation at the stage where multipotent progenitors are differentiated into eosinophil lineage-committed progenitors. When the level of IL5Ra$^+$ CCR3$^+$ eosinophil lineage-committed progenitors was measured in vivo, a decreased level of eosinophil lineage-committed progenitors was found in the miR-223$^{-/-}$ mice (FIG. 22B). These results demonstrate that the increased proliferation of the miR-223$^{-/-}$ eosinophil progenitors is associated with a delay in eosinophil differentiation.

Example 21

Figure 23A:
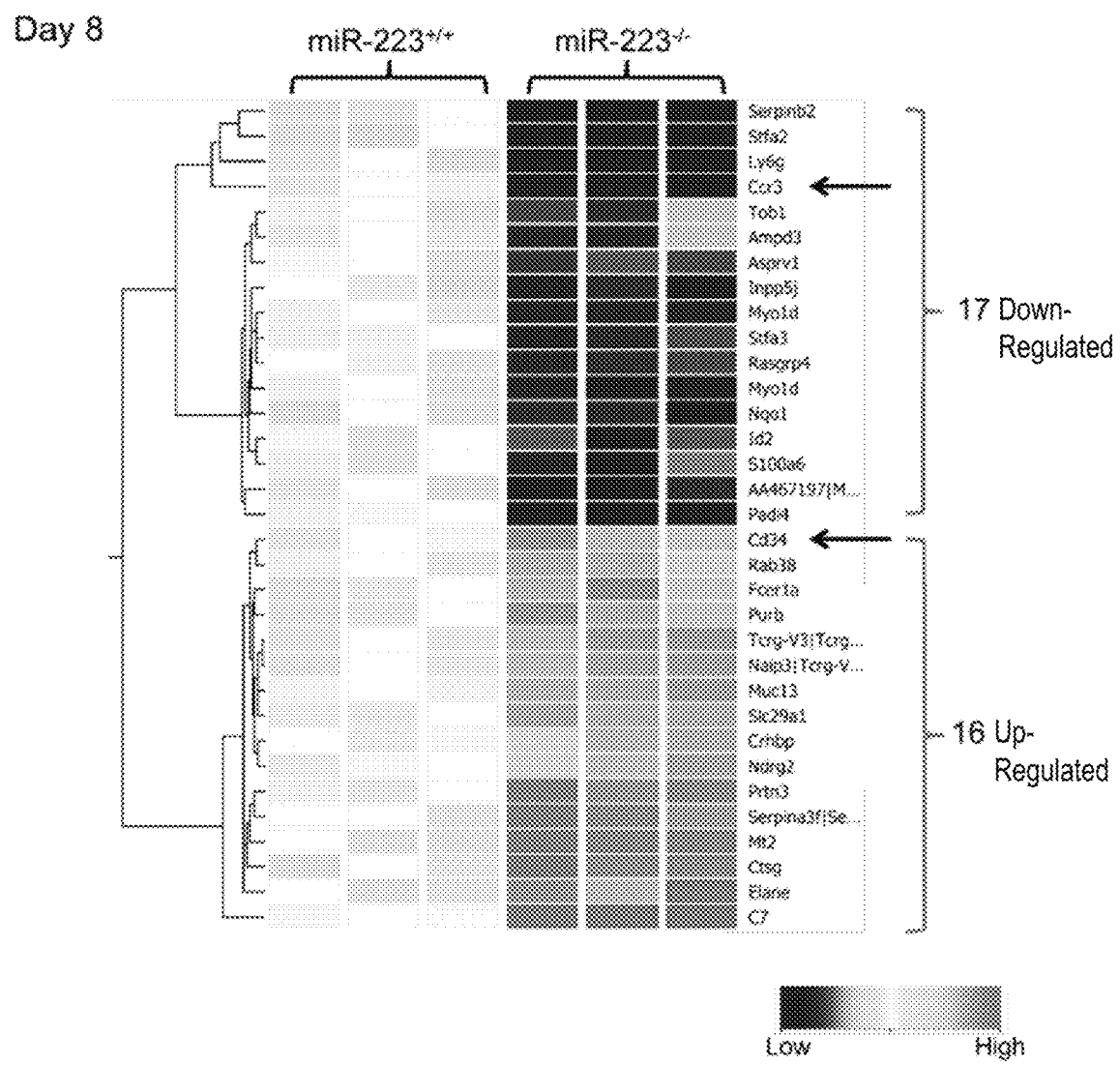
FIGS. 23A-D present heatmaps of differentially regulated genes between miR-223$^{+/+}$ and miR-223$^{-/-}$ eosinophil progenitor cultures at day 8 and day 12, along with their most strongly associated biological functions.
Figure 23B:
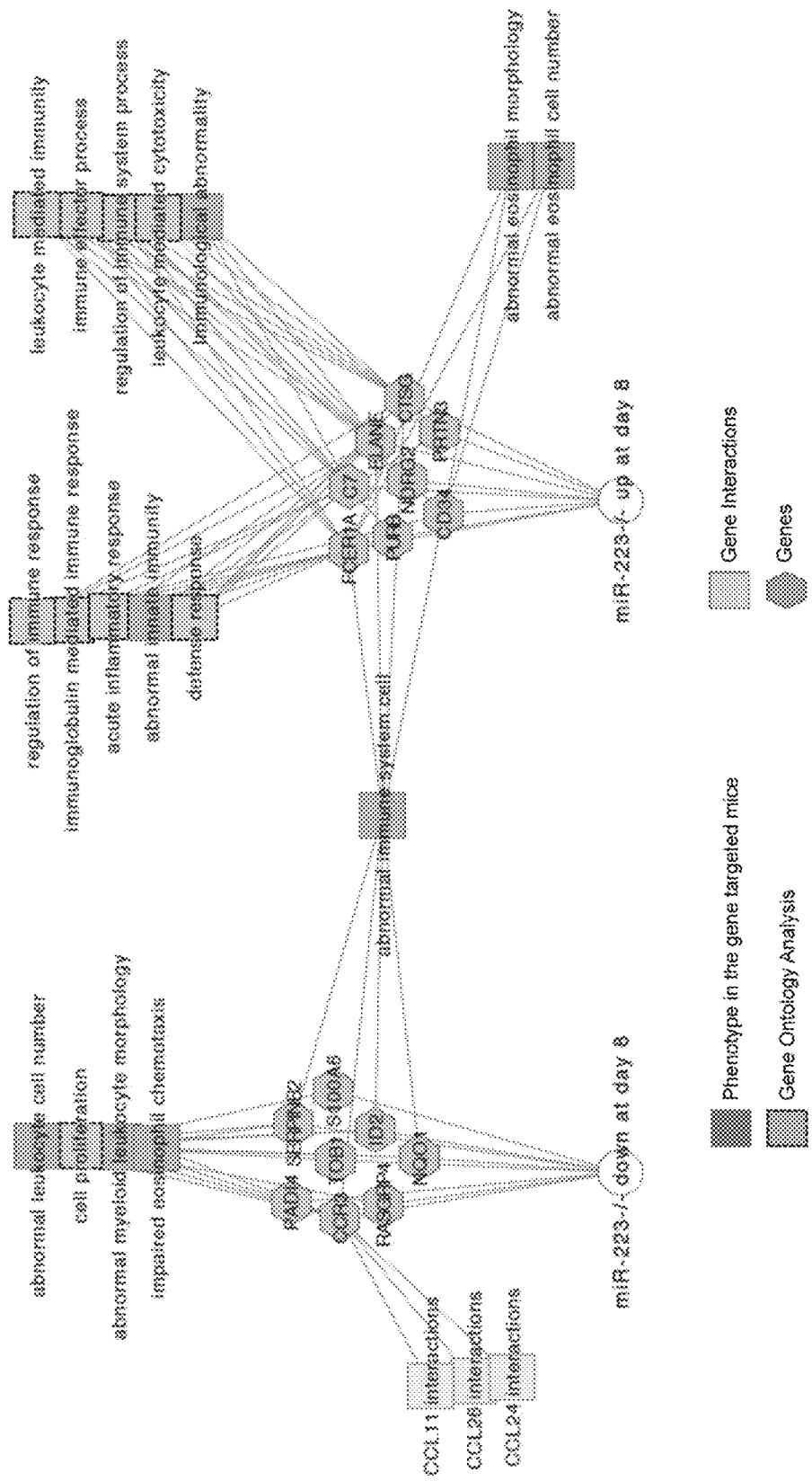
Figure 23C:
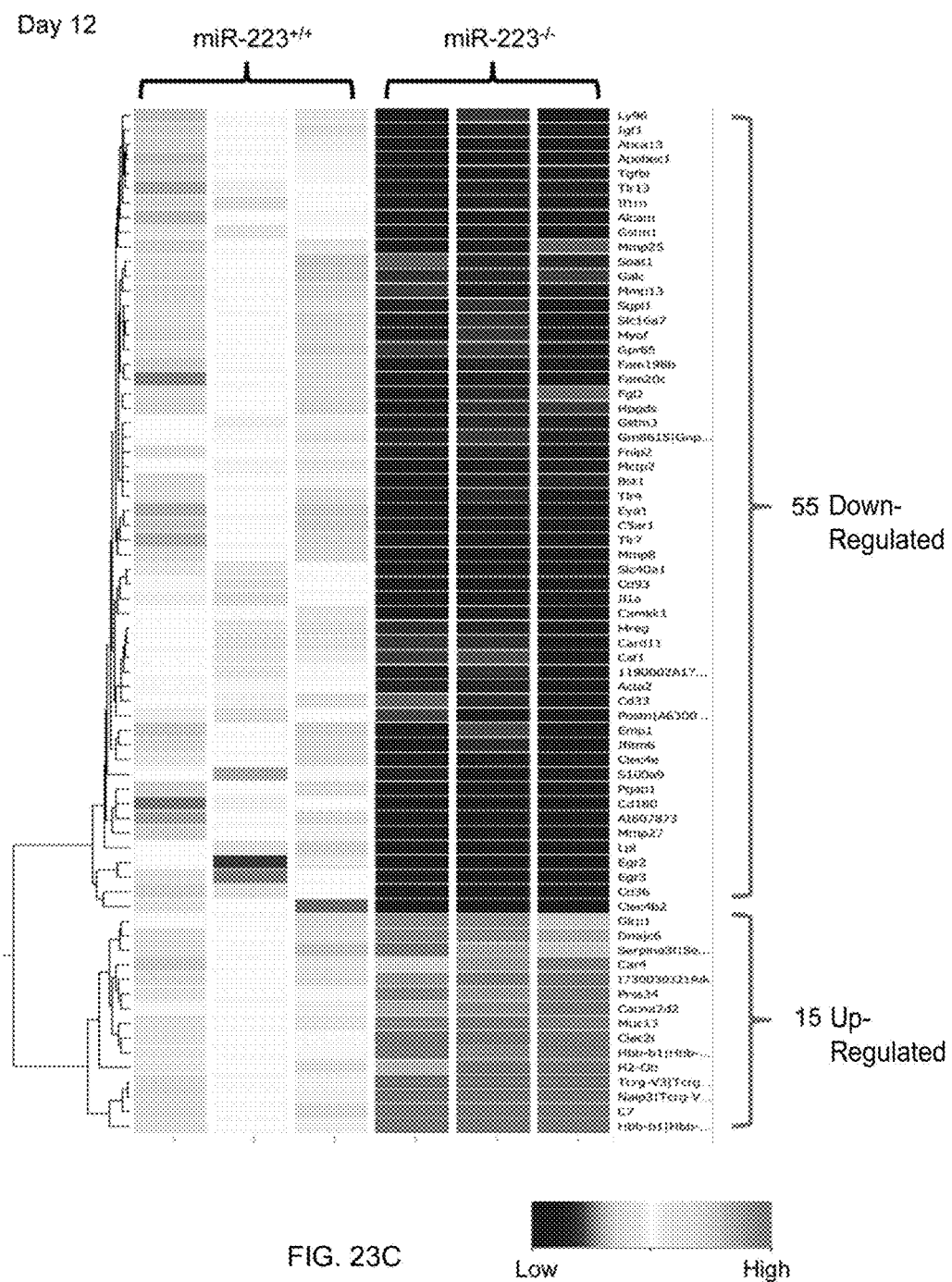
Figure 23D:
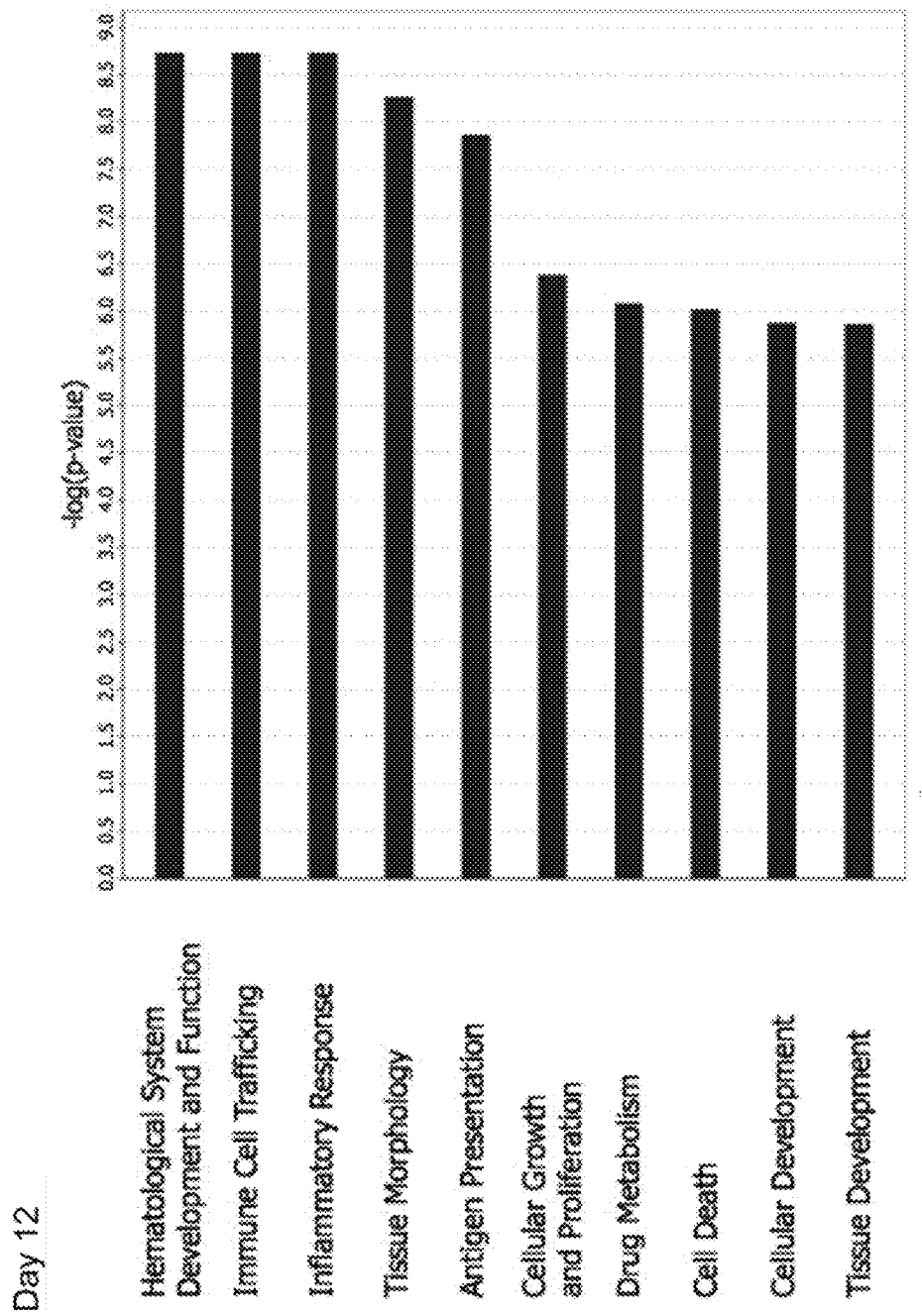
Figure 24:
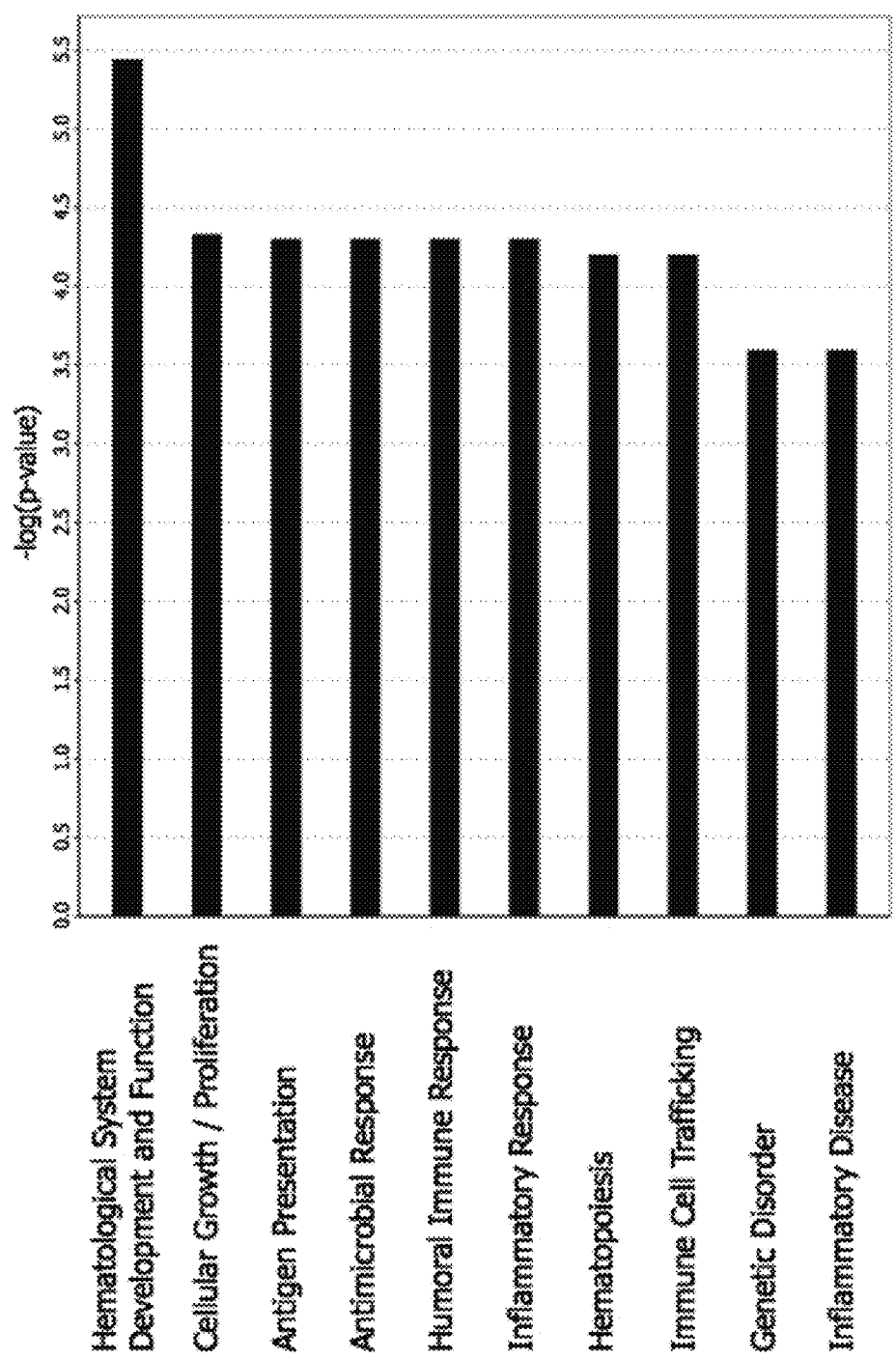
FIG. 24 depicts a biological function enrichment analysis of differentially regulated genes in eosinophil progenitor cultures at day 8. The figure illustrates an analysis of the most significant biological functions represented by the differentially regulated genes between miR-223$^{+/+}$ and miR-223$^{-/-}$ eosinophil progenitor cultures.

Genes Found to be Differentially Regulated between MiR-223$^{+/+}$ and MiR-223$^{-/-}$ Eosinophil Progenitor Cultures Having identified a decreased differentiation of miR223$^{31}$/- eosinophils using a targeted approach (focusing on CCR3 and Siglec-F), a subsequent study was conducted to extend this finding at a genome-wide level to identify genes differentially expressed during the eosinophil progenitor culture. A gene expression microarray analysis was performed on the eosinophil progenitor cultures on days 4, 8, and 12.
Mouse Genome-Wide mRNA Microarray The Mouse Gene 1.0ST array (Affymetrix) was used to compare gene expression profiles between miR-223$^{+/+}$ and miR-223$^{-/-}$ eosinophil progenitor cultures at day 4, day 8, and day 12. Microarray data were analyzed using Gene-Spring software (Agilent Technologies). Global scaling was performed to compare genes from chip to chip, and a base set of probes was generated by requiring a minimum raw expression level of 20$^{th}$ percentile out of all probes on the microarray. The resulting probe sets were then baseline transformed and filtered on at least a 1.5-fold difference between miR-223$^{+/+}$ and miR-223$^{-/-}$ eosinophil progenitor cultures. Statistical significance was determined at p<0.05 with Benjamini Hochberg false discovery rate correction. The resulting list of genes was clustered using hierarchical clustering, and a heatmap was generated. Biological functional enrichment analysis was carried out using Ingenuity Pathway Analysis (Ingenuity Systems, Redwood City, Calif.) and ToppGene/ToppCluster (Cincinnati Children's Hospital Medical Center) (Chen, J. et al. *Nucleic Acids Res.* 37:W305-11 (2009); Kaimal, V. et al. *Nucleic Acids Res.* 38:W96-102 (2010)). The microarray data have been deposited into the Array Express database, found at http <colon slash slash> www <dot> ebi <dot> ac <dot> uk <slash> arrayexpress, with accession number E-MEXP-3350, in compliance with MIAME standards.
Results There were no differentially regulated genes at day 4 between the miR-223$^{+/+}$ and miR-223$^{-/-}$ cultures, indicating that progenitor cell growth under the influence of SCF and Flt-3L is not dependent on miR-223. At day 8 of the culture, 17 genes were found to be down-regulated, and 16 genes were found to be up-regulated (FIG. 23A). The full gene list appears in Table 8. Functional enrichment analysis identified the top affected biological functions to be hematological system development and function, cell growth, and regulation of immune response (FIG. 23B, FIG. 24), consistent with the earlier finding that miR-223 affects proliferative responses in eosinophils. Analysis of genes differentially regulated at day 12 of the culture (FIG. 23C) showed similar results, with 55 genes found to be down-regulated and 15 genes found to be up-regulated. Biological function analysis identified the top affected biological pathway to be hematological system development and function (FIG. 23D).

The full gene list appears in Table 9. The overlapping genes between day 8 and day 12 are listed in Table 10 and include up-regulation of Muc13, a gene with known anti-apoptotic effects (see, e.g., Sheng, Y. et al. *Gut* 60:1661-70 (2011)).

TABLE 8

List of differentially regulated genes between miR-223$^{+/+}$ and miR-223$^{-/-}$ eosinophil progenitor cultures at day 8.

| Transcript ID | Gene Symbol | Gene Description | Regulation |
|---|---|---|---|
| 10352905 | Cd34 | CD34 antigen | Up-regulated |
| 10360338 | Fcer1a | Fc receptor, IgE, high affinity I, alpha polypeptide | Up-regulated |
| 10364529 | Prtn3 | Proteinase 3 | Up-regulated |
| 10364535 | Elane | Elastase, neutrophil expressed | Up-regulated |
| 10384150 | Purb | Purine rich element binding protein B | Up-regulated |
| 10398039 | Serpina3f\|Serpina3g | Serine (or cysteine) peptidase inhibitor, clade A, member 3F\|serine (or cysteine) peptidase inhibitor, clade A, member 3G | Up-regulated |
| 10403821 | Tcrg-V3\|Tcrg-V2 | T-cell receptor gamma, variable 3\|T-cell receptor gamma, variable 2 | Up-regulated |
| 10407940 | Naip3\|Tcrg-V2\|Tcrg-V1 | NLR family, apoptosis inhibitory protein 3\|T-cell receptor gamma, variable 2\|T-cell receptor gamma, variable 1 | Up-regulated |
| 10411215 | Crhbp | Corticotropin releasing hormone binding protein | Up-regulated |
| 10419578 | Ndrg2 | N-myc downstream regulated gene 2 | Up-regulated |
| 10420261 | Ctsg | Cathepsin G | Up-regulated |
| 10427436 | C7 | Complement component 7 | Up-regulated |
| 10435288 | Muc13 | Mucin 13, epithelial transmembrane | Up-regulated |
| 10451123 | Slc29a1 | Solute carrier family 29 (nucleoside transporters), member 1 | Up-regulated |
| 10554800 | Rab38 | RAB38, member of RAS oncogene family | Up-regulated |
| 10574023 | Mt2 | Metallothionein 2 | Up-regulated |
| 10349157 | Serpinb2 | Serine (or cysteine) peptidase inhibitor, clade B, member 2 | Down-regulated |
| 10380381 | Tob1 | Transducer of ErbB-2.1 | Down-regulated |
| 10383717 | Inpp5j | Inositol polyphosphate 5-phosphatase J | Down-regulated |
| 10389022 | Myo1d | Myosin ID | Down-regulated |
| 10389025 | Myo1d | Myosin ID | Down-regulated |
| 10399691 | Id2 | Inhibitor of DNA binding 2 | Down-regulated |
| 10424683 | Ly6g | Lymphocyte antigen 6 complex, locus G | Down-regulated |
| 10439296 | Stfa2 | Stefin A2 | Down-regulated |
| 10439299 | Stfa3 | Stefin A3 | Down-regulated |
| 10475517 | AA467197\|Mir147 | Expressed sequence AA467197\|microRNA 147 | Down-regulated |
| 10493820 | S100a6 | S100 calcium binding protein A6 (calcyclin) | Down-regulated |
| 10517791 | Padi4 | Peptidyl arginine deiminase, type IV | Down-regulated |
| 10539739 | Asprv1 | Aspartic peptidase, retroviral-like 1 | Down-regulated |
| 10551696 | Rasgrp4 | RAS guanyl releasing protein 4 | Down-regulated |
| 10556302 | Ampd3 | Adenosine monophosphate deaminase 3 | Down-regulated |
| 10581538 | Nqo1 | NAD(P)H dehydrogenase, quinone 1 | Down-regulated |
| 10590628 | Ccr3 | Chemokine (C-C motif) receptor 3 | Down-regulated |

TABLE 9

List of differentially regulated genes between miR-223$^{+/+}$ and miR-223$^{-/-}$ eosinophil progenitor cultures at day 12.

| Transcript ID | Gene Symbol | Gene Description | Regulation |
|---|---|---|---|
| 10356470 | Glrp1 | Glutamine repeat protein 1 | Up-Regulated |
| 10379866 | Car4 | Carbonic anhydrase 4 | Up-Regulated |
| 10398039 | Serpina3f\|Serpina3g | Serine (or cysteine) peptidase inhibitor, clade A, member 3F\|serine (or cysteine) peptidase inhibitor, clade A, member 3G | Up-Regulated |
| 10403821 | Tcrg-V3\|Tcrg-V2 | T-cell receptor gamma, variable 3\|T-cell receptor gamma, variable 2 | Up-Regulated |
| 10407940 | Naip3\|Tcrg-V2\|Tcrg-V1 | NLR family, apoptosis inhibitory protein 3\|T-cell receptor gamma, variable 2\|T-cell receptor gamma, variable 1 | Up-Regulated |
| 10427436 | C7 | Complement component 7 | Up-Regulated |
| 10432675 | I730030J21Rik | RIKEN cDNA I730030J21 gene | Up-Regulated |
| 10435288 | Muc13 | Mucin 13, epithelial transmembrane | Up-Regulated |
| 10442762 | Prss34 | Protease, serine, 34 | Up-Regulated |
| 10444284 | H2-Ob | Histocompatibility 2, O region beta locus | Up-Regulated |
| 10506274 | Dnajc6 | DnaJ (Hsp40) homolog, subfamily C, member 6 | Up-Regulated |
| 10542120 | Clec2i | C-type lectin domain family 2, member i | Up-Regulated |
| 10566254 | Hbb-b1\|Hbb-b2 | Hemoglobin, beta adult major chain\|hemoglobin, beta adult minor chain | Up-Regulated |
| 10566258 | Hbb-b1\|Hbb-b2 | Hemoglobin, beta adult major chain\|hemoglobin, beta adult minor chain | Up-Regulated |
| 10588592 | Cacna2d2 | Calcium channel, voltage-dependent, alpha 2/delta subunit 2 | Up-Regulated |
| 10344966 | Ly96 | Lymphocyte antigen 96 | Down-regulated |

TABLE 9-continued

List of differentially regulated genes between miR-223$^{+/+}$ and miR-223$^{-/-}$ eosinophil progenitor cultures at day 12.

| Transcript ID | Gene Symbol | Gene Description | Regulation |
| --- | --- | --- | --- |
| 10353192 | Eya1 | Eyes absent 1 homolog (*Drosophila*) | Down-regulated |
| 10354374 | Slc40a1 | Solute carrier family 40 (iron-regulated transporter), member 1 | Down-regulated |
| 10354649 | Pgap1 | Post-GPI attachment to proteins 1 | Down-regulated |
| 10355456 | Mreg | Melanoregulin | Down-regulated |
| 10359161 | Soat1 | Sterol O-acyltransferase 1 | Down-regulated |
| 10360377 | AI607873 | AI607873 | Down-regulated |
| 10362511 | Gstm3 | Glutathione S-transferase, mu 3 | Down-regulated |
| 10363735 | Egr2 | Early growth response 2 | Down-regulated |
| 10365559 | Igf1 | Insulin-like growth factor 1 | Down-regulated |
| 10369413 | Sgpl1 | Sphingosine phosphate lyase 1 | Down-regulated |
| 10372988 | Slc16a7 | Solute carrier family 16 (monocarboxylic acid transporters), member 7 | Down-regulated |
| 10374248 | Abca13 | ATP-binding cassette, sub-family A (ABC1), member 13 | Down-regulated |
| 10378253 | Camkk1 | Calcium/calmodulin-dependent protein kinase kinase 1, alpha | Down-regulated |
| 10397645 | Gpr65 | G-protein coupled receptor 65 | Down-regulated |
| 10401968 | Galc | Galactosylceramidase | Down-regulated |
| 10405587 | Tgfbi | Transforming growth factor, beta induced | Down-regulated |
| 10406928 | Cd180 | CD180 antigen | Down-regulated |
| 10416251 | Egr3 | Early growth response 3 | Down-regulated |
| 10439895 | Alcam | Activated leukocyte cell adhesion molecule | Down-regulated |
| 10448278 | Mmp25 | Matrix metallopeptidase 25 | Down-regulated |
| 10458547 | Gm8615\|Gnpda1 | Glucosamine-6-phosphate deaminase 1 pseudogene | Down-regulated |
| 10467124 | Acta2 | Actin, alpha 2, smooth muscle, aorta | Down-regulated |
| 10467258 | Myof | Myoferlin | Down-regulated |
| 10469816 | Il1rn | Interleukin 1 receptor antagonist | Down-regulated |
| 10470614 | 1190002A17Rik | RIKEN cDNA 1190002A17 gene | Down-regulated |
| 10487588 | Il1a | Interleukin 1 alpha | Down-regulated |
| 10488382 | Cd93 | CD93 antigen | Down-regulated |
| 10492021 | Postn\|A630052E07Rik | Periostin, osteoblast specific factor\|RIKEN cDNA A630052E07 gene | Down-regulated |
| 10492682 | Fam198b | Family with sequence similarity 198, member B | Down-regulated |
| 10498827 | Fnip2 | Folliculin interacting protein 2 | Down-regulated |
| 10499861 | S100a9 | S100 calcium binding protein A9 (calgranulin B) | Down-regulated |
| 10501164 | Csf1 | Colony stimulating factor 1 (macrophage) | Down-regulated |
| 10501229 | Gstm1 | Glutathione S-transferase, mu 1 | Down-regulated |
| 10505517 | Tlr4 | Toll-like receptor 4 | Down-regulated |
| 10519983 | Fgl2 | Fibrinogen-like protein 2 | Down-regulated |
| 10521667 | Bst1 | Bone marrow stromal cell antigen 1 | Down-regulated |
| 10526853 | Fam20c | Family with sequence similarity 20, member C | Down-regulated |
| 10528207 | Cd36 | CD36 antigen | Down-regulated |
| 10535282 | Card11 | Caspase recruitment domain family, member 11 | Down-regulated |
| 10541599 | Clec4b2 | C-type lectin domain family 4, member b2 | Down-regulated |
| 10542355 | Emp1 | Epithelial membrane protein 1 | Down-regulated |
| 10545101 | Hpgds | Hematopoietic prostaglandin D synthase | Down-regulated |
| 10547621 | Apobec1 | Apolipoprotein B mRNA editing enzyme, catalytic polypeptide 1 | Down-regulated |
| 10547664 | Clec4e | C-type lectin domain family 4, member e | Down-regulated |
| 10560242 | C5ar1 | Complement component 5a receptor 1 | Down-regulated |
| 10562709 | Cd33 | CD33 antigen | Down-regulated |
| 10564539 | Mctp2 | Multiple C2 domains, transmembrane 2 | Down-regulated |
| 10569020 | Ifitm6 | Interferon induced transmembrane protein 6 | Down-regulated |
| 10572130 | Lpl | Lipoprotein lipase | Down-regulated |
| 10583044 | Mmp13 | Matrix metallopeptidase 13 | Down-regulated |
| 10583100 | Mmp8 | Matrix metallopeptidase 8 | Down-regulated |
| 10583112 | Mmp27 | Matrix metallopeptidase 27 | Down-regulated |
| 10601385 | Tlr13 | Toll-like receptor 13 | Down-regulated |
| 10607870 | Tlr7 | Toll-like receptor 7 | Down-regulated |

TABLE 10

List of overlapping differentially regulated genes between miR-223$^{+/+}$ and miR-223$^{-/-}$ eosinophil progenitor cultures at day 8 and day 12.

| Transcript ID | Gene Symbol | Gene Description | Regulation |
| --- | --- | --- | --- |
| 10427436 | C7 | Complement component 7 | Up-regulated |
| 10435288 | Muc13 | Mucin 13, epithelial transmembrane | Up-regulated |
| 10407940 | Naip3\|Tcrg-V2\|Tcrg-V1 | NLR family, apoptosis inhibitory protein 3\|T-cell receptor gamma, variable 2\|T-cell receptor gamma, variable 1 | Up-regulated |

TABLE 10-continued

List of overlapping differentially regulated genes between miR-223$^{+/+}$
and miR-223$^{-/-}$ eosinophil progenitor cultures at day 8 and day 12.

| Transcript ID | Gene Symbol | Gene Description | Regulation |
|---|---|---|---|
| 10403821 | Tcrg-V3\|Tcrg-V2 | T-cell receptor gamma, variable 3\|T-cell receptor gamma, variable 2 | Up-regulated |
| 10398039 | Serpina3f\|Serpina3g | Serine (or cysteine) peptidase inhibitor, clade A, member 3F\|serine (or cysteine) peptidase inhibitor, clade A, member 3G | Up-regulated |

Example 22

Expression Profiling of miRNA in IL-13-Stimulated Epithelial Cells

A study was undertaken to identify miRNAs differentially expressed in epithelial cells in response to IL-13 stimulation. MiRNA expression in IL-13-stimulated human bronchial and esophageal epithelial cells was determined using miRNA microarrays.

Human Esophageal Tissues

Patients were selected without regard to age, race, or sex. Normal patients presented to the clinic with symptoms consistent with gastroesophageal reflux disease or EE, but the endoscopic and histologic findings for these patients were normal. The active EE patients had a clinical diagnosis of EE and eosinophil counts of >24 per 400× hpf in the esophageal biopsies. The active chronic esophagitis patients had eosinophil counts of 1-15 per 400× hpf in the esophageal biopsies. Patients with systemic or swallowed topical glucocorticoid use were excluded from the selection of active EE or active chronic esophagitis patients. The EE remission patients responding to steroid treatment had a clinical history of EE, treatment with swallowed topical glucocorticoids, and responsiveness as indicated by an eosinophil count of ≤1 per 400× hpf and normalization of histological features of the disease. The EE remission patients responding to diet treatment had a clinical history of EE, treatment with diet modification, and responsiveness, as described above. The EE patients not responding to glucocorticoid treatment had a clinical history of EE, treatment with swallowed topical glucocorticoid, and non-responsiveness as indicated by an eosinophil count of ≥24 per 400× hpf.

Cell Culture

Human esophageal epithelial cells derived from human patient biopsies were cultured, as described in a previous protocol (Blanchard, C. et al. *J. Allergy Clin. Immunol.* 120:1292-300 (2007)). The human bronchial epithelial cell line HBEC was cultured as previously described (Ramirez, R. et al. *Cancer Res.* 64:9027-34 (2004)). The normal human bronchial epithelial cells (Lonza, Basel, Switzerland) were cultured, as described in a previous protocol (Kariyawasam, H. et al. *J. Allergy Clin. Immunol.* 124:454-462 (2009)). The U937 monocytes and Jurkat T cells were cultured in RPMI 1640 medium (Fisher Scientific) supplemented with 0.10% FBS, 100 U/mL penicillin, and 100 µg/ml streptomycin. The CCD-16Lu fibroblasts were cultured in Eagle's Minimum Essential Medium (ATCC, Manassas, Va.) supplemented with 10% FBS, 100 U/mL penicillin, and 100 µg/ml streptomycin.

RNA Extraction and miRNA Microarray Analysis

Human esophageal epithelial cells and bronchial epithelial cells were stimulated with media or 100 ng/mL IL-13 for 24 hours. Total RNA, including miRNA, was isolated using the miRNeasy Mini Kit (Qiagen), according to the manufacturer's instructions. RNA quality was assessed using the 2100 bioanalyzer (Agilent Technologies), and only samples with RNA integrity number >8 were used. MiRNA expression from human bronchial epithelial cells was profiled using the TaqMan Human MicroRNA Array v1.0 (Applied Biosystems), which includes probes for 365 human miRNAs, according to the manufacturer's protocols. Data analysis was carried out using GeneSpring software (Agilent Technologies).

The miRNAs differentially regulated between unstimulated and IL-13 stimulated samples were identified by normalizing the expression data to the average of two endogenous control probes, namely RNU44 and RNU48, then filtered on cycle threshold values <35 and at least a 2-fold change between unstimulated and IL-13-stimulated samples. Statistical significance was determined at $p<0.05$ with Benjamini Hochberg false discovery rate correction. The list of differentially expressed miRNAs was clustered using hierarchical clustering, and a heatmap was generated. A similar analysis was carried out comparing unstimulated and IL-13-stimulated human esophageal epithelial cells, except the TaqMan Human MicroRNA Array v2.0 (Applied Biosystems) was used, which includes probes for 667 human miRNAs. The microarray data have been deposited into the Array Express database, found at http <colon slash slash> www <dot> ebi <dot> ac <dot> uk <slash> arrayexpress, with accession numbers E-MEXP-3351 and E-MEXP-3353, in compliance with MIAME standards.

qRT-PCR for miRNA

Levels of miRNA expression were measured quantitatively by using the TaqMan MicroRNA Assays (Applied Biosystems), following the manufacturer's protocol. The expression levels were normalized to the U6 endogenous control. Relative expression was calculated as previously described (Lu, T. et al. *J. Immunol.* 182:4994-5002 (2009)).

Statistical Analysis

A Student's t-test was used to determine the significance between two groups. One-way ANOVA with a Tukey post-hoc test was used to determine the significance between more than 2 groups. Statistical significance and the p values were indicated on the figures where appropriate. P values less than 0.05 were considered statistically significant.

Results

Comparing IL-13-treated and untreated esophageal epithelial cells, 6 miRNAs were found to be differentially regulated in response to IL-13 (FIG. 25A). These include four down-regulated miRNAs, namely miR-375, miR-212, miR-181a-2* (the asterisk indicates the minor form of the miRNA derived from the passenger strand), and miR-145, and 2 up-regulated miRNAs, namely miR-223 and miR-137. A similar analysis of IL-13 treated human bronchial epithelial cells found four downregulated miRNAs, namely miR-565, miR-7, miR-335, and miR-375, and 2 up-regulated miRNAs, namely miR-146b and miR-203 (FIG. 25B).

Figure 26A:
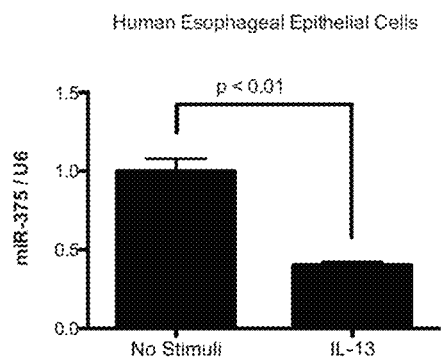
FIGS. 26A-D depict qRT-PCR verification of miR-375 expression in IL-13-stimulated human esophageal epithelial cells and human bronchial epithelial cells. Expression of miR-375 was determined in (FIG. 26A) IL-13-stimulated human esophageal epithelial cells compared to controls and (FIG. 26B) IL-13-stimulated human bronchial epithelial cells compared to controls.
Figure 26B:
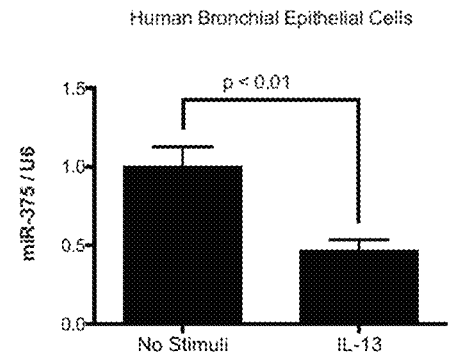
Figure 26C:
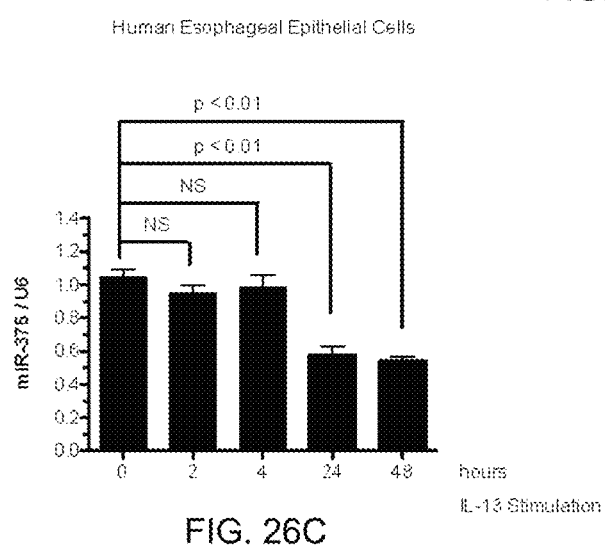
Figure 26D:
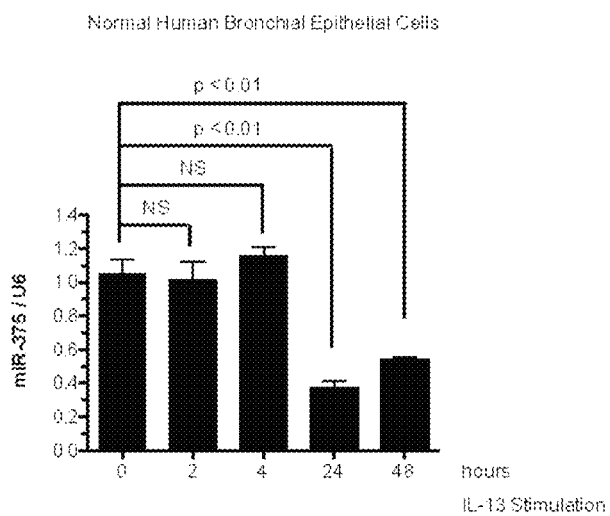
Figure 27:
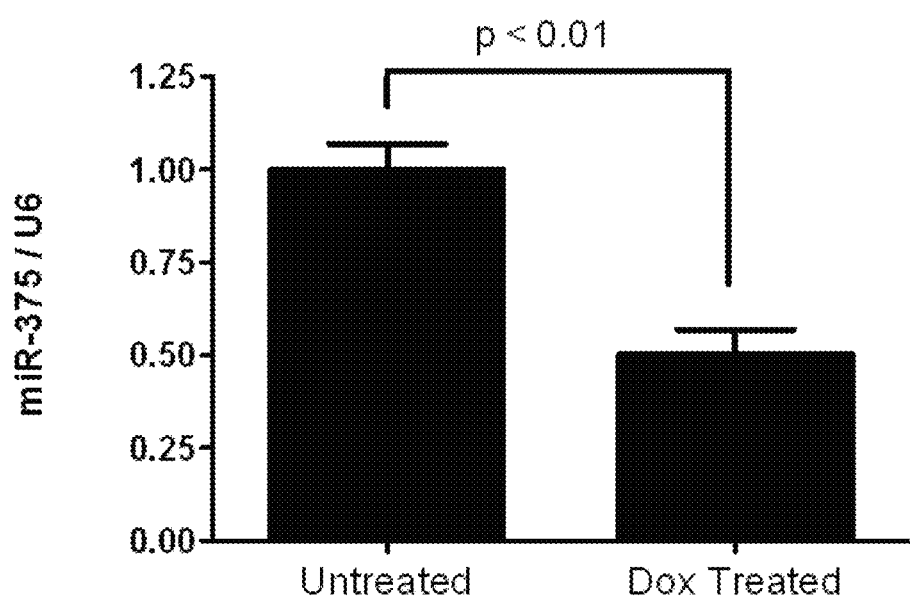
FIG. 27 depicts expression of miR-375 in a doxycycline-induced IL-13 lung transgenic experimental asthma model. The relative expression levels of miR-375 were determined by qPCR normalized to U6. N=6 mice per group; data are represented as mean±SEM.

The only miRNA that was differentially regulated in both epithelial cell types after IL-13 treatment was miR-375. This observed miR-375 down-regulation was subsequently validated in both the human esophageal and human bronchial epithelial cells after IL-13 stimulation by qPCR (FIGS. 26A-B). Kinetic analyses of miR-375 expression in human esophageal epithelial cells (FIG. 26C) and in normal human bronchial epithelial cells (FIG. 26D) indicated that miR-375 was down-regulated after 24 and 48 hours of IL-13 stimulation.

Example 23

Expression of MiR-375 in IL-13 Lung Transgenic Mice and EE Patients

A subsequent study was undertaken to determine the long-term effect of IL-13 exposure on miR-375 expression. The same study also aimed to determine whether miR-375 was also down-regulated in EE patients, since EE has been reported to be a $T_H2$ associated disease with IL-13 having a major role in its pathogenesis (see, e.g., Blanchard, C. and Rothenberg, M. *Gastointest. Endosc. Clin. N. Am.* 18:133-43 (2008); Mulder, D. and Justinich, C. *Mucosal. Immunol.* 4:139-47 (2011)). The study also aimed to determine whether the expression levels of miR-375 were normalized in EE patients in remission.

Experimental Asthma Induction in IL-13 Bitransgenic Mice

Bitransgenic mice bearing CCSP-rtTA and (tetO)$_7$CMV-IL-13 transgenes have been previously described (Lu, T. et al. *J. Immunol.* 182:4994-5002 (2009)). Experimental asthma was induced in IL-13 bitransgenic mice by feeding bi-transgenic mice doxycycline-impregnated food for 4 weeks, as described in a previous protocol (Wan et al., *Development*, 131:953-64 (2004)). All animals were housed under specific pathogen-free conditions in accordance with institutional guidelines. The use of animals in these experiments was approved by the Institutional Animal Care and Use Committee of the Cincinnati Children's Hospital Medical Center.

qRT-PCR for mRNA

Total RNA was reverse transcribed using the High Capacity cDNA Reverse Transcription kit (Applied Biosystems). All primer/probe sets were obtained from Applied. Biosytems. Samples were analyzed by the TaqMan qRT-PCR (Applied Biosystems) for CPA3 (Assay ID: Hs00157019_m1) and normalized to HPRT1 (Assay ID: Hs01003267_m1). Relative expression was calculated as previously described (Lu, T. et al. *J. Immunol.* 187:3362-71 (2011).

Results

An IL-13 lung transgenic mouse model was utilized, wherein experimental asthma was induced by 4 weeks of doxycycline-induced IL-13 transgene expression. Compared to control mice that received no doxycycline, doxycycline-treated IL-13 transgenic mice have significant down-regulation of miR-375 in the asthmatic lungs (FIG. 26).

Compared to normal healthy controls, EE patients had significant down-regulation of miR-375 in esophageal tissue. This down-regulation was not evident in patients with chronic (non-eosinophilic) esophagitis (FIG. 28A), which has a distinct etiology and pathogenesis from EE (see, e.g., Blanchard, C. et al. *J. Clin. Invest.* 116:536-47 (2006)).

Figure 28A:
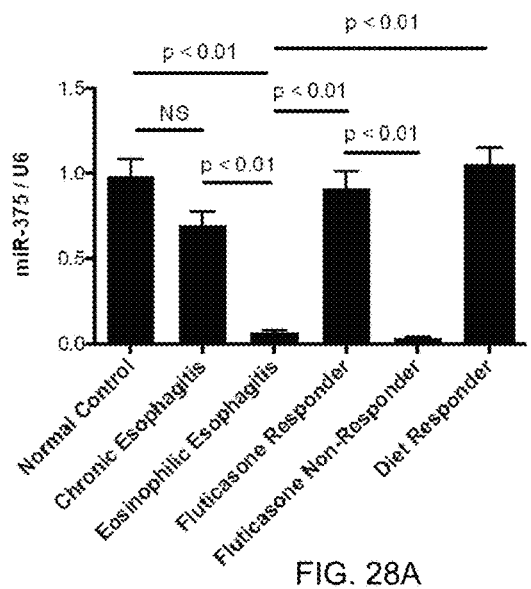
FIGS. 28A-C depict expression of miR-375 in esophageal biopsies from EE patients and the correlation with esophageal eosinophil counts and EE signature genes.

EE patients that responded to either fluticasonc propionate therapy or diet modification had miR-375 levels comparable to normal healthy controls. Patients that did not respond to therapy continued to have repressed miR-375 levels (FIG. 28A).

Since miR-375 down-regulation fluctuated with disease activity, the study subsequently aimed to investigate the correlation of miR-375 expression with other markers of EE disease activity. For example, the study aimed to determine miR-375 correlation with the high level of eosinophil infiltration observed in the esophageal biopsies of EE patients (see, e.g., Blanchard, C. et al. *J. Clin. Invest.* 116:536-47 (2006); Abonia, J. et al. *J. Allergy Clin. Immunol.* 126:140-9 (2010)) and the expression of previously identified EE signature genes.

Figure 28B:
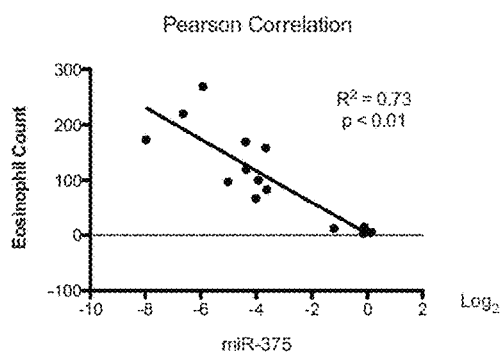
Figure 28C:
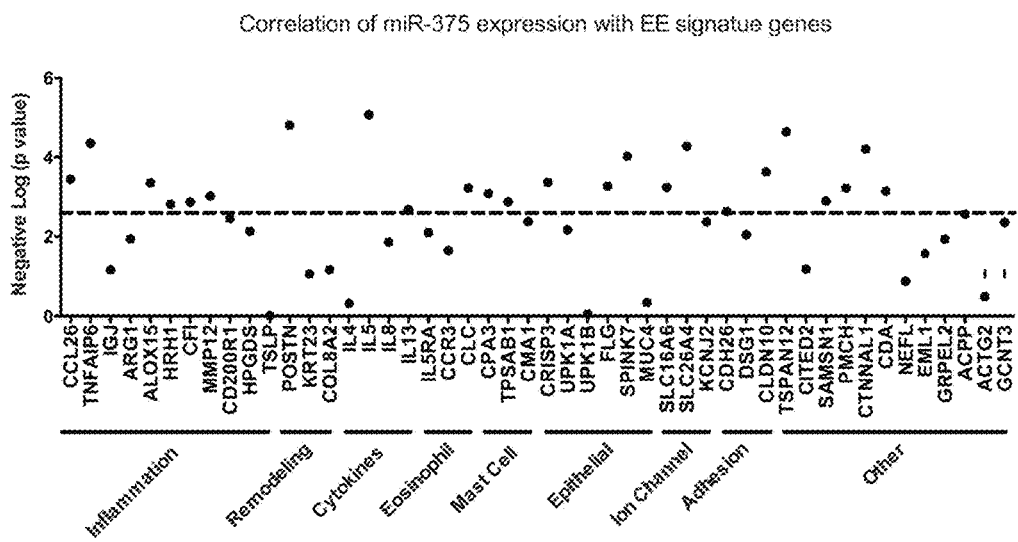

Esophageal miR-375 expression exhibited a significant inverse correlation with the level of eosinophil infiltration in esophageal biopsies as well as esophageal expression of genes involved in inflammation, including CCL26 (eotaxin-3) (Blanchard, C. et al. *J. Clin. Invest.* 116:536-47 (2006)), and remodeling, including POSTN (periostin) (Stansfield, W. et al. *Ann. Thorac. Surg.* 88:1916-21 (2009)). Esophageal miR-375 expression also exhibited a significant inverse correlation with the level of esophageal expression of $T_H2$ cytokines, including IL-5 and IL-13 (Kaiko, G. and Foster, P. *Curr. Opin. Allergy Clin. Immunol.* 11:39-45 (2011)) and cell-specific markers for eosinophils (CLC) (Ackerman, S. et al. *J. Biol. Chem.* 277:14859-68 (2002)), mast cells (CPA3 and TPSAB1) (Xing, W. et al. *Proc. Natl. Acad. Sci. U.S.A.* 108:14210-5 (2011)), and epithelial cells (FLG) (Blanchard, C. et al. *J. Immunol.* 184:4033-41 (2010)) (FIGS. 28B-C).

Example 24

Predominent Expression of MiR-375 in Epithelial Cells

A subsequent study was undertaken to determine the levels of miR-375 expression in different cell types. Expression levels were measured via qPCR analysis of miR-375 levels in esophageal epithelial cells, normal bronchial epithelial cells, normal smooth muscle cells, neutrophils, eosinophils, monocytes, fibroblasts and T-cells.

Figure 29:
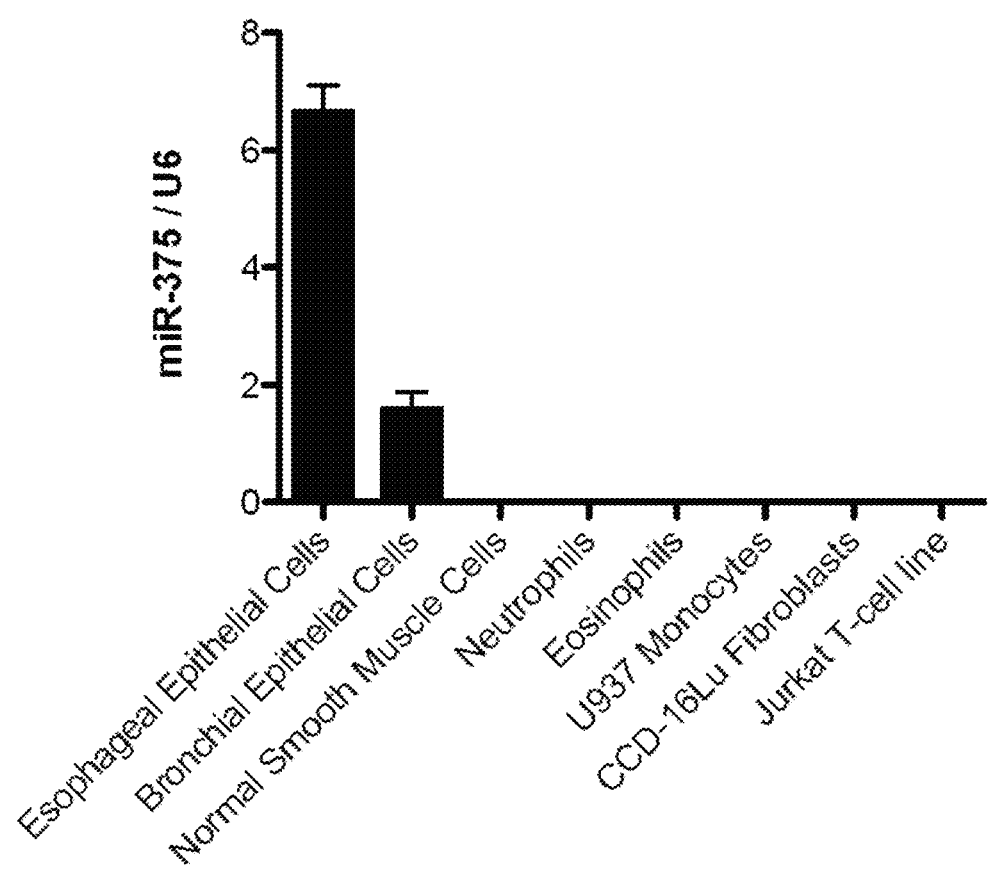
FIG. 29 depicts miR-375 expression levels in different cell types. The relative expression level of miR-375 in different cell types was determined by qPCR normalized to U6. N=3 per group; data are represented as mean±SEM.

The esophageal epithelial cells were found to have the highest miR-375 expression (FIG. 29). Therefore, subsequent studies were focused on the role of miR-375 in the epithelial cells.

Example 25

MiR-375 Regulated IL-13-Regulated Signature Genes

A subsequent study was undertaken to determine the relationship between miR-375 and the expression of IL-13-regulated signature genes. Using a lentiviral vector, miR-375 was over-expressed in the esophageal epithelial cell line TE-7. The control-transduced and miR-375-transduced TE-7 cells were then treated with IL-13 to determine the effect of miR-375 on IL-13 induced-esophageal epithelial transcriptome.

Lentiviral Transduction

Cells from the human esophageal epithelial cell line TE-7 were transduced with pmiRNA1-pre-miR-375 vector or pmiRNA1-Control vector (System Biosciences, Mountain View, Calif.). The vectors included GFP and puromycin resistance genes as selection markers. Three days after transduction, cells were selected by FACS sorting for GFP+ cells and further cultured in media containing 4 µg/mL puromycin for 1 week. The cells were >99% GFP+ after selection.

Human Genome-Wide mRNA Microarray

The human Gene 1.0ST array (Affymetrix) was used to compare the gene expression profiles of control-transduced TE-7 cells and pre-miR-375-transduced TE-7 cells before and after IL-13 treatment. Microarray data were analyzed using GeneSpring software (Agilent Technologies, San Diego, Calif.), as described in a previous protocol (Lu, T. et al. J. Immunol. 187:3362-73 (2011)).

Global scaling was performed to compare genes from chip to chip, and a base set of probes was generated by requiring a minimum raw expression level of the 20th percentile out of all probes on the microarray. The resulting probe sets were then baseline transformed and filtered on at least a 1.2-fold difference between control-transduced and pre-miR-375-transduced cells with or without IL-13 treatment to identify miR-375 regulated genes. Statistical significance was determined at p<0.05 with Benjamini Hochberg false discovery rate correction. The resulting list of genes was clustered using hierarchical clustering, and a heatmap was generated. Biological functional enrichment analysis was carried out using Ingenuity Pathway Analysis (Ingenuity Systems) and Toppgene/Toppcluster (Cincinnati Children's Hospital Medical Center) (Chen, J. et al. Nucleic Acids Res. 37:W305-11 (2009); Kaimal, V. et al. Nucleic Acids Res. 38:W96-102 (2010)). The microarray data have been deposited into the Array Express database, found at http <colon slash slash> www <dot> ebi <dot> ac <dot> uk <slash> arrayexpress, with accession number E-MEXP-3345, in compliance with MIAME standards.

Correlation of MiR-375 with Major EE Signature Genes

Esophageal mRNA from EE patients was reverse transcribed using the High Capacity cDNA Reverse Transcription Kit (Applied Biosystems), following the manufacturer's protocol, using the TaqMan reagents (Applied Biosystems) for amplification of EE signature genes (Blanchard, C. et al. J. Allergy Clin. Immunol. 120:1292-300 (2007); Blanchard, C. and Rothenberg, M. Gastrointest. Endosc. Clin. N. Am. 18:133-43 (2008); Abonia, J. et al. J. Allergy Clin. Immunol. 126:140-9 (20.10)). Real-time PCR amplification was performed on a TaqMan 7900HT Real-Time PCR System (Applied Biosystems).

The expression correlation study between miR-375 and the 48 EE genes was performed on GraphPad Prism (GraphPad Software). Negative log of p values from Pearson correlation analysis were plotted to demonstrate correlation significance with EE genes. To control for the increased risk of false positives due to the number of statistical tests performed, a Bonferroni correction was applied based on the number of gene expression profiles compared. Because the average pairwise correlation between gene expression profiles was 0.54, a principal components analysis was applied to determine the effective number of independent comparisons, as described in a previous protocol (Chen, J. et al. Nucleic Acids Res. 27:W305-11 (2009)). Using this approach, a p-value of 0.002 was required to achieve a family-wise error rate of 0.05.

Results

Figure 30A:
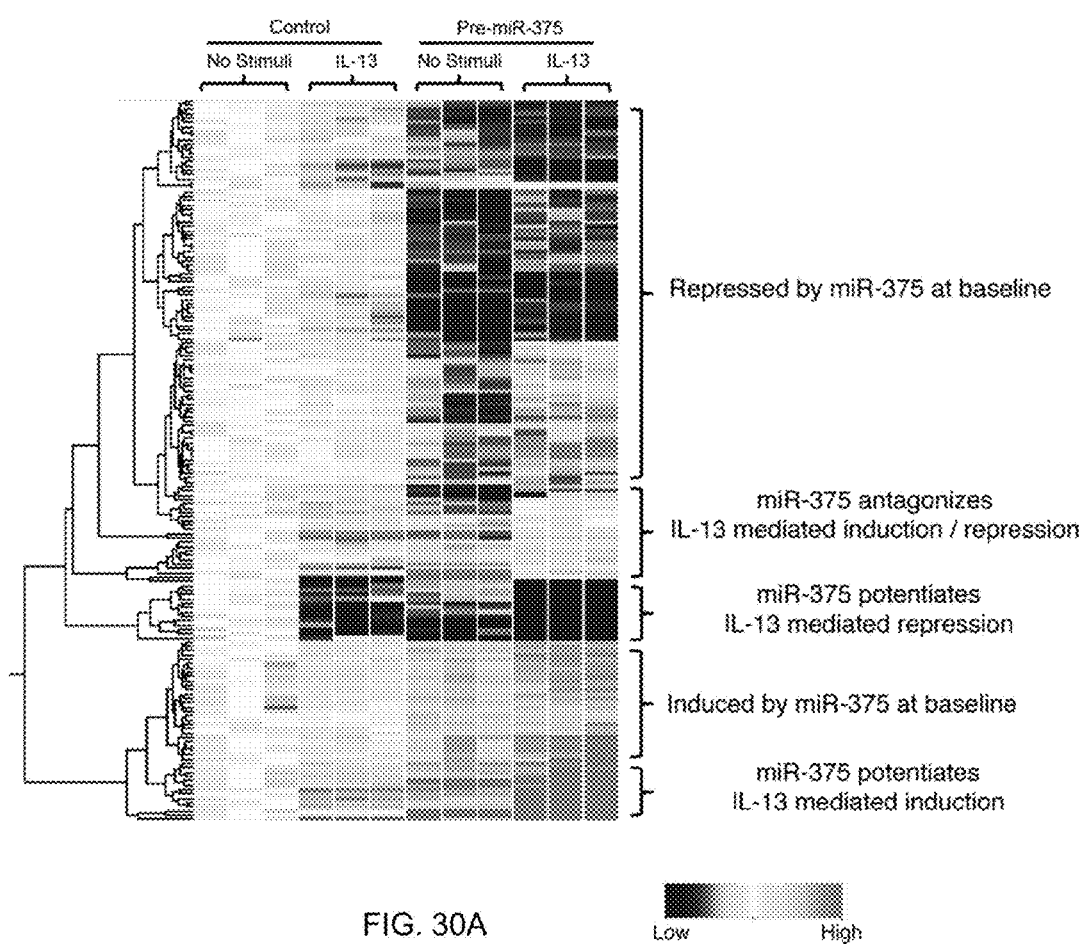
FIGS. 30A-B depict genes differentially regulated by miR-375 in esophageal epithelial cells before and after IL-13 stimulation.

MiR-375 was able to repress a large set of genes at baseline, consistent with the function of miRNAs as repressors of gene expression (FIG. 29A). A smaller set of genes were induced at baseline; this can be though miR-375 mediated repression of transcriptional repressors (FIG. 30A). MiR-375 was able to both potentiate and antagonize a subset of IL-13 mediated gene signatures, indicating a complex interaction between miR-375 and effects of IL-13 (FIG. 30A).

Figure 30B:
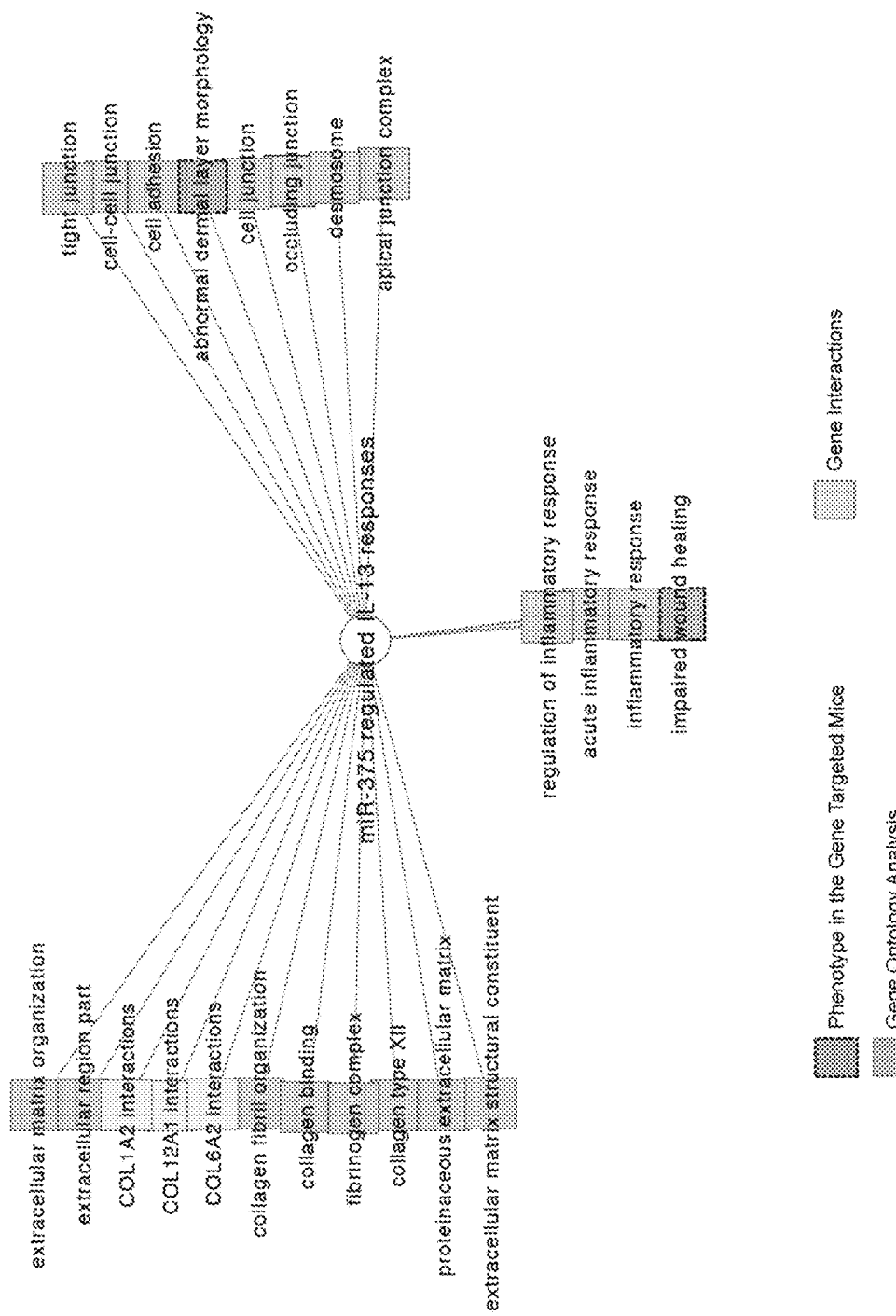

Functional analysis indicated that the pathways affected by miR-375 under IL-13-stimulated conditions were enriched for processes involved in extracellular matrix organization, cellular junctions, and inflammation (FIG. 30B). The differentially regulated genes are listed in Table 11.

Figure 31:
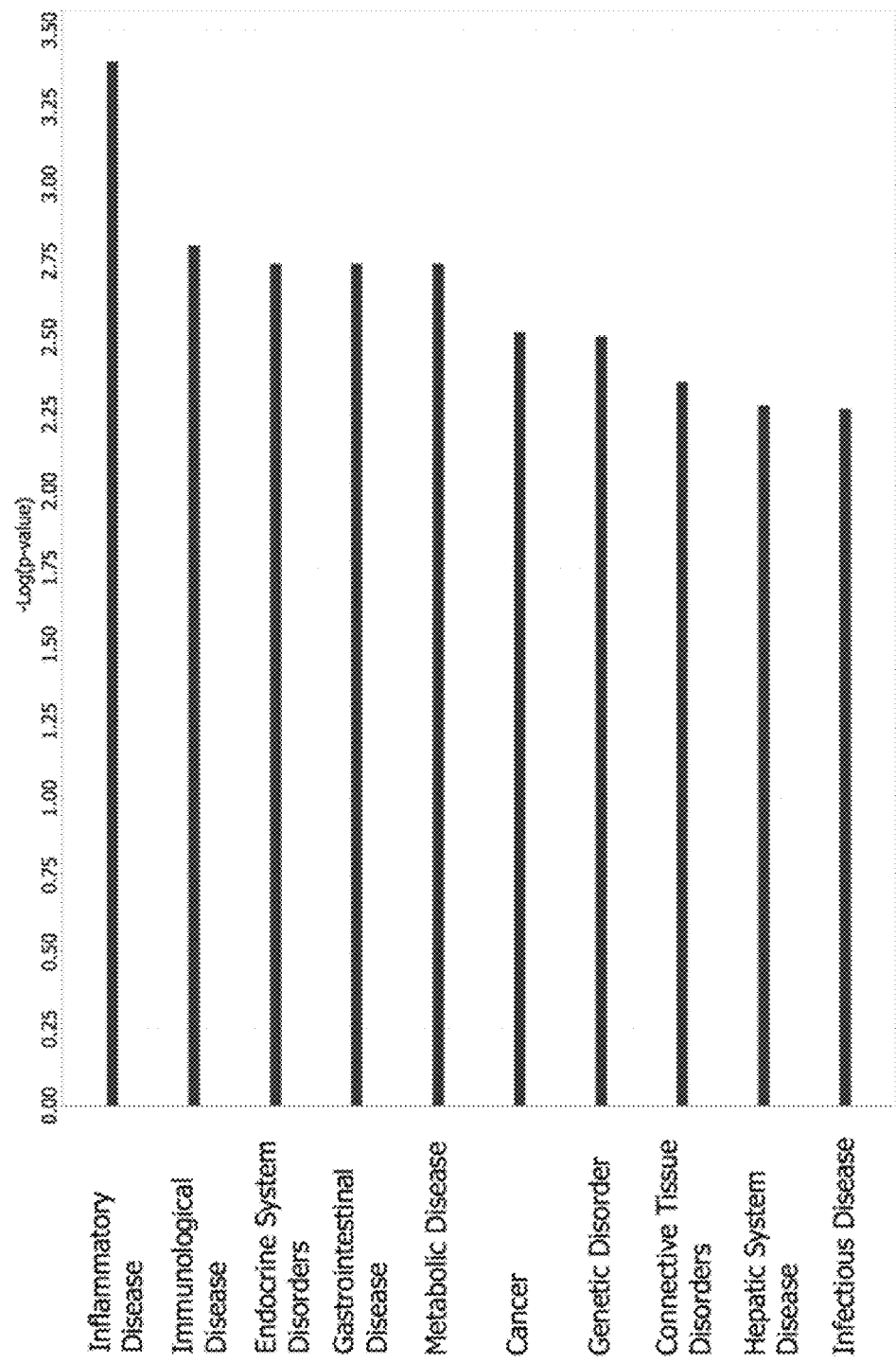
FIG. 31 depicts a biological function enrichment analysis of all miR-375-regulated genes. The figure illustrates an analysis of the most significant diseases and disorders represented by all genes differentially regulated by miR-375.

Analysis of all miR-375-regulated genes indicated that inflammatory diseases and immunological diseases are the two most significantly over-represented disease states (FIG. 31). The miR-375-regulated genes in each of these disease processes are listed in Table 12.

TABLE 11

List of genes differentially regulated by miR-375 in esophageal epithelial cells before and after IL-13 stimulation.

| Transcript ID | Gene Symbol | Gene Description | Regulation |
|---|---|---|---|
| 7900129 | C1orf113\|FAM176B | Chromosome 1 open reading frame 113\|family with sequence similarity 176, member B | Repressed by miR-375 at baseline |
| 7905339 | GABPB2 | GA binding protein transcription factor, beta subunit 2 | Repressed by miR-375 at baseline |
| 7907531 | GPR52 | G protein-coupled receptor 52 | Repressed by miR-375 at baseline |
| 7910379 | DUSP5P | Dual specificity phosphatase 5 pseudogene | Repressed by miR-375 at baseline |
| 7914322 | SNORD103A\|SNORD103B | Small nucleolar RNA, C/D box 103A\|small nucleolar RNA, C/D box 103B | Repressed by miR-375 at baseline |
| 7914324 | SNORD103A\|SNORD103B | Small nucleolar RNA, C/D box 103A\|small nucleolar RNA, C/D box 103B | Repressed by miR-375 at baseline |
| 7920664 | THBS3 | Thrombospondin 3 | Repressed by miR-375 at baseline |
| 7920852 | KIAA0907 | KIAA0907 | Repressed by miR-375 at baseline |
| 7934278 | P4HA1 | Prolyl 4-hydroxylase, alpha polypeptide I | Repressed by miR-375 at baseline |
| 7942332 | FOLR1 | Folate receptor 1 (adult) | Repressed by miR-375 at baseline |
| 7944867 | SIAE | Sialic acid acetylesterase | Repressed by miR-375 at baseline |
| 7951297 | MMP12 | Matrix metallopeptidase 12 (macrophage elastase) | Repressed by miR-375 at baseline |

TABLE 11-continued

List of genes differentially regulated by miR-375 in esophageal epithelial cells before and after IL-13 stimulation.

| Transcript ID | Gene Symbol | Gene Description | Regulation |
|---|---|---|---|
| 7954208 | PIK3C2G | Phosphoinositide-3-kinase, class 2, gamma polypeptide | Repressed by miR-375 at baseline |
| 7956038 | MMP19\|LOC440104 | Matrix metallopeptidase 19\|hypothetical LOC440104 | Repressed by miR-375 at baseline |
| 7956876 | LLPH | LLP homolog, long-term synaptic facilitation (*Aplysia*) | Repressed by miR-375 at baseline |
| 7963261 | LOC494150 | Prohibitin pseudogene | Repressed by miR-375 at baseline |
| 7964119 | STAT2 | Signal transducer and activator of transcription 2, 113 kDa | Repressed by miR-375 at baseline |
| 7967210 | LOC338799 | LOC338799 | Repressed by miR-375 at baseline |
| 7971461 | LCP1 | Lymphocyte cytosolic protein 1 (L-plastin) | Repressed by miR-375 at baseline |
| 7978718 | SEC23A | Sec23 homotog A (*S. cerevisiae*) | Repressed by miR-375 at baseline |
| 7994582 | SULT1A3\|GIYD1\|GIYD2\|SULT1A2\|SULT1A4 | Sulfotransferase family, cytosolic, 1A, phenol-preferring, member 3\|GIY-YIG domain containing 1\|GIY-YIG domain containing 2\|sulfotransferase family, cytosolic, 1A, phenol-preferring, member 2\|sulfotransferase family, cytosolic, 1 A, phenol-preferring, member 4 | Repressed by miR-375 at baseline |
| 7994781 | SULT1A3\|G1YD1\|GIYD2\|SULT1A2\|SULT1A4 | Sulfotransferase family, cytosolic, 1A, phenol-preferring, member 3\|G1Y-YIG domain containing 1\|GIY-YIG domain containing 2\|sulfotransferase family, cytosolic, 1A, phenol-preferring, member 2\|sulfotransferase family, cytosolic, 1 A, phenol-preferring, member 4 | Repressed by miR-375 at baseline |
| 7996430 | HSF4IFBXL8 | Heat shock transcription factor 4 I F-box and leucine rich repeat protein 8 | Repressed by miR-375 at baseline |
| 7998664 | SNORA10 | Small nucleolar RNA, H/ACA box 10 | Repressed by miR-375 at baseline |
| 8000757 | DOC2A\|INO80E | Double C2-like domains, alpha\|INO80 complex subunit E | Repressed by miR-375 at baseline |
| 8000799 | GDPD3 | Glycerophosphodiester phosphodiesterase domain containing 3 | Repressed by miR-375 at baseline |
| 8013364 | SLC47A2 | Solute carrier family 47, member 2 | Repressed by miR-375 at baseline |
| 8013622 | SGK494\|FLJ25006 | Uncharacterized serine/threonine-protein kinase SgK494 | Repressed by miR-375 at baseline |
| 8014903 | GSDMB | Gasdermin B | Repressed by miR-375 at baseline |
| 8016259 | LRRC37A2\|LRRC37A3\|LOC100294335 | Leucine rich repeat containing 37, member A2\|leucine rich repeat containing 37A\|leucine rich repeat containing 37, member A3\|similar to cl14 SLIT-like testicular protein | Repressed by miR-375 at baseline |
| 8031176 | LENG8 | Leukocyte receptor cluster (LRC) member 8 | Repressed by miR-375 at baseline |
| 8032249 | ADAMTSL5 | ADAMTS-like 5 | Repressed by miR-375 at baseline |
| 8033257 | C3 | Complement component 3 | Repressed by miR-375 at baseline |
| 8041204 | SNORA10 | Small nucleolar RNA, H/ACA box 10 | Repressed by miR-375 at baseline |
| 8044605 | LOC654433 | LOC654433 | Repressed by miR-375 at baseline |
| 8045539 | KYNU | Kynureninase (L-kynurenine hydrolase) | Repressed by miR-375 at baseline |
| 8046906 | GULP1 | GULP, engulfment adaptor PTB domain containing 1 | Repressed by miR-375 at baseline |
| 8048381 | STK36 | Serine/threonine kinase 36, fused homotog (*Drosophila*) | Repressed by miR-375 at baseline |
| 8053200 | DQX1 | DEAQ box RNA-dependent ATPase 1 | Repressed by miR-375 at baseline |
| 8056151 | PLA2R1 | Phospholipase A2 receptor 1, 180 kDa | Repressed by miR-375 at baseline |
| 8066786 | ZMYND8 | Zinc finger, MYND-type containing 8 | Repressed by miR-375 at baseline |
| 8066822 | SULF2 | Sulfatase 2 | Repressed by miR-375 at baseline |
| 8074577 | PI4KAP2\|PI4KAP1 | Phosphatidylinositol 4-kinase, catalytic, alpha pseudogene 2\|phosphatidylinositol 4-kinase, catalytic, alpha pseudogene 1 | Repressed by miR-375 at baseline |
| 8085716 | SATB1 | SATB homeobox 1 | Repressed by miR-375 at baseline |
| 8086627 | ALS2CL | ALS2 C-terminal like | Repressed by miR-375 at baseline |
| 8087433 | NICN1\|AMT | Nicolin 1\|aminomethyltransferase | Repressed by miR-375 at baseline |

TABLE 11-continued

List of genes differentially regulated by miR-375 in esophageal epithelial cells before and after IL-13 stimulation.

| Transcript ID | Gene Symbol | Gene Description | Regulation |
|---|---|---|---|
| 8092978 | MUC4 | Mucin 4, cell surface associated | Repressed by miR-375 at baseline |
| 8098441 | ODZ3 | Odz, odd Oz/ten-m homolog 3 (*Drosophila*) | Repressed by miR-375 at baseline |
| 8102792 | PCDH18 | Protocadherin 18 | Repressed by miR-375 at baseline |
| 8103853 | MGC45800 | Hypothetical LOC90768 | Repressed by miR-375 at baseline |
| 8105077 | CARD6 | Caspase recruitment domain family, member 6 | Repressed by miR-375 at baseline |
| 8109086 | ADRB2 | Adrenergic, beta-2-, receptor, surface | Repressed by miR-375 at baseline |
| 8116921 | EDN1 | Endothelin 1 | Repressed by miR-375 at baseline |
| 8117714 | OR2J3\|OR2J1 | Olfactory receptor, family 2, subfamily J, member 3\|olfactory receptor, family 2, subfamily J, member 1 | Repressed by miR-375 at baseline |
| 8124654 | GABBR1 | Gamma-aminobutyric acid (GABA) B receptor, 1 | Repressed by miR-375 at baseline |
| 8124691 | HCG8 | HLA complex group 8 | Repressed by miR-375 at baseline |
| 8125687 | RGL2 | Ral guanine nucleotide dissociation stimulator-like 2 | Repressed by miR-375 at baseline |
| 8126018 | STK38 | Serine/threonine kinase 38 | Repressed by miR-375 at baseline |
| 8126428 | TRERF1 | Transcriptional regulating factor 1 | Repressed by miR-375 at baseline |
| 8133633 | NSUN5P2\|NSUN5P1\|NSUN5B\|NSUN5C\|TRIM73 | NOP2/Sun domain family, member 5 pseudogene 2\|NOP2/Sun domain family, member 5 pseudogene 1\|NOL1/NOP2/Sun domain family, member 5B\|NOL1/NOP2/Sun domain family, member 5\|NOL1/NOP2/Sun domain family, member 5C\|tripartite motif-containing 73 | Repressed by miR-375 at baseline |
| 8140386 | STYXL1 | Serine/threonine/tyrosine interacting-like 1 | Repressed by miR-375 at baseline |
| 8148149 | ZHX2 | Zinc fingers and homeoboxes 2 | Repressed by miR-375 at baseline |
| 8153550 | NRBP2 | Nuclear receptor binding protein 2 | Repressed by miR-375 at baseline |
| 8156060 | TLE4 | Transducin-like enhancer of split 4 (E(sp1) homolog, *Drosophila*) | Repressed by miR-375 at baseline |
| 8157800 | MIR181A2 | MicroRNA 181 a-2 | Repressed by miR-375 at baseline |
| 8158662 | SNORD62A\|SNORD62B | Small nucleolar RNA, C/D box 62A\|small nucleolar RNA, C/D box 62B | Repressed by miR-375 at baseline |
| 8158864 | SNORD62A\|SNORD62B | Small nucleolar RNA, C/D box 62A\|small nucleolar RNA, C/D box 62B | Repressed by miR-375 at baseline |
| 8161373 | LOC100289528 | LOC100289528 | Repressed by miR-375 at baseline |
| 8161554 | LOC100289528 | LOC100289528 | Repressed by miR-375 at baseline |
| 8170921 | PLXNA3 | Plexin A3 | Repressed by miR-375 at baseline |
| 8175666 | GABRE | Gamma-aminobutyric acid (GABA) A receptor, epsilon | Repressed by miR-375 at baseline |
| 8177694 | OR2J3\|OR2J1 | Olfactory receptor, family 2, subfamily J, member 3\|olfactory receptor, family 2, subfamily J, member 1 | Repressed by miR-375 at baseline |
| 8178298 | GABBR1 | Gamma-aminobutyric acid (GABA) B receptor, 1 | Repressed by miR-375 at baseline |
| 8178955 | RGL2 | Ral guanine nucleotide dissociation stimulator-like 2 | Repressed by miR-375 at baseline |
| 8179003 | OR2J3\|OR2J1 | Olfactory receptor, family 2, subfamily J, member 3\|olfactory receptor, family 2, subfamily J, member 1 | Repressed by miR-375 at baseline |
| 8179595 | GABBR1 | Gamma-aminobutyric acid (GABA) B receptor, 1 | Repressed by miR-375 at baseline |
| 8180144 | RGL2 | Ral guanine nucleotide dissociation stimulator-like 2 | Repressed by miR-375 at baseline |
| 7904364 | WDR3 | WD repeat domain 3 | Induced by miR-375 at baseline |
| 7916219 | C1orf163 | Chromosome 1 open reading frame 163 | Induced by miR-375 at baseline |
| 7927267 | FAM35B\|FAM35B2\|FAM35A | Family with sequence similarity 35, member B\|family with sequence similarity 35, member B2\|family with sequence similarity 35, member A | Induced by miR-375 at baseline |
| 7927288 | FAM35B2\|FAM35A | Family with sequence similarity 35, member B2\|family with sequence similarity 35, member B\|family with sequence similarity 35, member A | Induced by miR-375 at baseline |

TABLE 11-continued

List of genes differentially regulated by miR-375 in esophageal epithelial cells before and after IL-13 stimulation.

| Transcript ID | Gene Symbol | Gene Description | Regulation |
|---|---|---|---|
| 7929072 | IFIT5 | Interferon-induced protein with tetratricopeptide repeats 5 | Induced by miR-375 at baseline |
| 7932765 | MPP7 | Membrane protein, palmitoylated 7 (MAGUK p55 subfamily member 7) | Induced by miR-375 at baseline |
| 7935707 | CHUK | Conserved helix-loop-helix ubiquitous kinase | Induced by miR-375 at baseline |
| 7944656 | SC5DL | Sterol-C5-desaturase (ERG3 delta-5-desaturase homolog, S. cerevisiae)-like | Induced by miR-375 at baseline |
| 7945169 | TMEM45B | Transmembrane protein 45B | Induced by miR-375 at baseline |
| 7948908 | SNORD26\|SNHG1 | Small nucleolar RNA, C/D box 26\|small nucleolar RNA host gene 1 (non-protein coding) | Induced by miR-375 at baseline |
| 8059026 | MIR375 | MicroRNA 375 | Induced by miR-375 at baseline |
| 7951036 | SNORD5\|TAF1D | Small nucleolar RNA, C/D box 5\|TATA box binding protein (TBP)-associated factor, RNA polymerase I, D, 41 kDa | Induced by miR-375 at baseline |
| 7981964 | SNORD116-8\|SNORD116-3\|SNORD116-9 | Small nucleolar RNA, C/D box 116-8\|small nucleolar RNA, C/D box 116-3\|small nucleolar RNA, C/D box 116-9 | Induced by miR-375 at baseline |
| 7981976 | SNORD116-14 | Small nucleolar RNA, C/D box 116-14 | Induced by miR-375 at baseline |
| 7981978 | SNORD116-15 | Small nucleolar RNA, C/D box 116-15 | Induced by miR-375 at baseline |
| 7981982 | SNORD116-17\|SNORD116-19\|SNORD116-15\|SNORD116-16\|SNORD116-18\|SNORD116-21\|SNORD116-22\|SNORD116-14\|SNORD116-20\|SNORD116@\|SN RPN | Small nucleolar RNA, C/D box 116-17\|small nucleolar RNA, C/D box 116-19\|small nucleolar RNA, C/D box 116-15\|small nucleolar RNA, C/D box 116-16\|small nucleolar RNA, C/D box 116-18\|small nucleolar RNA, C/D box 116-21\|small nucleolar RNA, C/D box 116-22\|small nucleolar RNA, C/D box 116-14\|small nucleolar RNA, C/D box 116-20\|small nucleolar RNA, C/D box 116 cluster\|small nuclear ribonucleoprotein polypeptide N | Induced by miR-375 at baseline |
| 7981986 | SNORD116-17\|SNORD116-19\|SNORD116-15\|SNORD116-16\|SNORD116-18\|SNORD116-21\|SNORD116-22\|SNORD116-14\|SNORD116-20\|SNORD116@\|SN RPN | Small nucleolar RNA, C/D box 116-17\|small nucleolar RNA, C/D box 116-19\|small nucleolar RNA, C/D box 116-15\|small nucleolar RNA, C/D box 116-16\|small nucleolar RNA, C/D box 116-18\|small nucleolar RNA, C/D box 116-21\|small nucleolar RNA, C/D box 116-22\|small nucleolar RNA, C/D box 116-14\|small nucleolar RNA, C/D box 116-20\|small nucleolar RNA, C/D box 116 cluster\|small nuclear ribonucleoprotein polypeptide N | Induced by miR-375 at baseline |
| 7981988 | SNORD116-20\|SNORD116@ | Small nucleolar RNA, C/D box 116-20\|small nucleolar RNA, CD box 116 cluster | Induced by miR-375 at baseline |
| 7981996 | SNORD116-24 | Small nucleolar RNA, C/D box 116-24 | Induced by miR-375 at baseline |
| 8006634 | PIGW | Phosphatidylinositol glycan anchor biosynthesis, class W | Induced by miR-375 at baseline |
| 8009380 | SNORA38B | Small nucleolar RNA, H/ACA box 38B (retrotransposed) | Induced by miR-375 at baseline |
| 8106193 | UTP15 | U3 small nucleolar RNA-associated protein 15 homolog | Induced by miR-375 at baseline |
| 8122440 | LTV1 | Yeast LTV1 homotog | Induced by miR-375 at baseline |
| 8132897 | LANCL2 | LanC lantibiotic synthetase component C-like 2 (bacterial) | Induced by miR-375 at baseline |
| 8132922 | MRPS17\|GBAS\|ZNF713 | Mitochondrial ribosomal protein S17\|glioblastoma amplified sequence\|zinc finger protein 713 | Induced by miR-375 at baseline |
| 8146685 | RRS1 | Homolog of yeast ribosome biogenesis regulatory protein RRS1 | Induced by miR-375 at baseline |
| 8146921 | RDH10 | Retinol dehydrogenase 10 (all-trans) | Induced by miR-375 at baseline |
| 8150537 | SLC20A2 | Solute carrier family 20 (phosphate transporter), member 2 | Induced by miR-375 at baseline |
| 8150908 | IMPAD1 | Inositol monophosphatase domain containing 1 | Induced by miR-375 at baseline |
| 7904106 | MAGI3 | Membrane associated guanylate kinase, WW and PDZ domain containing 3 | IL-13-mediated induction antagonized by miR-375 |
| 7908204 | HMCN1 | Hemicentin 1 | IL-13-mediated induction antagonized by miR-375 |
| 7917912 | DPYD | Dihydropyrimidine dehydrogenase | IL-13-mediated induction antagonized by miR-375 |
| 7920687 | GBAP1 | Glucosidase, beta, acid pseudogene 1 | IL-13-mediated induction antagonized by miR-375 |
| 7968872 | DNAJC15 | DnaJ (Hsp40) homolog, subfamily C, member 15 | IL-13-mediated induction antagonized by miR-375 |
| 7985752 | NCRNA00052 | Non-protein coding RNA 52 | IL-13-mediated induction antagonized by miR-375 |
| 7988360 | DUOX2 | Dual oxidase 2 | IL-13-mediated induction antagonized by miR-375 |
| 8040249 | PDIA6\|ATP6V1C2 | Protein disulfide isomerase family A, member 6\|ATPase, H+ transporting, lysosomal 42 kDa, V1 subunit C2 | IL-13-mediated induction antagonized by miR-375 |
| 8043036 | LOC1720 | Dihydrofolate reductase pseudogene | IL-13-mediated induction antagonized by miR-375 |
| 8076113 | LOC646851\|RP1-199H16.1 | Similar to OTTHUMP00000028720 | IL-13-mediated induction antagonized by miR-375 |

TABLE 11-continued

List of genes differentially regulated by miR-375 in esophageal epithelial cells before and after IL-13 stimulation.

| Transcript ID | Gene Symbol | Gene Description | Regulation |
|---|---|---|---|
| 8130129 | NUP43 | Nucleoporin 43 kDa | IL-13-mediated induction antagonized by miR-375 |
| 8140686 | SEMA3D | Sema domain, immunoglobulin domain (Ig), short basic domain, secreted, (semaphorin) 3D | IL-13-mediated induction antagonized by miR-375 |
| 6140971 | SAMD9L | Sterile alpha motif domain containing 9-like | IL-13-mediated induction antagonized by miR-375 |
| 7905154 | C1orf51 | Chromosome 1 open reading frame 51 | IL-13-mediated repression antagonized by miR-375 |
| 7975062 | SIPA1L2 | Signal-induced proliferation-associated 1 like 2 | IL-13-mediated repression antagonized by miR-375 |
| 7938485 | MICAL2 | Microtubule associated monoxygenase, calponin and LIM domain containing 2 | IL-13-mediated repression antagonized by miR-375 |
| 8069795 | CLDN8 | Claudin 8 | IL-13-mediated repression antagonized by miR-375 |
| 8020740 | DSG4 | Desmoglein 4 | IL-13-mediated repression antagonized by miR-375 |
| 8042283 | HSPC159 | Galectin-related protein | IL-13-mediated repression antagonized by miR-375 |
| 8056005 | ACVR1 | Activin A receptor, type 1 | IL-13-mediated repression antagonized by miR-375 |
| 8102800 | SLC7A11 | Solute carrier family 7, (cationic amino acid transporter, y+ system) member 11 | IL-13-mediated repression antagonized by miR-375 |
| 8115623 | ATP10B | ATPase, class V, type 10B | IL-13-mediated repression antagonized by miR-375 |
| 8164215 | SNORA65 | Small nucleolar RNA, H/ACA box 65 | IL-13-mediated repression antagonized by miR-375 |
| 7927936 | DDX21 | DEAD (Asp-Giu-Ala-Asp) box polypeptide 21 | IL-13-mediated induction potentiated by miR-375 |
| 7929047 | IFIT2 | Interferon-induced protein with tetratricopeptide repeats 2 | IL-13-mediated induction potentiated by miR-375 |
| 7938702 | DKFZp686O24166 | DKFZp686O24166 | IL-13-mediated induction potentiated by miR-375 |
| 7954382 | PYROXD1\|RECQL | Pyridine nucleotide-disulphide oxidoreductase domain 1\|RecQ protein-like (DNA helicase Q1-like) | IL-13-mediated induction potentiated by miR-375 |
| 8042830 | MTHFD2 | Methylenetetrahydrofolate dehydrogenase (NADP+ dependent) 2, methenyltetrahydrofolate cyclohydrolase | IL-13-mediated induction potentiated by miR-375 |
| 8047788 | ADAM 23 | ADAM metallopeptidase domain 23 | IL-13-mediated induction potentiated by miR-375 |
| 8062211 | RPF2\|BXDC1 | Ribosome production factor 2 homolog (*S. cerevisiae*)\|brix domain containing 1 | IL-13-mediated induction potentiated by miR-375 |
| 8069532 | HSPA13 | Heat shock protein 70 kDa family, member 13 | IL-13-mediated induction potentiated by miR-375 |
| 8084064 | MTHFD2 | Methyenetetrahydrofolate dehydrogenase (NADP+ dependent) 2, methenyltetrahydrofolate cyclohydrolase | IL-13-mediated induction potentiated by miR-375 |
| 8135774 | PTPRZ1 | Protein tyrosine phosphatase, receptor-type, Z polypeptide 1 | IL-13-mediated induction potentiated by miR-375 |
| 8142540 | FAM3C | Family with sequence similarity 3, member C | IL-13-mediated induction potentiated by miR-375 |
| 8166442 | FAM3C | Family with sequence similarity 3, member C | IL-13-mediated induction potentiated by miR-375 |
| 8171248 | KAL1 | Kallmann syndrome 1 sequence | IL-13-mediated induction potentiated by miR-375 |
| 7924450 | DUSP10 | Dual specificity phosphatase 10 | IL-13-mediated repression potentiated by miR-375 |
| 7962375 | PRICKLE1 | Prickle homolog 1 (*Drosophila*) | IL-13-mediated repression potentiated by miR-375 |
| 8127563 | COL12A1 | Collagen, type XII, alpha 1 | IL-13-mediated repression potentiated by miR-375 |
| 8133688 | SNORA14A | Small nucleolar RNA, H/ACA box 14A | IL-13-mediated repression potentiated by miR-375 |
| 8175683 | MIR224\|GABRE | MicroRNA 224\|gamma-aminobutyric acid (GABA) A receptor, epsilon | IL-13-mediated repression potentiated by miR-375 |
| 7965403 | LUM | Lumican | IL-13-mediated repression potentiated by miR-375 |
| 8026490 | UCA1 | Urothelial cancer associated 1 (non-protein coding) | IL-13-mediated repression potentiated by miR-375 |
| 8033674 | MUC16 | Mucin 16, cell surface associated | IL-13-mediated repression potentiated by miR-375 |
| 8049123 | ALPP | Alkaline phosphatase, placental (Regan isozyme) | IL-13-mediated repression potentiated by miR-375 |
| 8049128 | ALPPL2 | Alkaline phosphatase, placental-like 2 | IL-13-mediated repression potentiated by miR-375 |
| 8058765 | FN1 | Fibronectin 1 | IL-13-mediated repression potentiated by miR-375 |

TABLE 11-continued

List of genes differentially regulated by miR-375 in esophageal epithelial cells before and after IL-13 stimulation.

| Transcript ID | Gene Symbol | Gene Description | Regulation |
|---|---|---|---|
| 8104693 | PDZD2 | PDZ domain containing 2 | IL-13-mediated repression potentiated by miR-375 |
| 8126820 | GPR110 | G protein-coupled receptor 110 | IL-13-mediated repression potentiated by miR-375 |

TABLE 12

List of miR-375-regulated genes that are involved in immunoinflammatory responses.

| Gene ID | Gene Symbol | Gene Description | Disease Process |
|---|---|---|---|
| 90 | ACVR1 | Activin A receptor, type 1 | Inflammatory diseases |
| 154 | ADRB2 | Adrenergic, beta-2-, receptor, surface | Inflammatory diseases |
| 250 | ALPP | Alkaline phosphatase, placental | Inflammatory diseases |
| 275 | AMT | Aminomethyl transferase | Inflammatory diseases |
| 718 | C3 | Complement component 3 | Inflammatory diseases |
| 1147 | CHUK | Conserved helix-loop-helix ubiquitous kinase | Inflammatory diseases |
| 8448 | DOC2A | Double C2-like domains, alpha | Inflammatory diseases |
| 1806 | DPYD | Dihydropyrimidine dehydrogenase | Inflammatory diseases |
| 50506 | DUOX2 | Dual oxidase 2 | Inflammatory diseases |
| 11221 | DUSP10 | Dual specificity phosphatase 10 | Inflammatory diseases |
| 2335 | FN1 | Fibronectin 1 | Inflammatory diseases |
| 2550 | GABBR1 | Gamma-aminobutyric acid (GABA) B receptor, 1 | Inflammatory diseases |
| 2564 | GABRE | Gamma-aminobutyric acid (GABA) A receptor, epsilon | Inflammatory diseases |
| 55876 | GSDMB | Gasdermin B | Inflammatory diseases |
| 8942 | KYNU | Kynureninase (L-kynurenine hydrolase) | Inflammatory diseases |
| 3936 | LCP1 | Lymphocyte cytosolic protein 1 (L-plastin) | Inflammatory diseases |
| 646851 | LOC646851 | Hypothetical LOC646851 | Inflammatory diseases |
| 4060 | LUM | Lumican | Inflammatory diseases |
| 260425 | MAGI3 | Membrane-associated guanylate kinase, WW and PDZ domain containing 3 | Inflammatory diseases |
| 9645 | MICAL2 | Microtubule-associated monoxygenase, calponin and LIM domain containing 2 | Inflammatory diseases |
| 4321 | MMP12 | Matrix metallopeptidase 12 (macrophage elastase) | Inflammatory diseases |
| 143098 | MPP7 | Membrane protein, palmitoylated 7 (MAGUK p55 subfamily member 7) | Inflammatory diseases |
| 84276 | NICN1 | Nicolin 1 | Inflammatory diseases |
| 55714 | ODZ3 | Odz, odd Oz/ten-m homolog 3 (Drosophila) | Inflammatory diseases |
| 23037 | PDZD2 | PDZ domain containing 2 | Inflammatory diseases |
| 5288 | PIK3C2G | Phosphoinositide-3-kinase, class 2, gamma polypeptide | Inflammatory diseases |
| 22925 | PLA2R1 | Phospholipase A2 receptor 1, 180 kDa | Inflammatory diseases |
| 144165 | PRICKLE1 | Prickle homolog 1 (Drosophila) | Inflammatory diseases |
| 5803 | PTPRZ1 | Protein tyrosine phosphatase, receptor-type, Z polypeptide 1 | Inflammatory diseases |
| 5863 | RGL2 | Ral guanine nucleotide dissociation stimulator-like 2 | Inflammatory diseases |
| 219285 | SAMD9L | Sterile alpha motif domain containing 9-like | Inflammatory diseases |
| 223117 | SEMA3D | Sema domain, immunoglobulin domain (Ig), short basic domain, secreted, (semaphorin) 3D | Inflammatory diseases |
| 23657 | SLC7A11 | Solute earner family 7+ (cationic amino acid transporter, y+ system) member 11 | Inflammatory diseases |
| 6638 | SNRPN | Small nuclear ribonucleoprotein polypeptide N | Inflammatory diseases |
| 27148 | STK36 | Serine/threonine kinase 36, fused homolog (Drosophila) | Inflammatory diseases |
| 55959 | SULF2 | Sulfatase 2 | Inflammatory diseases |
| 120224 | TMEM45B | Transmembrane protein 45B | Inflammatory diseases |
| 84135 | UTP15 | UTP15, U3 small nucleolar ribonucleoprotein, homolog (S. cerevisiae) | Inflammatory diseases |
| 22882 | ZHX2 | Zinc fingers and homeoboxes 2 | Inflammatory diseases |
| 23613 | ZMYND8 | Zinc finger, MYND-type containing 8 | Inflammatory diseases |
| 8745 | ADAM23 | ADAM metallopeptidase domain 23 | Immunological diseases |
| 154 | ADRB2 | Adrenergic, beta-2-, receptor, surface | Immunological diseases |
| 718 | C3 | Complement component 3 | Immunological diseases |
| 1147 | CHUK | Conserved helix-loop-helix ubiquitous kinase | Immunological diseases |
| 8448 | DOC2A | Double C2-like domains, alpha | Immunological diseases |
| 1806 | DPYD | Dihydropyrimiddine dehydrogenase | Immunological diseases |
| 165545 | DQX1 | DEAQ box polypeptide 1 (RNA-dependent ATPase) | Immunological diseases |
| 11221 | DUSP10 | Dual specificity phosphatase 10 | Immunological diseases |
| 1906 | EDN1 | Endothelin 1 | Immunological diseases |
| 2335 | FN1 | Fibronectin 1 | Immunological diseases |
| 2550 | GABBR1 | Gamma-aminobutyric acid (GABA) B receptor, 1 | Immunological diseases |
| 2553 | GABPB2 | GA binding protein transcription factor, beta subunit 2 | Immunological diseases |
| 2564 | GABRE | Gamma-aminobutyric acid (GABA) A receptor, epsilon | Immunological diseases |
| 3433 | IFIT2 | Lnterferon-induced protein with tetratricopeptide repeats 2 | Immunological diseases |
| 3936 | LCP1 | Lymphocyte cytosolic protein 1 (L-plastin) | Immunological diseases |
| 646851 | LOC646851 | Hypothetical LOC646851 | Immunological diseases |
| 260425 | MAGI3 | Membrane-associated guanylate kinase, WW and PDZ domain containing 3 | Immunological diseases |
| 9645 | MICAL2 | Microtubule-associated monoxyrjenase, calponin and LIM domain containing 2 | Immunological diseases |
| 143098 | MPP7 | Membrane protein palmitoylated 7 | Immunological diseases |
| 55714 | ODZ3 | Odz, odd Oz/ten-m homolog 3 (Drosophila) | Immunological diseases |

TABLE 12-continued

List of miR-375-regulated genes that are involved in immunoinflammatory responses.

| Gene ID | Gene Symbol | Gene Description | Disease Process |
|---|---|---|---|
| 23037 | PDZD2 | PDZ domain containing 2 | Immunological diseases |
| 5288 | PIK3C2G | Phosphoinositide-3-kinase, class 2, gamma polypeptide | Immunological diseases |
| 22925 | PLA2R1 | Phospholipase A2 receptor 1, 180 kDa | Immunological diseases |
| 144165 | PRICKLE 1 | Prickle homolog 1 (*Drosophila*) | Immunological diseases |
| 5863 | RGL2 | Ral guanine nucleotide dissociation stimulator-like 2 | Immunological diseases |
| 219285 | SAMD9L | Sterile alpha motif domain containing 9-like | Immunological diseases |
| 57568 | SIPA1L2 | Signal-induced proliferation-associated 1 like 2 | Immunological diseases |
| 23657 | SLC7A11 | Solute carrier family 7, (cationic amino acid transporter, y+ system) member 11 | Immunological diseases |
| 6638 | SNRPN | Small nuclear ribonucleoprotein polypeptide N | Immunological diseases |
| 11329 | STK38 | Serine/threonine kinase 38 | Immunological diseases |
| 84135 | UTP15 | UTP15, U3 small nucleolar ribonucleoprolein, homolog (*S. cerevisiae*) | Immunological diseases |
| 22882 | ZHX2 | Zinc fingers and homeoboxes 2 | Immunological diseases |

Figure 32:
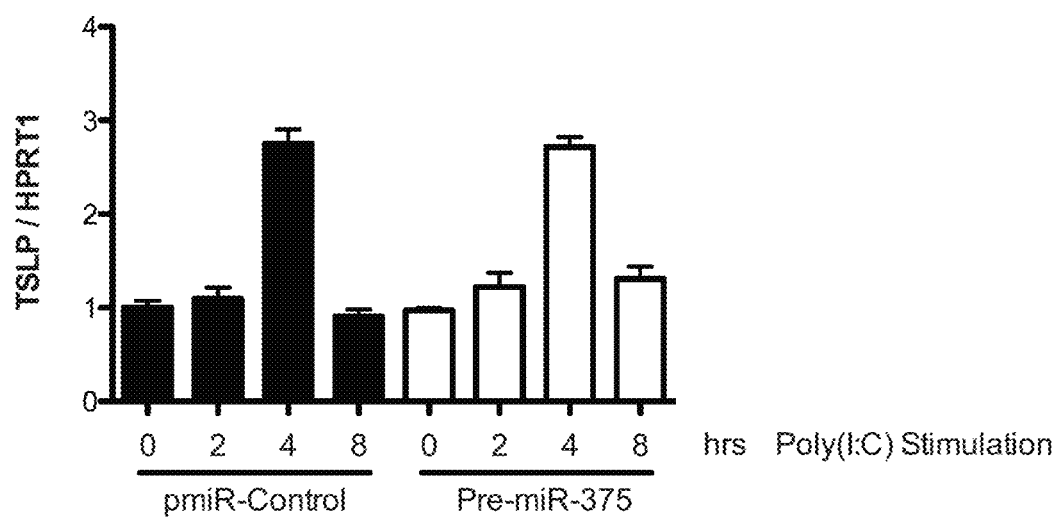
FIG. 32 depicts the expression levels of thymic stromal lymphopoietin (TSLP) in polyinosinic:polycytidylic acid (poly(I:C)) stimulated pre-miR-375-transduced TE-7 esophageal epithelial cells compared to controls. Control-transduced and pre-miR-375-transduced TE-7 cells were stimulated with 25 μg/mL poly(I:C) for 0, 2, 4, and 8 hours. Expression levels were determined by qPCR normalized to HPRT1. N=4 per group; data are represented as mean±SEM.

MiR-375 was found to have no effect on TSLP production (FIG. 31), and there was no correlation between miR-375 and TSLP in the esophageal samples. The control-transduced cells and pre-miR-375-transduced cells expressed TSLP at similar levels without stimulation and have similar levels of induction after polyinosinic:polycytidylic acid (polyI:C) stimulation (FIG. 32).

Example 26

Treatment of EE Based on Determination of miRNA Levels

Determination of level(s) of miRNAs associated with EE, as described herein, can be used to treat EE. For example, determination of level(s) of miRNAs associated with EE can be used to establish an EE diagnosis, which can then be used to determine an appropriate therapeutic strategy depending on the diagnosis.

The treatment method is carried out on a patient to determine the patient's level(s) of miRNAs associated with EE and whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE. A patient sample is analyzed for expression of at least one of the miRNAs, or a subset of the miRNAs or all of the miRNAs, as listed in Tables 2 and 3. The data is analyzed to determine expression levels of the miRNAs as disclosed herein to establish an EE diagnosis, which is then used to determine an appropriate therapeutic strategy depending on the diagnosis.

Example 27

Optimizing EE Treatment Based on Specific miRNA Levels

Determination of level(s) of miRNAs associated with EE, as described herein, can be used to treat EE to determine if a particular drug is or could potentially be effective. For example, the determination of level(s) of miRNAs associated with EE can be used to determine if a therapy specific for a molecule involved in EE disease pathogenesis up- or down-regulates certain EE-associated miRNAs.

As described in Example 6, miR-675 was found to be the only disease remission-induced miRNA, as miR-675 is up-regulated in glucocorticoid responder patients compared to normal, EE, or chronic esophagitis patients. Accordingly, miR-675 can be used to identify, and thereby determine an effective treatment strategy for, glucocorticoid responder patients, as well as EE patients who do not respond to glucocorticoid treatment.

Periostin has been demonstrated to have a key role in IL-13 associated remodeling responses. Accordingly, determination of level(s) of miRNAs associated with periostin can be used to identify, and thereby determine an effective treatment strategy for, anti-IL-13 responder patients, as well as EE patients who do not respond to anti-IL-13 treatment.

The treatment method is carried out on a patient to determine the patient's level(s) of miRNAs associated with EE and whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE. A patient sample is analyzed for expression of at least one of the miRNAs, or a subset of the miRNAs or all of the miRNAs, as listed in Tables 2 and 3. The data is analyzed to determine expression levels of the miRNAs as disclosed herein to establish an EE diagnosis, which is then used to determine an appropriate therapeutic strategy depending on the diagnosis.

The patient diagnosed with EE is evaluated to determine whether the patient is compliant with and/or exposed to steroid treatment by determining the patient's miR-675 level, wherein an elevated level of miR-675 indicates that the patient is compliant with and/or exposed to steroid treatment.

A patient diagnosed with EE for whom steroid therapy has been determined to be the appropriate therapeutic strategy is evaluated following treatment to determine whether the patient is responsive or non-responsive to steroid treatment, wherein an elevated level of miR-675 following treatment indicates that the patient is responsive to steroid treatment.

The patient diagnosed with EE is also evaluated to determine whether the patient is likely to be responsive or non-responsive to anti-IL-13 treatment, wherein an elevated level of one or more miRNAs associated with periostin levels, such as miR-223 and/or miR-375, indicates that the patient is likely to be responsive to anti-IL-13 treatment.

Example 28

Diagnosis of EE Based on Determination of miRNA Levels

Determination of level(s) of miRNAs associated with EE, as described herein, can be used to diagnose EE. For example, determination of level(s) of miRNAs associated with EE can be used to establish an EE diagnosis, which can then be used to determine an appropriate therapeutic strategy depending on the diagnosis.

The diagnostic method is carried out on a patient to determine the patient's level(s) of miRNAs associated with EE and whether the level of the one or more miRNAs is up-regulated or down-regulated relative to a level of the one or more miRNAs measured in a normal individual, wherein the presence of an elevated or reduced level of one or more miRNAs associated with EE results in the patient being diagnosed with EE. A patient sample is analyzed for expression of at least one of the miRNAs, or a subset of the miRNAs or all of the miRNAs, as listed in Tables 2 and 3. The data is analyzed to determine expression levels of the miRNAs as disclosed herein to establish an EE diagnosis.

Example 29

Diagnosis of Eosinophilic Disorders Based on Determination of miRNA Levels

Determination of miRNAs level(s), as described herein, can be used to treat eosinophilic disorders other than EE. For example, determination of level(s) of miRNAs associated with an eosinophilic disorder can be used to establish an eosinophilic disorder diagnosis, which can then be used to determine an appropriate therapeutic strategy depending on the diagnosis.

The miRNAs associated with EE can also be associated with cosinophilic disorders other than EE, such as EGID and asthma, given that they relate to eosinophil proliferation. For example, as described in Example 23, miR-375 has been shown to be involved in asthma. Accordingly, miR-375 can be used as a biomarker alone or in combination with other miRNAs shown to be involved with asthma, such as miR-21 and miR-223, and the like.

The treatment method is carried out on a patient to determine the patient's level(s) of miRNAs associated with an cosinophilic disorder and whether the level of the one or more miRNAs is up-regulated or down-regulated relative to a level of the one or more miRNAs measured in a normal individual, wherein the presence of an elevated or reduced level of one or more miRNAs associated with an cosino-philic disorder results in the patient being diagnosed with an cosinophilic disorder. A patient sample is analyzed for expression of at least one of the miRNAs, or a subset of the miRNAs or all of the miRNAs, as listed in Tables 2 and 3. The data is analyzed to determine expression levels of the miRNAs as disclosed herein to establish an eosinophilic disorder diagnosis, which is then used to determine an appropriate therapeutic strategy depending on the diagnosis.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of diagnosing a patient with eosinophilic esophagitis (EE), the method comprising
    analyzing a sample from the patient to determine the level of one or more micro RNA (miRNA) molecules in the sample using a diagnostic kit, test, or array, consisting of materials for quantification of four analytes, miR-146a, miR-146b, miR-142-3p and miR-223, which are miRNAs associated with eosinophilic esophagitis (EE),
    determining whether the level of the one or more miRNA molecules is higher or lower relative to normal controls, and
    diagnosing the patient as having EE if the level of the one or more miRNA molecules is higher than the normal controls.

2. The method of claim 1, wherein the sample is a plasma sample.

3. The method of claim 1, further comprising analyzing the sample from the patient to determine the level of one or more additional miRNA molecules, and diagnosing the patient as having EE if the level of the one or more additional miRNA is lower than the normal controls.

4. The method of claim 3, wherein the one or more additional miRNA molecules is selected from the group consisting of miR-375, miR-211, miR-210, miR-365, miR-203, miR-193a-5p, miR-193b, miR-193a-3p, let-7c, miR-144*, and miR-30a-3p.

5. The method of claim 1, further comprising analyzing the amount of one or more additional miRNA molecules selected from the group consisting of miR-886-5p, miR-886-3p, miR-222*, miR-7, miR-29b, miR-642, miR-339-5p, miR-21, miR-21*, miR-142-5p, miR-142-3p, miR-132, miR-212, miR-592, miR-92a-1*, miR-801, and miR-106b*.

6. The method of claim 5, wherein the one or more additional miRNA molecules comprises 10, 11, 12, 13, 14, 15, 16, 17, or 18 miRNAs.

7. The method of claim 1, wherein the sample is an esophageal tissue sample or a plasma sample.

8. The method of claim 1, wherein the sample is a buccal swab, an oral swish, or saliva.

9. The method of claim 1, further comprising obtaining the sample from the subject.

10. A diagnostic kit, test, or array, consisting of materials for quantification of four analytes, miR-146a, miR-146b, miR-142-3p and miR-223, which are miRNAs associated with eosinophilic esophagitis (EE).

11. The diagnostic kit, test, or array of claim 10, wherein the diagnostic kit, test, or array comprises a gene chip.

12. The diagnostic kit, test, or array of claim 11, wherein the gene chip comprises a low density array.

13. The diagnostic kit, test, or array of claim 10, wherein the diagnostic kit, test, or array comprises a surface with a DNA array.

* * * * *